(12) United States Patent
Wai et al.

(10) Patent No.: US 7,476,666 B2
(45) Date of Patent: Jan. 13, 2009

(54) HIV INTEGRASE INHIBITORS

(75) Inventors: John S. Wai, Harleysville, PA (US);
Peter D. Williams, Harleysville, PA (US); H. Marie Langford, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 89 days.

(21) Appl. No.: 11/629,153

(22) PCT Filed: Jun. 3, 2005

(86) PCT No.: PCT/US2005/022807

§ 371 (c)(1),
(2), (4) Date: Dec. 8, 2006

(87) PCT Pub. No.: WO2005/120516

PCT Pub. Date: Dec. 22, 2005

(65) Prior Publication Data

US 2008/0015187 A1 Jan. 17, 2008

Related U.S. Application Data

(60) Provisional application No. 60/578,170, filed on Jun. 9, 2004.

(51) Int. Cl.
*C07D 487/04* (2006.01)
*C07D 413/06* (2006.01)
*C07D 471/04* (2006.01)
*A61K 31/55* (2006.01)
*A61K 31/535* (2006.01)
*A61K 31/495* (2006.01)
*A61P 31/18* (2006.01)

(52) U.S. Cl. ............ 514/221; 514/233.2; 514/250; 540/502; 544/117; 544/346; 544/350

(58) Field of Classification Search ............ 514/221, 514/233.2, 250; 540/502; 544/117, 346, 544/350
See application file for complete search history.

(56) References Cited

U.S. PATENT DOCUMENTS

| 6,262,055 | B1 | 7/2001 | Young et al. |
| 6,306,891 | B1 | 10/2001 | Selnick et al. |
| 6,380,249 | B1 | 4/2002 | Young et al. |
| 2003/0055071 | A1 | 3/2003 | Anthony et al. |
| 2004/0229909 | A1 | 11/2004 | Kiyama et al. |
| 2005/0288293 | A1 | 12/2005 | Wai |

FOREIGN PATENT DOCUMENTS

| EP | 1422218 A1 | 5/2004 |
| WO | WO 01/00578 A1 | 1/2001 |
| WO | WO 02/30426 A1 | 4/2002 |
| WO | WO 02/36734 A2 | 5/2002 |
| WO | WO 02/055079 A2 | 7/2002 |
| WO | WO 03/035076 A1 | 5/2003 |
| WO | WO 03/035077 A1 | 5/2003 |
| WO | WO 03/062204 A1 | 7/2003 |
| WO | WO 2004/004657 A2 | 1/2004 |
| WO | WO 2004/024078 A2 | 1/2004 |
| WO | WO 2004/035576 A2 | 4/2004 |
| WO | WO 2004/035577 A2 | 4/2004 |
| WO | WO 2004/047725 A2 | 6/2004 |

OTHER PUBLICATIONS

Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).
Power, M.D., et al., "Nucleotide Sequence of SRV-1, a Type D Simian Acquired Immune Deficiency Syndrome Retrovirus", Science, vol. 231, pp. 1567-1572, (1986).
Pearl, L.H., et al., "A Structural Model for the Retroviral Proteases", Nature, vol. 329, pp. 351-354, (1987).

*Primary Examiner*—Bruck Kifle
(74) *Attorney, Agent, or Firm*—Kenneth R. Walton; Sheldon O. Heber

(57) ABSTRACT

Bicyclic pyrazoles of Formula I are inhibitors of HIV integrase and inhibitors of HIV replication:

(I)

wherein Z is O or N($R^8$); n is an integer equal to zero or 1; and $R^1$, $R^2$, $R^3$, $R^4$, $R^5$, $R^6$, $R^7$ and $R^8$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

11 Claims, No Drawings

HIV INTEGRASE INHIBITORS

This application is the National Stage of International Application No. PCT/US2005/022807, filed on Jun. 3, 2005, which claims the benefit of U.S. Provisional Application No. 60/578,170, filed Jun. 9, 2004, the disclosure of which is hereby incorporated by reference in its entirety.

FIELD OF THE INVENTION

The present invention is directed to certain bicyclic pyrazole compounds. The compounds of the present invention and their pharmaceutically acceptable salts are inhibitors of the HIV integrase enzyme and are useful for preventing or treating infection by HIV and for treating, delaying the onset of, or preventing AIDS.

BACKGROUND OF THE INVENTION

The retrovirus designated human immunodeficiency virus (HIV), particularly the strains known as HIV type-1 (HIV-1) and type-2 (HIV-2) viruses, have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., Nature 1985, 313: 277]. Amino acid sequence homology provides evidence that the pol sequence encodes reverse transcriptase, integrase and an HIV protease [Toh et al., EMBO J. 1985, 4: 1267; Power et al., Science 1986, 231: 1567; Pearl et al., Nature 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 2004/004657 discloses certain hydroxypyrrole derivatives that are HIV integrase inhibitors.

WO 2004/024078 discloses certain dihydroxypyridopyrazine-1,6-diones that are HIV integrase inhibitors.

WO 2004/035576 and WO 2004/035577 disclose certain tricyclic compounds that are HIV integrase inhibitors.

WO 2004/047725 (Publication of International Application No. PCT/US03/28363, filed Sep. 10, 2003) discloses certain 8-hydroxy-1-oxo-tetrahydropyrrolopyrazine compounds that are HIV integrase inhibitors.

SUMMARY OF THE INVENTION

The present invention is directed to (i) 3-hydroxy-4-oxo-4,5,6,7-tetrahydropyrazolo[1,5-a]pyrazine-2-carboxamides and 2-carboxylates and tetrahydropyrazolodiazepine analogs thereof and (ii) oxazine and oxazepine analogs of (i). These compounds and their pharmaceutically acceptable salts are useful in the inhibition of HIV integrase, the prevention of infection by HIV, the treatment of infection by HIV and in the prevention, treatment, and delay in the onset of AIDS, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes compounds of Formula I and pharmaceutically acceptable salts thereof:

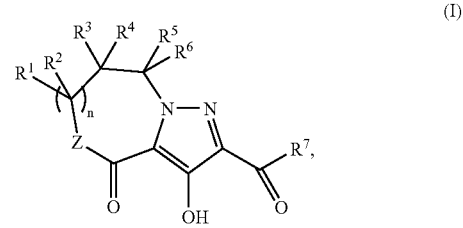

wherein:

Z is O or $N(R^8)$;

$R^1$ and $R^2$ are each independently
(1) H,
(2) $C_{1-6}$ alkyl,
(3) $C_{1-6}$ haloalkyl,
(4) $C_{1-6}$ alkyl substituted with —OH, —O—$C_{1-6}$ alkyl, —O—$C_{1-6}$ haloalkyl, —CN, —NO$_2$, —N($R^C$)$R^D$, —C(O)N($R^C$)$R^D$, —C(O)$R^A$, —CO$_2R^A$, —SR$^A$, —S(O)$R^A$, —SO$_2R^A$, —SO$_2$N($R^C$)$R^D$, —N($R^A$)C(O)$R^B$, —N($R^A$)CO$_2R^B$, —N($R^A$)SO$_2R^B$, —N($R^A$)SO$_2$N ($R^C$)$R^D$, —OC(O)N($R^C$)$R^D$, —N($R^A$)C(O)N($R^C$)$R^D$, or —N($R^A$)C(O)C(O)N($R^C$)$R^D$,
(5) CycA,
(6) AryA,
(7) HetA, or
(8) $C_{1-6}$ alkyl substituted with CycA, AryA, or HetA;

$R^3$, $R^4$, $R^5$ and $R^6$ are defined as follows:
(A) $R^3$, $R^4$, $R^5$ and $R^6$ are each independently:
(1) H,
(2) $C_{1-6}$ alkyl,
(3) $C_{1-6}$ haloalkyl,
(4) $C_{1-6}$ alkyl substituted with —OH, —O—$C_{1-6}$ alkyl, —O—$C_{1-6}$ haloalkyl, —CN, —NO$_2$, —N($R^C$)$R^D$, —C(O)N($R^C$)$R^D$, —C(O)$R^A$, —CO$_2R^A$, —S$R^A$, —S(O)$R^A$, —SO$_2R^A$, —SO$_2$N($R^C$)$R^D$, —N($R^A$)C(O)$R^B$, —N($R^A$)CO$_2R^B$, —N($R^A$)SO$_2R^B$, —N($R^A$)SO$_2$N($R^C$)$R^D$, —OC(O)N($R^C$)$R^D$, —N($R^A$)C(O)N($R^C$)$R^D$, or —N($R^A$)C(O)C(O)N($R^C$)$R^D$,
(5) C(O)N($R^C$)$R^D$,
(6) CycA,
(7) AryA,
(8) HetA, or
(9) $C_{1-6}$ alkyl substituted with CycA, AryA, or HetA; or
(B) $R^4$ and $R^5$ are each independently defined as in Part (A) above; and $R^3$ and $R^6$ together form a direct bond resulting in a carbon-carbon double bond; or
(C) $R^4$ and $R^5$ together with the carbon atoms to which they are attached form a 5- to 7-membered saturated or unsaturated ring optionally containing 1 or 2 heteroatoms independently selected from N, O and S, wherein the ring is optionally substituted with from 1 to 6 substituents each of which is independently halogen, —$C_{1-6}$ alkyl, —OH, —O—$C_{1-6}$ alkyl, oxo, —CN, —NO$_2$, or —N($R^A$)$R^B$; and $R^3$ and $R^6$ are either both absent or are each independently defined as in Part (A) above;

$R^7$ is:
(1) OH,
(2) O—$C_{1-6}$ alkyl,
(3) O-CycA,
(4) O—$C_{1-6}$ alkylene-CycA,
(5) O—$C_{1-6}$ alkylene-AryA,
(6) O—$C_{1-6}$ alkylene-HetA, or
(7) N($R^U$)$R^V$;

$R^8$ is:
(1) H,
(2) $C_{1-6}$ alkyl,
(3) $C_{1-6}$ haloalkyl,
(4) $C_{1-6}$ alkyl substituted with —OH, —O—$C_{1-6}$ alkyl, —O—$C_{1-6}$ haloalkyl, —CN, —NO$_2$, —N($R^C$)$R^D$, —C(O)N($R^C$)$R^D$, —C(O)$R^A$, —CO$_2R^A$, —S$R^A$, —S(O)$R^A$, —SO$_2R^A$, —SO$_2$N($R^C$)$R^D$, —N($R^A$)C(O)$R^B$, —N($R^A$)CO$_2R^B$, —N($R^A$)SO$_2R^B$, —N($R^A$)SO$_2$N($R^C$)$R^D$, —OC(O)N($R^C$)$R^D$, —N($R^A$)C(O)N($R^C$)$R^D$, or —N($R^A$)C(O)C(O)N($R^C$)$R^D$,
(5) CycA, or
(6) $C_{1-6}$ alkyl substituted with CycA, AryA, or HetA;

n is an integer equal to zero or 1;

each $R^A$ is independently —H or —$C_{1-6}$ alkyl;

each $R^B$ is independently —H or —$C_{1-6}$ alkyl;

$R^C$ and $R^D$ are each independently —H or —$C_{1-6}$ alkyl; or $R^C$ and $R^D$ together with the N atom to which they are both attached form a 3- to 8-membered saturated ring containing (i) the N atom to which they are both attached, (ii) at least two carbon atoms, and (iii) optionally 1 or 2 additional heteroatoms independently selected from N, O and S; wherein the ring is optionally substituted with from 1 to 6 substituents each of which is independently halogen, —$C_{1-6}$ alkyl, —OH, —O—$C_{1-6}$ alkyl, oxo, —CN, —NO$_2$, or —N($R^A$)$R^B$;

$R^U$ and $R^V$ are each independently:
(i) H,
(ii) $C_{1-6}$ alkyl,
(iii) $C_{1-6}$ haloalkyl,
(iv) $C_{1-6}$ alkyl substituted with —OH, —O—$C_{1-6}$ alkyl, —O—$C_{1-6}$ haloalkyl, —CN, —NO$_2$, —N($R^C$)$R^D$, —C(O)N($R^C$)$R^D$, —C(O)$R^A$, —CO$_2R^A$, —S$R^A$, —S(O)$R^A$, —SO$_2R^A$, —SO$_2$N($R^C$)$R^D$, —N($R^A$)C(O)$R^B$, —N($R^A$)CO$_2R^B$, —N($R^A$)SO$_2R^B$, —N($R^A$)SO$_2$N($R^C$)$R^D$, —OC(O)N($R^C$)$R^D$, —N($R^A$)C(O)N($R^C$)$R^D$, or —N($R^A$)C(O)C(O)N($R^C$)$R^D$,
(v) CycA,
(vi) HetC, or
(vii) $C_{1-6}$ alkyl substituted with CycA, AryA, HetA, or HetC, with the proviso that the atom in HetC attached to the alkyl group is not a N atom; or $R^U$ and $R^V$ together with the N atom to which they are both attached form a 3- to 8-membered saturated ring containing (i) the N atom to which they are both attached, (ii) at least two carbon atoms, and (iii) optionally containing 1 or 2 additional heteroatoms independently selected from N, O and S; wherein the saturated ring is optionally fused with a benzene ring and the optionally fused, saturated ring is:
(i) optionally substituted with from 1 to 6 substituents each of which is independently halogen, —$C_{1-6}$ alkyl, —OH, —O—$C_{1-6}$ alkyl, oxo, —CN, —NO$_2$, or —N($R^A$)$R^B$, and
(ii) optionally substituted with 1 or 2 substituents each of which is independently CycA, AryA, HetA, HetC, or $C_{1-6}$ alkyl substituted with CycA, AryA, HetA or HetC;

each CycA is independently a $C_{3-8}$ cycloalkyl which is:
(i) optionally substituted with from 1 to 6 substituents each of which is independently halogen, —$C_{1-6}$ alkyl, —OH, —O—$C_{1-6}$ alkyl, or —$C_{1-6}$ haloalkyl, and
(ii) optionally substituted with 1 or 2 substituents each of which is independently:
(1) AryB,
(2) HetB,
(3) CycB, or
(4) $C_{1-6}$ alkyl substituted with CycB, AryB, or HetB;

each AryA is independently an aryl which is:
(i) optionally substituted with from 1 to 5 substituents each of which is independently:
(1) —$C_{1-6}$ alkyl, which is optionally substituted with —OH, —O—$C_{1-6}$ alkyl, —O—$C_{1-6}$ haloalkyl, —CN, —NO$_2$, —N($R^A$)$R^B$, —C(O)N($R^A$)$R^B$, —C(O)$R^A$, —CO$_2R^A$, —S$R^A$, —S(O)$R^A$, —SO$_2R^A$, —SO$_2$N($R^A$)$R^B$, —N($R^A$)C(O)$R^B$, —N($R^A$)CO$_2R^B$, —N($R^A$)SO$_2R^B$, —N($R^A$)SO$_2$N($R^A$)$R^B$, —OC(O)N($R^A$)$R^B$, —N($R^A$)C(O)N($R^A$)$R^B$, or —N($R^A$)C(O)C(O)N($R^A$)$R^B$,
(2) —O—$C_{1-6}$ alkyl,
(3) —$C_{1-6}$ haloalkyl,
(4) —O—$C_{1-6}$ haloalkyl,
(5) —OH,
(6) halogen,
(7) —CN,
(8) —NO$_2$,
(9) —N($R^A$)$R^B$,
(10) —C(O)N($R^A$)$R^B$,

(11) —C(O)$R^A$,
(12) —CO$_2$$R^A$,
(13) —S$R^A$,
(14) —S(=O)$R^A$,
(15) —SO$_2$$R^A$,
(16) —SO$_2$N($R^A$)$R^B$,
(17) —N($R^A$)SO$_2$$R^B$,
(18) —N($R^A$)SO$_2$N($R^A$)$R^B$,
(19) —N($R^A$)C(O)$R^B$,
(20) —N($R^A$)C(O)—C(O)N($R^A$)$R^B$, or
(21) —N($R^A$)CO$_2$$R^B$, and (ii) optionally substituted with 1 or 2 substituents each of which is independently:
(1) AryB,
(2) HetB,
(3) CycB,
(4) —$C_{1-6}$ alkyl substituted with CycB, AryB or HetB,
(5) —C(O)N($R^A$)-CycB or
(6) —C(O)O-CycB;

each HetA is independently a heteroaryl which is:
(i) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, or —OH; and
(ii) optionally substituted with 1 or 2 substituents each of which is independently AryB, HetB, CycB, or —$C_{1-6}$ alkyl substituted with AryB, HetB or CycB;

each AryB is independently phenyl or naphthyl, wherein the phenyl or naphthyl is optionally substituted with from 1 to 5 substituents each of which is independently any one of the substituents (1) to (21) as defined above in part (i) of the definition of AryA;

each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy;

each CycB is independently a $C_{3-8}$ cycloalkyl which is optionally substituted with from 1 to 6 substituents each of which is independently halogen, —$C_{1-6}$ alkyl, —OH, —O—$C_{1-6}$ alkyl, or —$C_{1-6}$ haloalkyl;

HetC is a 4- to 7-membered saturated heterocyclic ring containing from 1 to 4 heteroatoms independently selected from N, O and S, wherein the heterocyclic ring is optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo;

each aryl is independently (i) phenyl or (ii) a 9- or 10-membered bicyclic, fused carbocyclic ring system in which at least one ring is aromatic; and each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$.

The present invention also includes pharmaceutical compositions containing a compound of Formula I and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the bicyclic pyrazole compounds of Formula I above. These compounds and pharmaceutically acceptable salts thereof inhibit HIV integrase and inhibit HIV (e.g., HIV-1) replication. A first embodiment of the present invention is a compound of Formula I, or a pharmaceutically acceptable salt thereof, wherein each AryA is independently an aryl which is:
(i) optionally substituted with from 1 to 5 substituents each of which is independently any one of the substituents (1) to (21) in part (i) of the definition of AryA set forth above in the Summary of the Invention, and
(ii) optionally substituted with 1 or 2 substituents each of which is independently:
(1) AryB,
(2) HetB,
(3) CycB, or
(4) —$C_{1-6}$ alkyl substituted with CycB, AryB or HetB;

and all other variables are as defined in the Summary of the Invention.

A second embodiment of the present invention is a compound of Formula I, or a pharmaceutically acceptable salt thereof, wherein $R^1$ and $R^2$ are each independently:
(1) H,
(2) $C_{1-4}$ alkyl,
(3) $C_{1-4}$ alkyl substituted with —OH, —O—$C_{1-4}$ alkyl, —N($R^C$)$R^D$, —C(O)N($R^C$)$R^D$, —C(O)$R^A$, —CO$_2$$R^A$, —S$R^A$, —S(O)$R^A$, —SO$_2$$R^A$, —SO$_2$N($R^C$)$R^D$, —N($R^A$)C(O)$R^B$, —N($R^A$)CO$_2$$R^B$, —N($R^A$)C(O)N($R^C$)$R^D$, or —N($R^A$)C(O)C(O)N($R^C$)$R^D$,
(4) CycA,
(5) AryA,
(6) HetA, or
(7) $C_{1-4}$ alkyl substituted with CycA, AryA, or HetA;

and all other variables are as originally defined (i.e., as defined in the Summary of the Invention) or as defined in the first embodiment.

A third embodiment of the present invention is a compound of Formula I, or a pharmaceutically acceptable salt thereof, wherein one of $R^1$ and $R^2$ is H or $C_{1-4}$ alkyl; and the other of $R^1$ and $R^2$ is:
(1) H,
(2) $C_{1-4}$ alkyl,
(3) $C_{1-4}$ alkyl substituted with —OH, —O—$C_{1-4}$ alkyl, —N($R^C$)$R^D$, —C(O)N($R^C$)$R^D$, —C(O)$R^A$, —CO$_2$$R^A$, —S$R^A$, —S(O)$R^A$, —SO$_2$$R^A$, —SO$_2$N($R^C$)$R^D$, —N($R^A$)C(O)$R^B$, —N($R^A$)CO$_2$$R^B$, —N($R^A$)C(O)N($R^C$)$R^D$, or —N($R^A$)C(O)C(O)N($R^C$)$R^D$,
(4) CycA,
(5) AryA,
(6) HetA, or
(7) $C_{1-4}$ alkyl substituted with CycA, AryA, or HetA;

and all other variables are as originally defined or as defined in the first embodiment.

A fourth embodiment of the present invention is a compound of Formula I, or a pharmaceutically acceptable salt thereof, wherein one of $R^1$ and $R^2$ is H or $C_{1-4}$ alkyl; and the other of $R^1$ and $R^2$ is:
(1) H,
(2) $C_{1-4}$ alkyl,
(3) $C_{1-3}$ alkyl substituted with —N($R^C$)$R^D$ or —C(O)N($R^C$)$R^D$,
(4) CycA, AryA, or HetA,
(5) $(CH_2)_{1-2}$-CycA, $(CH_2)_{1-2}$-AryA, or $(CH_2)_{1-2}$-HetA, or
(6) $CH(CH_3)$-CycA, $CH(CH_3)$-AryA, or $CH(CH_3)$-HetA;

and all other variables are as originally defined or as defined in the first embodiment.

A fifth embodiment of the present invention is a compound of Formula I, or a pharmaceutically acceptable salt thereof, wherein $R^1$ and $R^2$ are each independently H or $C_{1-4}$ alkyl; and all other variables are as originally defined or as defined in the first embodiment.

A sixth embodiment of the present invention is a compound of Formula I, or a pharmaceutically acceptable salt thereof, wherein $R^1$ and $R^2$ are both H; and all other variables are as originally defined or as defined in the first embodiment.

A seventh embodiment of the present invention is a compound of Formula I, or a pharmaceutically acceptable salt thereof, wherein $R^3$, $R^4$, $R^5$ and $R^6$ are defined as follows:
(A) $R^3$, $R^4$, $R^5$ and $R^6$ are each independently
  (1) H,
  (2) $C_{1-4}$ alkyl,
  (3) $C_{1-4}$ alkyl substituted with —OH, —O—$C_{1-4}$ alkyl, —N($R^C$)$R^D$, —C(O)N($R^C$)$R^D$, —C(O)$R^A$, —CO$_2R^A$, —S$R^A$, —S(O)$R^A$, —SO$_2R^A$, —SO$_2$N($R^C$)$R^D$, —N($R^A$)C(O)$R^B$, —N($R^A$)CO$_2R^B$, —N($R^A$)C(O)N($R^C$)$R^D$, or —N($R^A$)C(O)C(O)N($R^C$)$R^D$,
  (4) C(O)N($R^C$)$R^D$,
  (5) CycA,
  (6) AryA,
  (7) HetA, or
  (8) $C_{1-4}$ alkyl substituted with CycA, AryA, or HetA;
(B) $R^4$ and $R^5$ are each independently defined as in Part (A) above; and $R^3$ and $R^6$ together form a direct bond resulting in a carbon-carbon double bond; or
(C) $R^4$ and $R^5$ together with the carbon atoms to which they are attached form a 5- to 7-membered saturated or unsaturated carbocyclic ring which is optionally substituted with from 1 to 4 substituents each of which is independently halogen, —$C_{1-4}$ alkyl, —OH, or —O—$C_{1-14}$ alkyl; and $R^3$ and $R^6$ are either both absent or are each independently defined as in Part (A) above;

and all other variables are as originally defined or as defined in any one of the preceding embodiments. The term "$R^3$ and $R^6$ are both absent" in Part (C) above and elsewhere herein is understood to mean that there are no substituents corresponding to $R^3$ and $R^6$ in the compound and that free valences resulting from the absence of these substituents are satisfied by the presence of unsaturation in the ring formed by $R^4$ and $R^5$ (e.g., when $R^4$ and $R^5$ together with the carbon atoms to which they are attached form a benzene ring).

A eighth embodiment of the present invention is a compound of Formula I, or a pharmaceutically acceptable salt thereof, wherein $R^3$, $R^4$, $R^5$ and $R^6$ are defined as follows:
(A) $R^3$ and $R^6$ are each independently H or $C_{1-4}$ alkyl; and $R^4$ and $R^5$ are each independently:
  (1) H,
  (2) $C_{1-4}$ alkyl,
  (3) C(O)N($R^C$)$R^D$,
  (4) $C_{1-3}$ alkyl substituted with —N($R^C$)$R^D$ or —C(O)N($R^C$)$R^D$,
  (5) CycA, AryA, or HetA,
  (6) $(CH_2)_{1-2}$-CycA, $(CH_2)_{1-2}$-AryA, or $(CH_2)_{1-2}$-HetA, or
  (7) $CH(CH_3)$-CycA, $CH(CH_3)$-AryA, or $CH(CH_3)$-HetA;
(B) $R^4$ and $R^5$ are each independently defined as in Part (A) above; and $R^3$ and $R^6$ together form a direct bond resulting in a carbon-carbon double bond; or
(C) $R^4$ and $R^5$ together with the carbon atoms to which they are attached form a benzene ring which is optionally substituted with from 1 to 4 substituents each of which is independently halogen, —$C_{1-4}$ alkyl, —OH, or —O—$C_{1-4}$ alkyl; and $R^3$ and $R^6$ are both absent;

and all other variables are as originally defined or as defined in any one of the preceding embodiments.

A ninth embodiment of the present invention is a compound of Formula I, or a pharmaceutically acceptable salt thereof, wherein $R^3$, $R^4$, $R^5$ and $R^6$ are defined as follows:
(A) $R^3$ and $R^6$ are each independently H or $C_{1-4}$ alkyl; one of $R^4$ and $R^5$ is H or $C_{1-4}$ alkyl, and the other of $R^4$ and $R^5$ is:
  (1) H,
  (2) $C_{1-4}$ alkyl,
  (3) C(O)N($R^C$)$R^D$,
  (4) $(CH_2)_{1-3}$—N($R^C$)$R^D$ or $(CH_2)_{1-3}$—C(O)N($R^C$)$R^D$,
  (5) CycA, AryA, or HetA, or
  (6) $CH_2$-CycA, $CH_2$-AryA, or $CH_2$-HetA;
(B) $R^4$ and $R^5$ are each defined as in Part (A) above; and $R^3$ and $R^6$ together form a direct bond resulting in a carbon-carbon double bond; or
(C) $R^4$ and $R^5$ together with the carbon atoms to which they are attached form a benzene ring which is optionally substituted with from 1 to 4 substituents each of which is independently halogen, —$C_{1-4}$ alkyl, —OH, or —O—$C_{1-4}$ alkyl; and $R^3$ and $R^6$ are both absent;

and all other variables are as originally defined or as defined in any one of the preceding embodiments.

A tenth embodiment of the present invention is a compound of Formula I, or a pharmaceutically acceptable salt thereof, wherein $R^3$, $R^4$, $R^5$ and $R^6$ are defined as follows:
(A) $R^3$ is H; $R^4$ is H or methyl; $R^6$ is H or methyl; and $R^5$ is H, $C_{1-3}$ alkyl, $(CH_2)_{1-2}NH_2$, $(CH_2)_{1-2}NH(C_{1-3}$ alkyl), $(CH_2)_{1-2}N(C_{1-3}$ alkyl)$_2$,

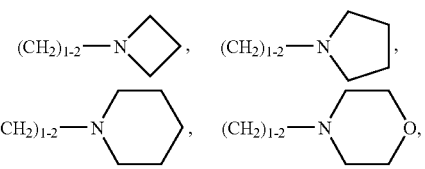

C(O)NH$_2$, C(O)NH($C_{1-3}$ alkyl), C(O)N($C_{1-3}$ alkyl)$_2$,

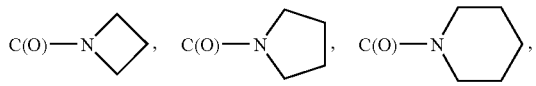

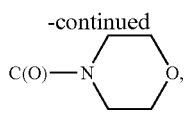

phenyl optionally substituted with 1 or 2 substituents independently selected from halogen and CN, benzyl, or a heteroaromatic ring selected from the group consisting of pyrrolyl, pyrazolyl, imidazolyl, oxazolyl, thiazolyl, triazolyl, oxadiazolyl, thiadiazolyl, pyridinyl, pyrimidinyl, and pyrazinal, wherein the heteroaromatic ring is optionally substituted with 1 or 2 substituents each of which is independently methyl, ethyl, n-propyl, or isopropyl;

(B) $R^4$ and $R^5$ are each defined as in Part (A) above; and $R^3$ and $R^6$ together form a direct bond resulting in a carbon-carbon double bond; or (C) $R^4$ and $R^5$ together with the carbon atoms to which they are attached form a benzene ring; and $R^3$ and $R^6$ are both absent;

and all other variables are as originally defined or as defined in any one of the preceding embodiments.

An eleventh embodiment of the present invention is identical to the tenth embodiment except that $R^5$ in Part (A) is H, methyl, $(CH_2)_{1-2}NH_2$, $(CH_2)_{1-2}NH(C_{1-3}$ alkyl), $(CH_2)_{1-2}N(C_{1-3}$ alkyl)$_2$,

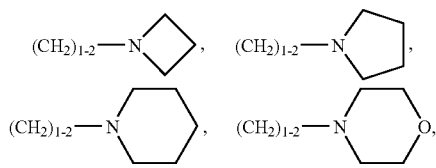

$C(O)NH_2$, $C(O)NH(C_{1-3}$ alkyl), $C(O)N(C_{1-3}$ alkyl)$_2$,

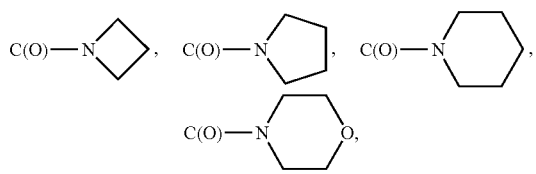

phenyl, benzyl, or a heteroaromatic ring selected from the group consisting of pyrrolyl, pyrazolyl, imidazolyl, oxazolyl, thiazolyl, triazolyl, oxadiazolyl, thiadiazolyl, pyridinyl, pyrimidinyl, and pyrazinal, wherein the heteroaromatic ring is optionally substituted with 1 or 2 substituents each of which is independently methyl, ethyl, n-propyl, or isopropyl.

A twelfth embodiment of the present invention is a compound of Formula I, or a pharmaceutically acceptable salt thereof, wherein $R^3$, $R^4$, $R^5$ and $R^6$ are all H; and all other variables are as originally defined or as defined in any one of the preceding embodiments.

A thirteenth embodiment of the present invention is a compound of Formula I, or a pharmaceutically acceptable salt thereof, wherein $R^7$ is:

(1) O—$C_{1-4}$ alkyl,
(2) O-CycA,
(3) O—$C_{1-6}$ alkylene-CycA,
(4) O—$C_{1-6}$ alkylene-AryA,
(5) O—$C_{1-6}$ alkylene-HetA, or
(6) $N(R^U)R^V$;

and all other variables are as originally defined or as defined in any one of the preceding embodiments.

A fourteenth embodiment of the present invention is a compound of Formula I, or a pharmaceutically acceptable salt thereof, wherein $R^7$ is: (1) O—$C_{1-4}$ alkyl, or (2) $N(R^U)R^V$; and all other variables are as originally defined or as defined in any one of the preceding embodiments.

A fifteenth embodiment of the present invention is a compound of Formula I, or a pharmaceutically acceptable salt thereof, wherein $R^8$ is:

(1) H,
(2) $C_{1-4}$ alkyl,
(3) $C_{1-4}$ alkyl substituted with —$N(R^C)R^D$, —$C(O)N(R^C)R^D$, —$C(O)R^A$, —$CO_2R^A$, —$SR^A$, —$S(O)R^A$, —$SO_2R^A$, —$SO_2N(R^C)R^D$, —$N(R^A)C(O)R^B$, —$N(R^A)CO_2R^B$, —$N(R^A)C(O)N(R^C)R^D$, or —$N(R^A)C(O)C(O)N(R^C)R^D$,
(4) CycA, or
(5) $C_{1-4}$ alkyl substituted with CycA, AryA, or HetA;

and all other variables are as originally defined or as defined in any one of the preceding embodiments.

A sixteenth embodiment of the present invention is a compound of Formula I, or a pharmaceutically acceptable salt thereof, wherein $R^8$ is:

(1) H,
(2) $C_{1-4}$ alkyl,
(3) $C_{1-3}$ alkyl substituted with —$N(R^C)R^D$ or —$C(O)N(R^C)R^D$,
(4) $C_{3-6}$ cycloalkyl,
(5) $(CH_2)_{1-2}$-CycA, $(CH_2)_{1-2}$-AryA, or $(CH_2)_{1-2}$-HetA, or
(6) $CH(CH_3)$-CycA, $CH(CH_3)$-AryA, or $CH(CH_3)$-HetA;

and all other variables are as originally defined or as defined in any one of the preceding embodiments.

A seventeenth embodiment of the present invention is a compound of Formula I, or a pharmaceutically acceptable salt thereof, wherein $R^8$ is:

(1) H,
(2) $C_{1-4}$ alkyl,
(3) $(CH_2)_{1-3}$—$N(R^C)R^D$ or $(CH_2)_{1-3}$—$C(O)N(R^C)R^D$,
(4) $C_{3-6}$ cycloalkyl, or
(5) $CH_2$-CycA, $CH_2$-AryA, or $CH_2$-HetA;

and all other variables are as originally defined or as defined in any one of the preceding embodiments.

An eighteenth embodiment of the present invention is a compound of Formula I, or a pharmaceutically acceptable salt thereof, wherein each $R^A$ is independently H or $C_{1-4}$ alkyl; each $R^B$ is independently H or $C_{1-4}$ alkyl; and all other variables are as originally defined or as defined in any one of the preceding embodiments.

A nineteenth embodiment of the present invention is a compound of Formula I, or a pharmaceutically acceptable salt thereof, wherein each $R^A$ and $R^B$ is independently H or methyl; and all other variables are as originally defined or as defined in any one of the preceding embodiments.

A twentieth embodiment of the present invention is a compound of Formula I, or a pharmaceutically acceptable salt thereof, wherein $R^C$ and $R^D$ are each independently —H or —$C_{1-4}$ alkyl; or $R^C$ and $R^D$ together with the N atom to which they are both attached form a 3- to 6-membered saturated ring containing (i) the N atom to which they are both attached, (ii) at least two carbon atoms, and (iii) optionally an additional heteroatom independently selected from N, O and S; wherein the ring is optionally substituted with from 1 to 5 substituents each of which is independently halogen, —C$_{1-4}$ alkyl, or oxo; and all other variables are as originally defined or as defined in any one of the preceding embodiments.

A twenty-first embodiment of the present invention is a compound of Formula I, or a pharmaceutically acceptable salt thereof, wherein R$^C$ and R$^D$ are each independently —H or —C$_{1-4}$ alkyl; or R$^C$ and R$^D$ together with the N atom to which they are both attached form

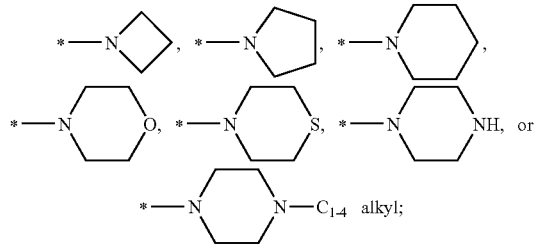

and all other variables are as originally defined or as defined in any one of the preceding embodiments. The asterisk * denotes the point of attachment of the group to the rest of the compound.

A twenty-second embodiment of the present invention is a compound of Formula I, or a pharmaceutically acceptable salt thereof, wherein R$^U$ and R$^V$ are each independently:
  (i) H,
  (ii) C$_{1-4}$ alkyl,
  (iii) C$_{1-4}$ alkyl substituted with —OH, —O—C$_{1-14}$ alkyl, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)C(O)N(R$^C$)R$^D$, or —N(R$^A$)C(O)C(O)N(R$^C$)R$^D$,
  (iv) CycA,
  (v) HetC, or
  (vi) C$_{1-4}$ alkyl substituted with CycA, AryA, HetA, or HetC, with the proviso that the atom in HetC attached to the alkyl group is not a N atom; or R$^U$ and R$^V$ together with the N atom to which they are both attached form a 4- to 7-membered saturated ring containing (i) the N atom to which they are both attached, (ii) at least two carbon atoms, and (iii) optionally containing an additional heteroatom independently selected from N, O and S; wherein the saturated ring is optionally fused with a benzene ring and the optionally fused, saturated ring is:
  (i) optionally substituted with from 1 to 5 substituents each of which is independently halogen, —C$_{1-6}$ alkyl, —OH, oxo, —CN, —NO$_2$, or —N(R$^A$)R$^B$, and
  (ii) optionally substituted with CycA, AryA, HetA, HetC, or C$_{1-4}$ alkyl substituted with CycA, AryA, HetA or HetC;

and all other variables are as originally defined or as defined in any one of the preceding embodiments.

A twenty-third embodiment of the present invention is a compound of Formula I, or a pharmaceutically acceptable salt thereof, wherein R$^U$ is:
  (i) H,
  (ii) C$_{1-4}$ alkyl,
  (iii) C$_{2-4}$ alkyl substituted with OH, O—C$_{1-4}$ alkyl, NH$_2$, NH(C$_{1-4}$ alkyl), or N(C$_{1-4}$ alkyl)$_2$;

R$^V$ is:
  (i) H,
  (ii) C$_{1-4}$ alkyl,
  (iii) C$_{1-3}$ alkyl substituted with —N(R$^C$)R$^D$ or —C(O)N(R$^C$)R$^D$,
  (iv) a saturated heterocycle selected from the group consisting of:

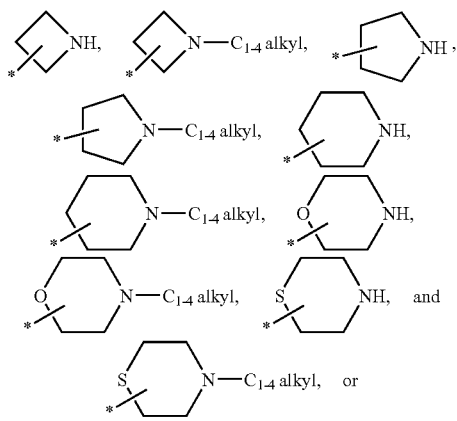

(v) (CH$_2$)$_{1-2}$-CycA, (CH$_2$)$_{1-2}$-AryA, or (CH$_2$)$_{1-2}$-HetA, or
  (vi) CH(CH$_3$)-CycA, CH(CH$_3$)-AryA, or CH(CH$_3$)-HetA;

or alternatively R$^U$ and R$^V$ together with the N atom to which they are both attached form a saturated heterocyclic ring optionally fused to a benzene ring, wherein the optionally fused heterocyclic ring is selected from the group consisting of:

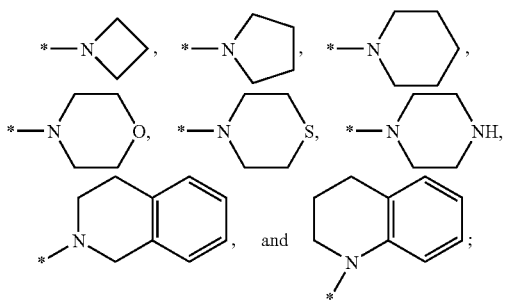

wherein the ring is optionally substituted with a phenyl, is optionally substituted with 1 or 2-C$_{1-4}$ alkyl groups, and is optionally substituted with an oxo, with the proviso that the optional oxo substituent is attached to a carbon atom in the saturated heterocyclic ring;

and all other variables are as originally defined or as defined in any one of the preceding embodiments.

A twenty-fourth embodiment of the present invention is a compound of Formula I, or a pharmaceutically acceptable salt thereof, wherein R$^U$ is:
  (i) H,
  (ii) C$_{1-4}$ alkyl, or
  (iii) (CH$_2$)$_{2-4}$T, wherein T is selected from the group consisting of OH, O—C$_{1-4}$ alkyl, NH$_2$, NH(C$_{1-4}$ alkyl), and N(C$_{1-4}$ alkyl)$_2$;

$R^V$ is:
(i) H,
(ii) $C_{1-4}$ alkyl,
(iii) $(CH_2)_{1-3}$—N($R^C$)$R^D$ or $(CH_2)_{1-3}$—C(O)N($R^C$)$R^D$,
(iv) a saturated heterocycle selected from the group consisting of:

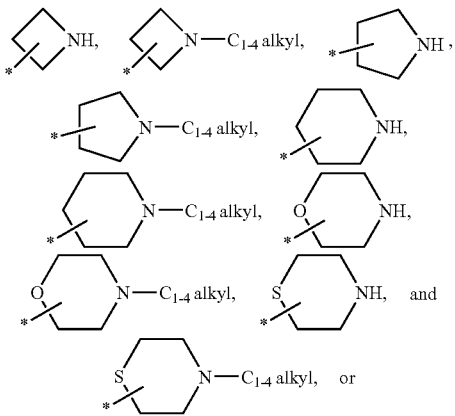

(v) $CH_2$-CycA, $CH_2$-AryA, or $CH_2$-HetA;

or alternatively $R^U$ and $R^V$ together with the N atom to which they are both attached form a saturated heterocyclic ring optionally fused to a benzene ring, wherein the optionally fused heterocyclic ring is selected from the group consisting of:

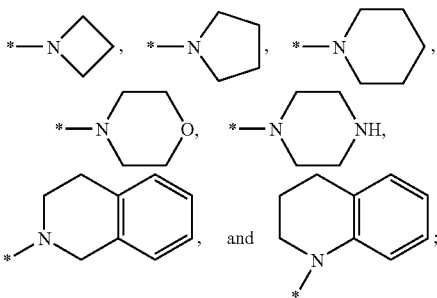

wherein the ring is optionally substituted with a phenyl, is optionally substituted with 1 or 2-$C_{1-4}$ alkyl groups, and is optionally substituted with an oxo, with the proviso that the optional oxo substituent is attached to a carbon atom in the saturated heterocyclic ring.

A twenty-fifth embodiment of the present invention is a compound of Formula I, or a pharmaceutically acceptable salt thereof, wherein:

each CycA is independently a $C_{3-8}$ cycloalkyl which is:
(i) optionally substituted with from 1 to 4 substituents each of which is independently —$C_{1-4}$ alkyl, —OH, —O—$C_{1-4}$ alkyl, or —$C_{1-4}$ haloalkyl, and
(ii) optionally substituted with AryB, HetB, CycB, or $C_{1-4}$ alkyl substituted with CycB, AryB, or HetB;

each AryA is independently phenyl or naphthyl, wherein the phenyl or naphthyl is
(i) optionally substituted with from 1 to 3 substituents each of which is independently halogen, —$C_{1-4}$ alkyl, —O—$C_{1-4}$ alkyl, —$C_{1-4}$ fluoroalkyl, —CN, —$CO_2$H, —$CO_2$—$C_{1-14}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, and
(ii) optionally substituted with AryB, HetB, CycB, —C(O)NH-CycB, —C(O)N($C_{1-4}$ alkyl)-CycB, or $C_{1-4}$ alkyl substituted with CycB, AryB, or HetB;

each HetA is independently (i) a 5- or 6-membered heteroaromatic ring containing from 1 to 3 heteroatoms independently selected from zero to 3 N atoms, zero or 1 O atom, and zero or 1 S atom, wherein each N is optionally in the form of an oxide, or (ii) a 9- or 10-membered bicyclic, fused ring system containing from 1 to 3 heteroatoms independently selected from zero to 3 N atoms, zero or 1 O atom and zero or 1 S atom, wherein either one or both of the rings contain one or more of the heteroatoms, at least one ring is aromatic, each N is optionally in the form of an oxide, and each S in a ring which is not aromatic is optionally S(O) or S(O)$_2$; wherein the heteroaromatic ring or the bicyclic, fused ring system is:
(i) optionally substituted with from 1 to 4 substituents each of which is independently halogen, —$C_{1-4}$ alkyl, or —OH; and
(ii) optionally substituted with AryB, HetB, CycB, or —$C_{1-4}$ alkyl substituted with AryB, HetB or CycB;

each AryB is independently phenyl which is optionally substituted with from 1 to 3 substituents each of which is independently halogen, —$C_{1-4}$ alkyl, —O—$C_{1-4}$ alkyl, —$C_{1-4}$ fluoroalkyl, —CN, —$CO_2$H, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-14}$ alkyl)C(O)—$C_{1-4}$ alkyl;

each HetB is independently a 5- or 6-membered heteroaromatic ring containing from 1 to 3 heteroatoms independently selected from zero to 3 N atoms, zero or 1 O atom, and zero or 1 S atom, wherein the heteroaromatic ring is optionally substituted with from 1 to 4 substituents each of which is independently halogen, —$C_{1-4}$ alkyl, or —OH;

each CycB is independently a $C_{3-6}$ cycloalkyl which is optionally substituted with from 1 to 4 substituents each of which is independently —$C_{1-6}$ alkyl, —OH, or —O—$C_{1-6}$ alkyl;

HetC is a 4- to 7-membered saturated heterocyclic ring containing from 1 to 3 heteroatoms independently selected from 1 to 3 N atoms, zero or 1 O atom, and zero or 1 S atom, wherein the heterocyclic ring is optionally substituted with from 1 to 4 substituents each of which is independently —$C_{1-6}$ alkyl or oxo;

and all other variables are as originally defined or as defined in any one of the preceding embodiments.

A twenty-sixth embodiment of the present invention is identical to the twenty-fifth embodiment, except that each AryA is independently phenyl or naphthyl, wherein the phenyl or naphthyl is
(i) optionally substituted with from 1 to 3 substituents each of which is independently halogen, —$C_{1-4}$ alkyl, —O—$C_{1-4}$ alkyl, —$C_{1-4}$ fluoroalkyl, —CN, —$CO_2$H, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, and
(ii) optionally substituted with AryB, HetB, CycB, or $C_{1-4}$ alkyl substituted with CycB, AryB, or HetB.

A twenty-seventh embodiment of the present invention is a compound of Formula I, or a pharmaceutically acceptable salt thereof, wherein:

each CycA is independently a $C_{3-6}$ cycloalkyl;

each AryA is independently phenyl which is:
  (i) optionally substituted with from 1 to 3 substituents each of which is independently halogen, —$C_{1-4}$ alkyl, —O—$C_{1-4}$ alkyl, —$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-14}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, and
  (ii) optionally substituted with —C(O)NH—$C_{3-6}$ cycloalkyl or —C(O)N($C_{1-4}$ alkyl)-$C_{3-6}$ cycloalkyl;

each HetA is independently a 5- or 6-membered heteroaromatic ring containing from 1 to 3 heteroatoms independently selected from zero to 3 N atoms, zero or 1 O atom, and zero or 1 S atom, wherein the ring is optionally fused with a benzene ring and wherein the optionally fused heteroaromatic ring is optionally substituted with from 1 to 3 substituents each of which is independently —$C_{1-4}$ alkyl or —OH;

and all other variables are as originally defined or as defined in any one of the preceding embodiments.

A twenty-eighth embodiment of the present invention is identical to the twenty-seventh embodiment, except that each AryA is independently phenyl which is optionally substituted with from 1 to 3 substituents each of which is independently halogen, —$C_{1-4}$ alkyl, —O—$C_{1-4}$ alkyl, —$C_{1-4}$ fluoroalkyl, —CN, —$CO_2H$, —$CO_2$—$C_{1-4}$ alkyl, —$SO_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl.

A twenty-ninth embodiment of the present invention is a compound of Formula I, or a pharmaceutically acceptable salt thereof, wherein n is zero; and all other variables are as originally defined or as defined in any one of the preceding embodiments. It is understood that when n is zero, Z forms a direct bond with the carbon to which $R^3$ and $R^4$ are attached, forming thereby a six-membered ring, depicted as follows:

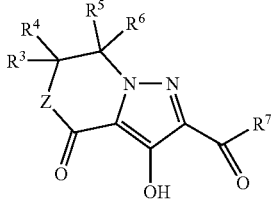

(II)

A thirtieth embodiment of the present invention is a compound of Formula I, or a pharmaceutically acceptable salt thereof, wherein n is 1; and all other variables are as originally defined or as defined in any one of the preceding embodiments.

A thirty-first embodiment of the present invention is a compound of Formula I, or a pharmaceutically acceptable salt thereof, wherein $R^7$ is $N(R^U)R^V$; $R^U$ is H or $C_{1-6}$ alkyl; and $R^V$ is $C_{1-6}$ alkyl substituted with AryA or HetA; and all other variables are as originally defined or as defined in any one of the preceding embodiments. In an aspect of this embodiment, $R^U$ is H or $C_{1-4}$ alkyl; and $R^V$ is $C_{1-4}$ alkyl substituted with AryA or HetA. In another aspect of this embodiment, $R^U$ is H or $C_{1-4}$ alkyl; and $R^V$ is $(CH_2)_{1-2}$-AryA, $(CH_2)_{1-2}$-HetA, CH($CH_3$)-AryA, or CH($CH_3$)-HetA. In another aspect of this embodiment, $R^U$ is H or $CH_3$; and $R^V$ is $(CH_2)_{1-2}$-AryA or CH($CH_3$)-AryA. In still another aspect of this embodiment, $R^U$ is H or $CH_3$; and $R^V$ is $CH_2$-AryA. In a feature of each of the preceding aspects, $R^U$ is H.

A first class of the present invention includes compounds of Formula I, and pharmaceutically acceptable salts thereof, wherein Z is O or N($R^8$); $R^1$ and $R^2$ are as defined in the third embodiment; $R^3$, $R^4$, $R^5$ and $R^6$ are as defined in the seventh embodiment; $R^7$ is as defined in the thirteenth embodiment; $R^8$ is as defined in the fifteenth embodiment; $R^A$ and $R^B$ are as defined in the eighteenth embodiment; $R^C$ and $R^D$ are as defined in the twentieth embodiment; $R^U$ and $R^V$ are as defined in the twenty-second embodiment; CycA, AryA and HetA are as defined in the twenty-fifth embodiment; and n is an integer equal to zero or 1. A sub-class of the first class includes compounds of Formula I, and pharmaceutically acceptable salts thereof, wherein n is zero; and all other variables are as defined in the first class. Another sub-class of the first class includes compounds of Formula I, and pharmaceutically acceptable salts thereof, wherein n is 1; and all other variables are as defined in the first class. Another sub-class of the first class includes compounds of Formula I, and pharmaceutically acceptable salts thereof, wherein $R^7$ is $N(R^U)R^V$; $R^U$ is H or $C_{1-4}$ alkyl; and $R^V$ is $C_{1-4}$ alkyl substituted with AryA or HetA; and all other variables are as defined in the first class or in any of the preceding sub-classes thereof.

A second class of the present invention and sub-classes thereof are identical to the first class and its sub-classes, except that CycA, AryA and HetA are as defined in the twenty-sixth embodiment.

A third class of the present invention includes compounds of Formula I, and pharmaceutically acceptable salts thereof, wherein Z is O or N($R^8$); $R^1$ and $R^2$ are as defined in the fourth embodiment; $R^3$, $R^4$, $R^5$ and $R^6$ are as defined in the eighth embodiment; $R^7$ is as defined in the fourteenth embodiment; $R^8$ is as defined in the sixteenth embodiment; $R^C$ and $R^D$ are as defined in the twenty-first embodiment; $R^U$ and $R^V$ are as defined in the twenty-third embodiment; CycA, AryA and HetA are as defined in the twenty-seventh embodiment; and n is an integer equal to zero or 1. A sub-class of the third class includes compounds of Formula I, and pharmaceutically acceptable salts thereof, wherein n is zero; and all other variables are as defined in the third class. Another sub-class of the third class includes compounds of Formula I, and pharmaceutically acceptable salts thereof, wherein n is 1; and all other variables are as defined in the third class. Another sub-class of the third class includes compounds of Formula I, and pharmaceutically acceptable salts thereof, wherein $R^7$ is $N(R^U)R^V$; $R^U$ is H or $C_{1-4}$ alkyl; and $R^V$ is $(CH_2)_{1-2}$-AryA, $(CH_2)_{1-2}$-HetA, CH($CH_3$)-AryA, or CH($CH_3$)-HetA; and all other variables are as defined in the third class or in any of the preceding sub-classes thereof.

A fourth class of the present invention and sub-classes thereof are identical to the third class and its sub-classes, except that CycA, AryA and HetA are as defined in the twenty-eighth embodiment.

A fifth class of the present invention includes compounds of Formula I, and pharmaceutically acceptable salts thereof, wherein Z is N($R^8$);$R^1$ and $R^2$ are each independently H or $C_{1-4}$ alky; $R^3$, $R^4$, $R^5$ and $R^6$ are as defined in the ninth embodiment; $R^7$ is as defined in the fourteenth embodiment; $R^8$ is as defined in the seventeenth embodiment; $R^C$ and $R^D$ are as defined in the twenty-first embodiment; $R^U$ and $R^V$ are as defined in the twenty-fourth embodiment; CycA, AryA and HetA are as defined in the twenty-seventh embodiment; and n is an integer equal to zero or 1. A sub-class of the fifth class includes compounds of Formula I, and pharmaceutically acceptable salts thereof, wherein n is zero; and all other variables are as defined in the fifth class. Another sub-class of the fifth class includes compounds of Formula I, and pharmaceutically acceptable salts thereof, wherein n is 1; and all other variables are as defined in the fifth class. Another subclass of the fifth class includes compounds of Formula I, and pharmaceutically acceptable salts thereof, wherein $R^7$ is $N(R^U)R^V$; $R^U$ is H or $C_{1-4}$ alkyl; and $R^V$ is $CH_2$-AryA or $CH_2$-HetA; and all other variables are as defined in the fifth class or in any of the preceding sub-classes thereof.

A sixth class of the present invention and sub-classes thereof are identical to the fifth class and its sub-classes, except that CycA, AryA and HetA are as defined in the twenty-eighth embodiment.

A seventh class of the present invention includes compounds of Formula I, and pharmaceutically acceptable salts thereof, wherein Z is $N(R^8)$;

$R^1$ and $R^2$ are both H;

$R^3$, $R^4$, $R^5$ and $R^6$ are defined as follows:

(A) $R^3$ is H; $R^4$ is H or methyl; $R^6$ is H or methyl; and $R^5$ is H, $C_{1-3}$ alkyl, $(CH_2)_{1-2}NH_2$, $(CH_2)_{1-2}NH(C_{1-3}$ alkyl), $(CH_2)_{1-2}N(C_{1-3}$ alkyl$)_2$,

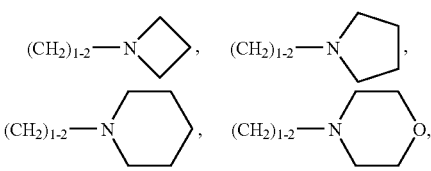

$C(O)NH_2$, $C(O)NH(C_{1-3}$ alkyl), $C(O)N(C_{1-3}$ alkyl$)_2$,

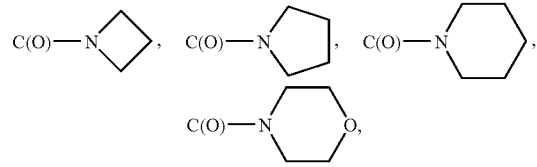

phenyl optionally substituted with 1 or 2 substituents independently selected from halogen and CN, benzyl, or a heteroaromatic ring selected from the group consisting of pyrrolyl, pyrazolyl, imidazolyl, oxazolyl, thiazolyl, triazolyl, oxadiazolyl, thiadiazolyl, pyridinyl, pyrimidinyl, and pyrazinal, wherein the heteroaromatic ring is optionally substituted with 1 or 2 substituents each of which is independently methyl, ethyl, n-propyl, or iso-propyl;

(B) $R^4$ and $R^5$ are each defined as in Part (A) above; and $R^3$ and $R^6$ together form a direct bond resulting in a carbon-carbon double bond; or (C) $R^4$ and $R^5$ together with the carbon atoms to which they are attached form a benzene ring; and $R^3$ and $R^6$ are both absent;

$R^7$ is:

(1) $O-C_{1-3}$ alkyl, (2) $NH_2$, (3) $NH(C_{1-4}$ alkyl),

-continued (4) $N(C_{1-4}$ alkyl$)_2$, (5) $NHCH_2C(O)NH(C_{1-4}$ alkyl), (6) $NHCH_2C(O)N(C_{1-4}$ alkyl$)_2$, (7) *—N☐ , (8) *—N⬠ optionally substituted with phenyl, (9) *—N⬡ ,

(10) *—N⬡O ,

(11) *—N(tetrahydroisoquinoline) ,

(12) $NHCH_2CH_2$—N☐ ,

(13) $NHCH_2CH_2$—N⬠ ,

(14) $NHCH_2CH_2$—N⬡ ,

(15) $NHCH_2CH_2$—N⬡O ,

(16) $NH$—☐—$NH$ ,

(17) $NH$—⬠—$NH$ ,

(18) $NH$—⬡—$NH$ ,

(19) *—N(CH_2CH_2-D)(CH_2-phenyl)

wherein D is OH, $NH_2$, $NH(C_{1-3}$ alkyl), or $N(C_{1-3}$ alkyl$)_2$,

(20) $NH$—$CH_2$-phenyl or $N(CH_3)$—$CH_2$-phenyl, where the phenyl is:

(i) optionally substituted with 1 or 2 substituents each of which is independently bromo, chloro, fluoro, $C_{1-3}$ alkyl, $CF_3$, $C(O)NH_2$, $C(O)NH(C_{1-3}$ alkyl), $C(O)N(C_{1-3}$ alkyl$)_2$, $SO_2CH_3$, or $SO_2CH_2CH_3$, and (ii) optionally substituted with $C(O)NH$-cyclopropyl or $C(O)N(CH_3)$-cyclopropyl, or

(21) NH-E or N(CH₃)-E, where E is:

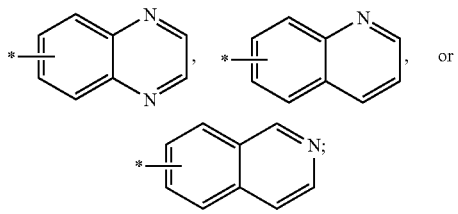

R⁸ is:

(1) H, (2) $C_{1-3}$ alkyl, (3) 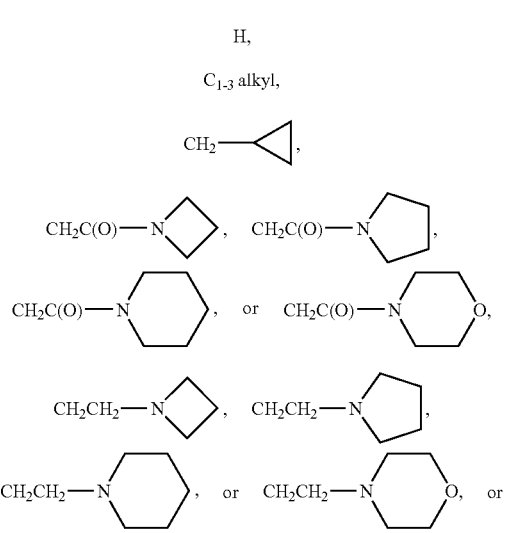

(4)

(5)

(6) $CH_2$-phenyl, where the phenyl is optionally substituted with 1 or 2 substituents each of which is independently bromo, chloro, fluoro, $C_{1-3}$ alkyl, $CF_3$, $C(O)NH_2$, $C(O)NH(C_{1-3}$ alkyl), $C(O)N(C_{1-3}$ alkyl)$_2$, $SO_2CH_3$, or $SO_2CH_2CH_3$; and n is an integer equal to zero or 1. A sub-class of the seventh class includes compounds and pharmaceutically acceptable salts thereof in which n is zero. Another sub-class includes compounds and pharmaceutically acceptable salts thereof in which n is 1. Still another sub-class of the seventh class includes compounds of Formula I and pharmaceutically acceptable salts thereof, wherein R⁷ is:

(1) NH—$CH_2$-phenyl or N(CH₃)—$CH_2$-phenyl, where the phenyl is: (i) optionally substituted with 1 or 2 substituents each of which is independently bromo, chloro, fluoro, $C_{1-3}$ alkyl, $CF_3$, $C(O)NH_2$, $C(O)NH(C_{1-3}$ alkyl), $C(O)N(C_{1-3}$ alkyl)$_2$, $SO_2CH_3$, or $SO_2CH_2CH_3$, and (ii) optionally substituted with $C(O)NH$-cyclopropyl or $C(O)N(CH_3)$-cyclopropyl, or (2) NH-E or N(CH₃)-E, where E is:

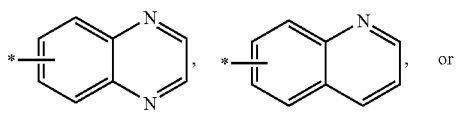

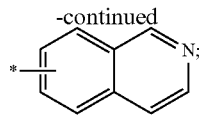

and all other variables are as defined in the seventh class or in any of its preceding sub-classes.

An eighth class and sub-classes thereof are identical to the seventh class and its sub-classes, except that:

R⁵ in Part (A) is H, methyl, $(CH_2)_{1-2}NH_2$, $(CH_2)_{1-2}NH(C_{1-3}$ alkyl), $(CH_2)_{1-2}N(C_{1-3}$ alkyl)$_2$,

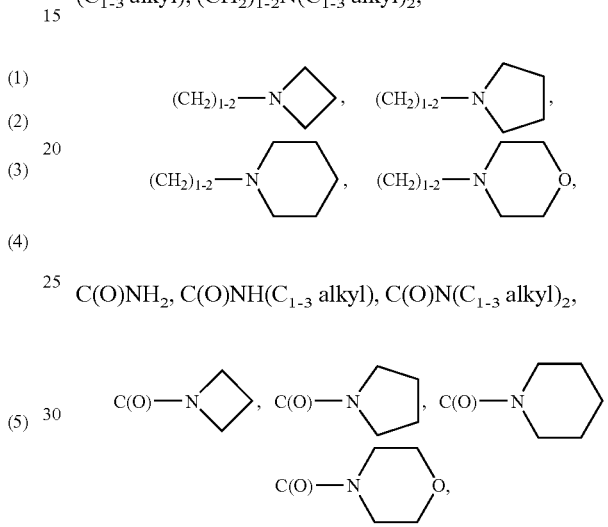

$C(O)NH_2$, $C(O)NH(C_{1-3}$ alkyl), $C(O)N(C_{1-3}$ alkyl)$_2$, phenyl, benzyl, or a heteroaromatic ring selected from the group consisting of pyrrolyl, pyrazolyl, imidazolyl, oxazolyl, thiazolyl, triazolyl, oxadiazolyl, thiadiazolyl, pyridinyl, pyrimidinyl, and pyrazinal, wherein the heteroaromatic ring is optionally substituted with 1 or 2 substituents each of which is independently methyl, ethyl, n-propyl, or isopropyl; and Part (20) in the definition of R⁷ is NH—$CH_2$-phenyl or N(CH₃)—$CH_2$-phenyl, where the phenyl is optionally substituted with 1 or 2 substituents each of which is independently bromo, chloro, fluoro, $C_{1-3}$ alkyl, $CF_3$, $C(O)NH_2$, $C(O)NH(C_{1-3}$ alkyl), $C(O)N(C_{1-3}$ alkyl)$_2$, $SO_2CH_3$, or $SO_2CH_2CH_3$.

A ninth class of the present invention includes compounds of Formula I, and pharmaceutically acceptable salts thereof, wherein Z is N(R⁸);

R¹ and R² are both H;

R³ is H; R⁶ is H or methyl; or alternatively R³ and R⁶ together form a direct bond resulting in a carbon-carbon double bond;

R⁴ is H or methyl;

R⁵ is H, methyl, isopropyl,

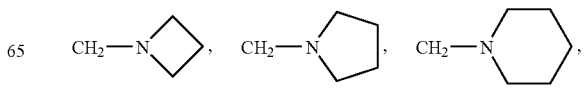

-continued

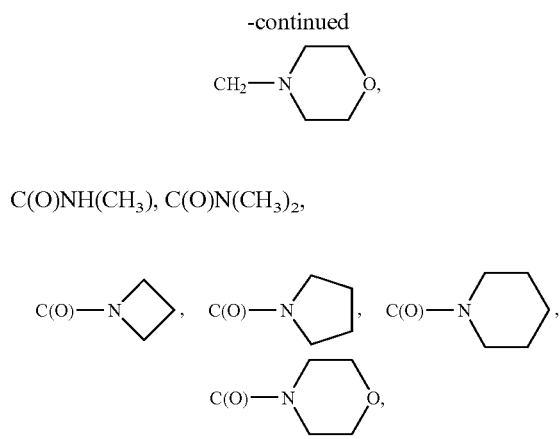

C(O)NH(CH₃), C(O)N(CH₃)₂, phenyl optionally substituted with Br or Cl or F or CN, pyridinyl, or thiazolyl optionally substituted with methyl;

$R^7$ is:

(1) OCH₃, (2) NH(CH₃), (3) N(CH₃)₂, (4) NH(CH₂CH₂CH₂CH₃), (5) NHCH₂C(O)N(CH₃)₂, (6) *—N⟨azetidinyl⟩, (7) *—N⟨pyrrolidinyl⟩ optionally substituted with phenyl, (8) *—N⟨piperidinyl⟩, (9) *—N⟨morpholinyl⟩,

(10) *—N⟨tetrahydroisoquinolinyl⟩,

(11) NHCH₂CH₂—N⟨azetidinyl⟩,

(12) NHCH₂CH₂—N⟨pyrrolidinyl⟩,

(13) NHCH₂CH₂—N⟨piperidinyl⟩,

(14) NHCH₂CH₂—N⟨morpholinyl⟩,

(15) NH⟨azetidinyl-NH₂⟩,

(16) NH⟨pyrrolidinyl-NH₂⟩,

-continued

(17) NH⟨piperidinyl-NH⟩,

(18) *—N(CH₂CH₂OH)(CH₂phenyl),

(19) *—N(CH₂CH₂N(CH₃)₂)(CH₂phenyl),

(20) NH—CH₂-phenyl or N(CH₃)—CH₂-phenyl, where the phenyl is optionally substituted with 4-fluoro, 3,4-dichloro, 2-((methylamino)carbonyl)-4-fluoro, 2-(methylsulfonyl)-4-fluoro, 2-((cyclopropylamino)carbonyl)-4-fluoro, 2-((dimethylamino)carbonyl-4-fluoro, 2-((ethylamino)carbonyl)-4-fluoro, or 2-aminocarbonyl-4-fluoro, or (21)

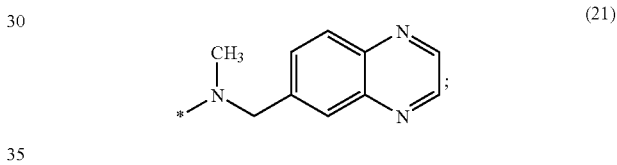

$R^8$ is methyl or p-fluorobenzyl; and n is an integer equal to zero or 1. A sub-class of the ninth class includes compounds and pharmaceutically acceptable salts thereof in which n is zero. Another sub-class includes compounds and pharmaceutically acceptable salts thereof in which n is 1. Still another sub-class of the ninth class includes compounds of Formula I and pharmaceutically acceptable salts thereof, wherein $R^7$ is NH—CH₂-phenyl or N(CH₃)—CH₂-phenyl, where the phenyl is optionally substituted with 4-fluoro, 3,4-dichloro, 2-((methylamino)carbonyl)-4-fluoro, 2-(methylsulfonyl)-4-fluoro, 2-((cyclopropylamino)carbonyl)-4-fluoro, 2-((dimethylamino)carbonyl-4-fluoro, 2-((ethylamino)carbonyl)-4-fluoro, or 2-aminocarbonyl-4-fluoro; and all other variables are as defined in the ninth class or in any of its preceding sub-classes.

A tenth class and sub-classes thereof are identical to the ninth class and its sub-classes, except that:

$R^5$ is H, methyl,

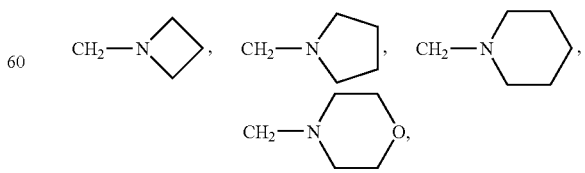

C(O)NH(CH₃), C(O)N(CH₃)₂,

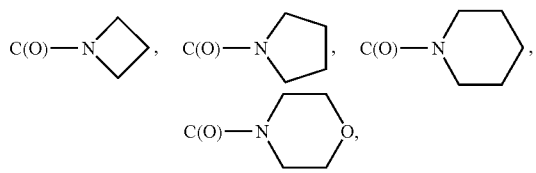

phenyl, pyridinyl, or thiazolyl optionally substituted with methyl; and

Part (20) in the definition of R$^7$ is NH—CH$_2$-phenyl or N(CH$_3$)—CH$_2$-phenyl, where the phenyl is optionally substituted with 4-fluoro, 3,4-dichloro, 2-((methylamino)carbonyl)-4-fluoro, or 2-(methylsulfonyl)-4-fluoro.

Another embodiment of the present invention is a compound, or a pharmaceutically acceptable salt thereof, selected from the group consisting of the compounds set forth in Examples 1 to 49 below.

Another embodiment of the present invention is a compound of Formula I, or a pharmaceutically acceptable salt thereof, as originally defined or as defined in any of the foregoing embodiments, classes, sub-classes, aspects, or features, wherein the compound or its salt is substantially pure. As used herein "substantially pure" means that the compound or its salt is present (e.g., in a product isolated from a chemical reaction or a metabolic process) in an amount of at least about 90 wt. % (e.g., from about 95 wt. % to 100 wt. %), preferably at least about 95 wt. % (e.g., from about 98 wt. % to 100 wt. %), more preferably at least about 99 wt. %, and most preferably 100 wt. %. The level of purity of the compounds and salts can be determined using standard methods of analysis. A compound or salt of 100% purity can alternatively be described as one which is free of detectable impurities as determined by one or more standard methods of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an HIV infection/AIDS treatment/prophylaxis agent selected from the group consisting of HIV/ADS antiviral agents, immunomodulators, and anti-infective agents.

(d) The pharmaceutical composition of (c), wherein the HIV infection/AIDS agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an HIV infection/AIDS treatment/prophylaxis agent selected from the group consisting of HIV/AIDS antiviral agents, immunomodulators, and anti-infective agents; wherein the compound of Formula I and the HIV infection/AIDS treatment/prophylaxis agent are each employed in an amount that renders the combination effective for inhibiting HIV integrase, for treating or preventing infection by HIV, or for preventing, treating or delaying the onset of AIDS.

(f) The combination of (e), wherein the HIV infection/AIDS treatment/prophylaxis agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method of preventing or treating infection by HIV in a subject in need thereof which comprises administering to the subject an effective amount of a compound of Formula I.

(i) The method of (h), wherein the compound of Formula (I) is administered in combination with an effective amount of at least one antiviral selected from the group consisting of HIV protease inhibitors, non-nucleoside HIV reverse transcriptase inhibitors, and nucleoside HIV reverse transcriptase inhibitors.

j) A method of preventing, treating or delaying the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment/prophylaxis agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt. stopped here As used herein, the term "alkyl" refers to any linear or branched chain alkyl group having a number of carbon atoms in the specified range. Thus, for example, "C$_{1-6}$ alkyl" (or "C$_1$-C$_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (i.e., a bivalent alkane radical, or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "C(O)" appearing in the definition of a functional group (e.g., "C(O)$R^A$") refers to carbonyl. The terms "S(O)$_2$" and "SO$_2$" appearing in the definition of a functional group each refer to sulfonyl, and the term "S(O)" refers to sulfinyl.

The symbols "*" and "⌇" at the end of a bond each refer to the point of attachment of a functional group or other chemical moiety to the rest of the molecule of which it is a part.

The term "aryl" refers to (i) phenyl or (ii) a 9- or 10-membered bicyclic, fused carbocylic ring system in which at least one ring is aromatic. A class of aryls suitable for use in the present invention is phenyl, naphthyl, and indenyl. Another class of suitable aryls is phenyl and naphthyl. A particularly suitable aryl is phenyl.

The term "heteroaryl" refers to (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$. Suitable heteroaryls include, for example, pyridinyl, pyrrolyl, pyrazinyl, pyrimidinyl, pyridazinyl, triazolyl, thienyl, furanyl, imidazolyl, pyrazolyl, triazolyl, tetrazolyl, oxazolyl, isooxazolyl, oxadiazolyl, quinolinyl, tetrahydroquinolinyl, isoquinolinyl, tetrahydroisoquinolinyl, indolyl, isoindolyl, benzodioxolyl, benzopiperidinyl, benzisoxazolyl, benzoxazolyl, chromenyl, chromanyl, isochromanyl, cinnolinyl, quinazolinyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, 2,3-dihydrobenzo-1,4-dioxinyl (i.e.,

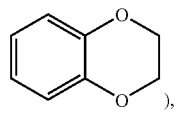

and benzo-1,3-dioxolyl (i.e.,

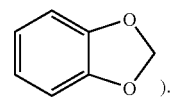

A class of heteroaryls suitable for use in the present invention consists of 5- and 6-membered heteroaromatic rings containing from 1 to 3 heteroatoms independently selected from N, O and S, wherein each N is optionally in the form of an oxide, or (ii) a 9- or 10-membered bicyclic, fused ring system containing from 1 to 3 heteroatoms independently selected from zero to 3 N atoms, zero or 1 O atom and zero or 1 S atom, wherein either one or both of the rings contain one or more of the heteroatoms, at least one ring is aromatic, each N is optionally in the form of an oxide, and each S in a ring which is not aromatic is optionally S(O) or S(O)$_2$. Another class of heteroaryl suitable for use in the present invention consists of heteroaryls as defined in the immediately preceding class, except that the 1 to 3 heteroatoms in either the heteroaromatic ring or the bicyclic, fused ring system are independently selected from 1 to 3 N atoms, zero or 1 O atom and zero or 1 S atom (i.e., the heteroaryl is required to have at least one N atom). Still another class of suitable heteroaryls consists of 5- and 6-membered heteroaromatic ring containing from 1 to 3 heteroatoms independently selected from zero to 3 N atoms, zero or 1 O atom, and zero or 1 S atom, wherein each N atom is optionally in the form of an oxide. Heteroaryls belonging to this class include pyridinyl, pyrrolyl, pyrazinyl, pyrimidinyl, pyridazinyl, triazinyl, furanyl, imidazolyl, pyrazolyl, triazolyl, tetrazolyl, oxazolyl, isooxazolyl, and oxadiazolyl. Still another class of heteroaryl suitable for use in the present invention consists of heteroaryls as defined in the immediately preceding class, except that the 1 to 3 heteroatoms in the 5- or 6-membered heteroaromatic ring are independently selected from 1 to 3 N atoms, zero or 1 O atom and zero or 1 S atom (i.e., the heteroaryl is required to have at least one N atom).

The term "saturated heterocyclic ring" (or saturated heterocyclyl) refers herein to a 4- to 7-membered saturated heterocyclic ring containing from 1 to 4 heteroatoms independently selected from N, O and S. Suitable saturated heterocycles include, for example, azetidinyl, pyrrolidinyl, imidazolinyl, tetrahydrofuranyl, tetrahydrothienyl, pyrazolidinyl, piperidinyl, piperazinyl, hexahydropyrimidinyl, morpholinyl, thiomorpholinyl, thiazolidinyl, isothiazolidinyl, oxazolidinyl, isoxazolidinyl, thiazinanyl, azepanyl, diazepanyl, thiazepanyl, thiadiazepanyl. A class of saturated heterocycles suitable for use in the present invention consists of 4- to 7-membered saturated heterocyclic rings containing from 1 to 3 heteroatoms independently selected from 1 to 3 N atoms, zero or 1 O atom, and zero or 1 S atom.

Unless a contrary meaning is clear in a given context, any of the various aryl groups and heterocyclic groups (including heteroaryls and saturated heterocyclyls) defined herein are attached to the rest of the compound at any ring atom (i.e., any carbon atom or any heteroatom) provided that a stable compound results.

Unless a contrary meaning is clear in a given context, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 5 substituents" is intended to include as aspects thereof, an aryl or heteroaryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 1 substituent, 2 substituents, 3 substituents, 4 substituents, and 5 substituents.

When any variable (e.g., $R^A$, $R^B$, and HetB) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

Mono- and poly-substitution by a named substituent (e.g., as in "is optionally substituted with from 1 to 5 substituents . . . ") is permitted to the extent such single and multiple substitution (including multiple substitution at the same site) is chemically allowed. Unless a contrary meaning is clear in a given context, substitution by a named substituent is permitted on any atom in a ring (e.g., cycloalkyl, aryl, or heteroaryl) provided such ring substitution is chemically allowed and results in a stable compound.

Unless a contrary meaning is clear in a given context, the term "unsaturated ring" refers to a partially or fully unsaturated ring, said ring containing one or more double bonds. For example, a reference to an unsaturated 6-membered carbocyclic ring refers to cyclohexene, cyclohexadiene, and benzene.

In instances where a hydroxy (—OH) substituent(s) is(are) permitted on an unsaturated ring (e.g., a heteroaromatic ring) and keto-enol tautomerism is possible, it is understood that the substituent might in fact be present, in whole or in part, in the keto form, as exemplified here for a hydroxypyridinyl substituent:

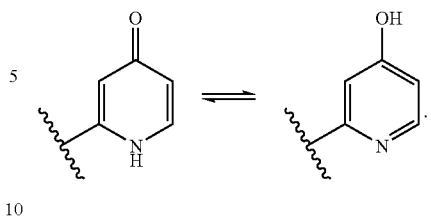

Compounds of the present invention having a hydroxy substituent on a carbon atom of an unsaturated ring in which keto-enol tautomerism is possible are understood to include compounds in which only the hydroxy is present, compounds in which only the tautomeric keto form (i.e., an oxo substituent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether individually or in mixtures, are within the scope of the present invention.

As would be recognized by one of ordinary skill in the art, compounds of the present invention can exist as tautomers, such as the following:

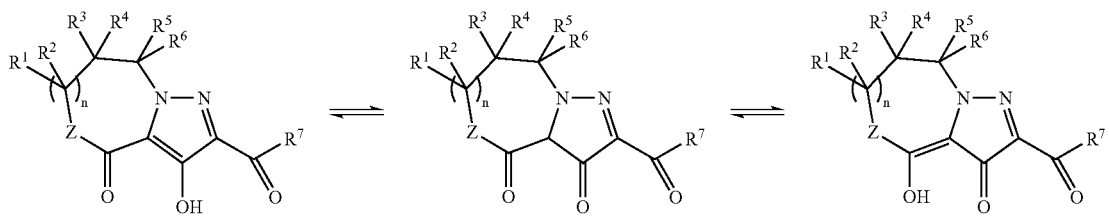

The present invention includes all tautomeric forms, individually and in mixtures.

The compounds of the present inventions are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment or prophylaxis. When a compound of the invention or a prodrug thereof is provided in combination with one or more other active agents (e.g., antiviral agents useful for treating or preventing HIV infection or AIDS), "administration" and its variants are each understood to include provision of the compound or prodrug and other agents at the same time or at different times.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HIV integrase, preventing or treating HIV infection or preventing, treating or delaying the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to the use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, 57th edition, Thomson PDR, 2003. The dosage ranges for a compound of the invention in these combinations are the same as those set forth above. It is understood that pharmaceutically acceptable salts of the compounds of the invention and/or the other agents (e.g., indinavir sulfate) can be used as well.

Abbreviations used in the instant specification, particularly the Schemes and Examples, include the following: AcOH=acetic acid; AIDS=acquired immunodeficiency syndrome; ARC=AIDS related complex; DIEA=diisopropylethylamine (or Hunig's base); DMF=dimethylformamide; DMSO=dimethyl sulfoxide; EDC=1-ethyl-3-(3-dimethylaminopropyl) carbodiimide; ES-MS=electron spray mass spectroscopy; Et=ethyl; EtOAc=ethyl acetate; EtOH=ethanol; FT-ICR=fourier transform ion cyclotron resonance (mass spectroscopy); HIV=human immunodeficiency virus; HOAT=1-hydroxy-7-azabenzotriazole; HOBT or HOBt=1-hydroxy benzotriazole hydrate; HRMS=high resolution mass spectroscopy; i-PrOH=isopropyl alcohol; Me=methyl; MeOH=methanol; NMR=nuclear magnetic resonance; TFA=trifluoroacetic acid; THF=tetrahydrofuran.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Schemes 1 to 8 below provide representative methods for preparing compounds of Formula I of the present invention. A useful starting point for preparation of compounds of the present invention is the pyrazole 1, which itself can be prepared as described in Rodriguez-Franco, et al. *Tetrahedron* 1999, 55: 2763-72). As shown in Scheme 1, alkylation of the pyrazole nitrogen in 1 with 1,2-dibromoethane in the presence of a base such as cesium carbonate provides bromoethyl pyrazole 2. The bromine in 2 can be displaced with azide to give 3. Conversion of the azide to the corresponding primary amine can be accomplished by a variety of methods (e.g., under Staudinger conditions using triphenylphosphine and water), and the primary amine will undergo lactamization with the adjacent ester to give 4. The lactam nitrogen of 4 can be derivatized by alkylation with an alkyl halide in the presence of a base such as sodium hydride to give 5. Alternatively, 5 can be produced directly from bromide 2 by heating the latter in the presence of an amine. Ester 5 can be converted to hydroxy amide 6 in three ways. In one method the benzyl group is first removed by hydrogenolysis using hydrogen gas and a catalyst such as palladium on carbon, and the resulting hydroxy ester is then heated in the presence of an amine to give 6. In a second method the ester is hydrolyzed with a base such as sodium hydroxide, the active ester is coupled with an amine to give the corresponding amide, and then the benzyl group is removed by hydrogenolysis in the presence of hydrogen gas and a catalyst such as palladium on carbon to give 6. A third method is the same as the second method except that in the third and final step, the benzyl group is removed by a dealkylation reaction using a strong acid such as hydrobromic acid to produce 6. 1,4-Diazepine analogs of 6 can be prepared by alkylating 1 with 1,3-dibromopropane instead of 1,2-dibromoethane in step a.

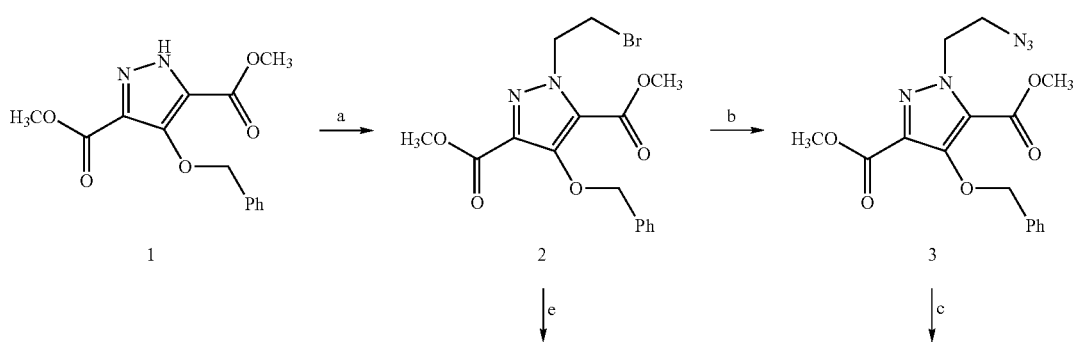

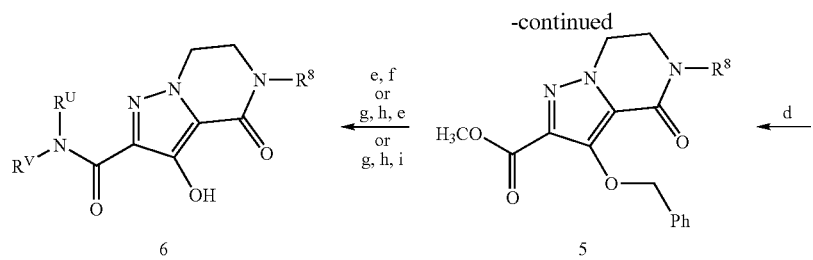

a. dibromoethane, Cs₂CO₃; b. NaN₃; c. Ph₃P, H₂O; d. R⁸—X, NaH; e. R⁸NH₂, heat; e. H₂, Pd—C; f. Rᵁ(Rⱽ)NH, heat; g. NaOH; h. EDC, HOBT, Rᵁ(Rⱽ)NH; i. HBr, HOAc Scheme 2 shows that pyrazole 1 can be alkylated with an alpha-halo nitrile or equivalent reagent to give 7. Reduction of the nitrile in 7 using hydrogen gas and a catalyst such as rhodium on alumina produces the corresponding primary amine which undergoes lactamization to provide 8. The lactam nitrogen in 8 can be alkylated with an alkyl halide in the presence of a base such as sodium hydride to give 9. Transformation of 9 to hydroxy amide 10 can be accomplished in three ways as depicted in Scheme 2 and as described in detail in the text for Scheme 1.

nated to give an amine which undergoes lactamization to 12. Transformation of 12 to hydroxy amide 13 can be accomplished in three ways as indicated in the Scheme and as described in detail in the text for Scheme 1. In a second sequence of reactions, ketone 11 is heated in the presence of an amine to give ene-lactam 14. Transformation of 14 to hydroxy amide 15 can be accomplished in three ways as indicated in the Scheme and as described in detail in the text for Scheme 1. In a third sequence of reactions, ketone 11 is

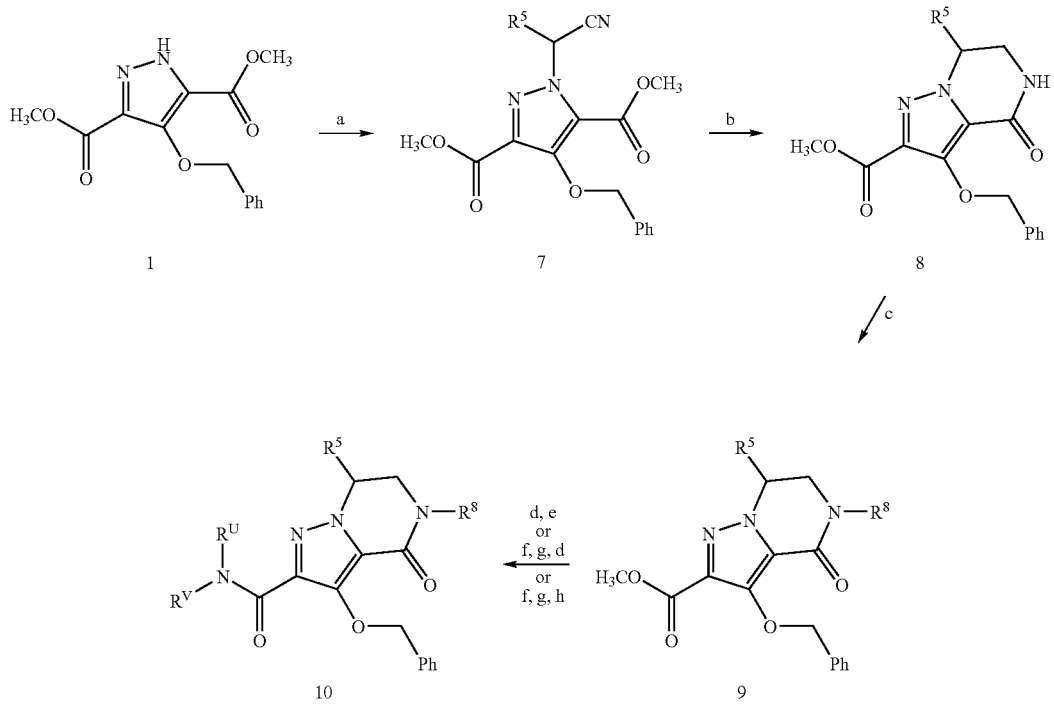

a. alpha-halonitrile, Cs₂CO₃; b. H₂, Rh-alumina; c. NaH, R⁵—X; d. H₂, Pd—C; e. Rᵁ(Rⱽ)NH, heat; f. NaOH; g. Rᵁ(Rⱽ)NH, EDC, HOBT; h. HBr, HOAc Scheme 3 shows the alkylation of pyrazole 1 with an alpha-haloketone or equivalent reagent in the presence of a base such as cesium carbonate gives an intermediate, ketone 11, which can be used to prepare three different types of compounds. In one sequence of reactions, 11 is reductively amireduced with a reagent such as sodium borohydride to give an alcohol which undergoes lactonization to 16. Transformation of 16 to hydroxy amide 17 can be accomplished in three ways as indicated in the Scheme and as described in detail in the text for Scheme 1.

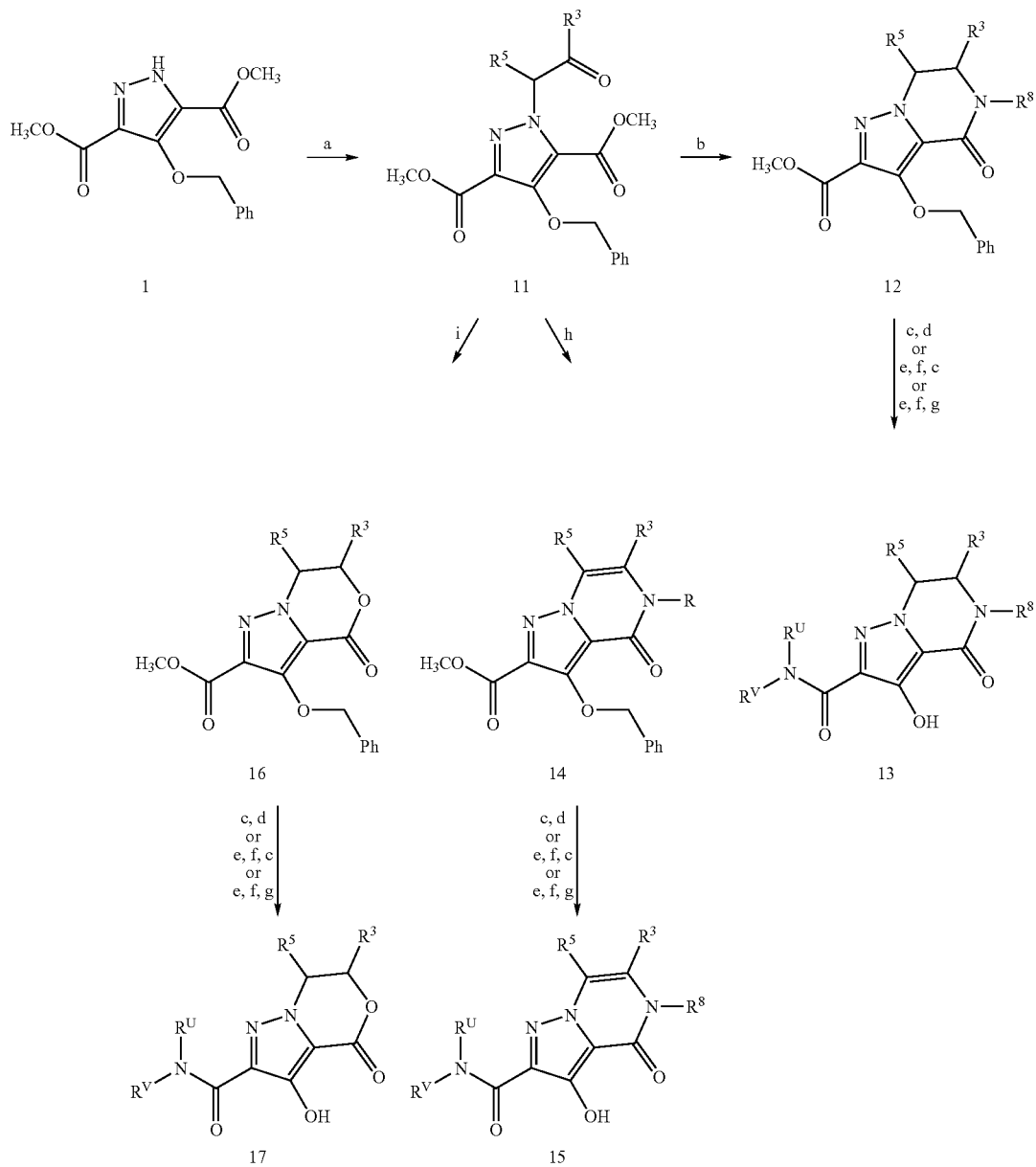

a. alpha-haloketone, Cs₂CO₃; b. R⁸NH₂, NaBH₃CN, heat; c. H₂, Pd—C;
d. R^U(R^V)NH, heat; e. NaOH; f. R^U(R^V)NH, EDC, HOBT; g. HBr, HOAc;
h. R⁸NH₂, heat; i. NaBH₄, heat Scheme 4 depicts the alkylation of pyrazole 1 with a functionalized propionate ester to give 18. Removal of the protecting group on nitrogen in 18 produces an amine which undergoes lactamization to 19. The lactam nitrogen in 19 can be alkylated with an alkyl halide in the presence of a base such as sodium hydride, followed by selective saponification of the ester on the lactam ring to give acid 20. The acid in 20 can be coupled to an amine using standard peptide coupling procedures and then transformation of the resulting amide to hydroxy amide 21 can be accomplished in three ways as indicated in the Scheme and as described in detail in the text for Scheme 1. Alternatively, the lactam nitrogen in 19 can be alkylated with an alkyl halide in the presence of a base such as sodium hydride, and then the lactam ring can be additionally alkylated at the position bearing the ester group using an alkyl halide in the presence of a base such as sodium hydride. Selective saponification of the ester on the lactam ring with a base such as sodium hydroxide gives acid 22. The acid in 22 can be coupled to an amine using standard peptide coupling procedures and then transformation of the resulting amide to hydroxy amide 23 can be accomplished in three ways as indicated in the Scheme and as described in detail in the text for Scheme 1.

Scheme 4

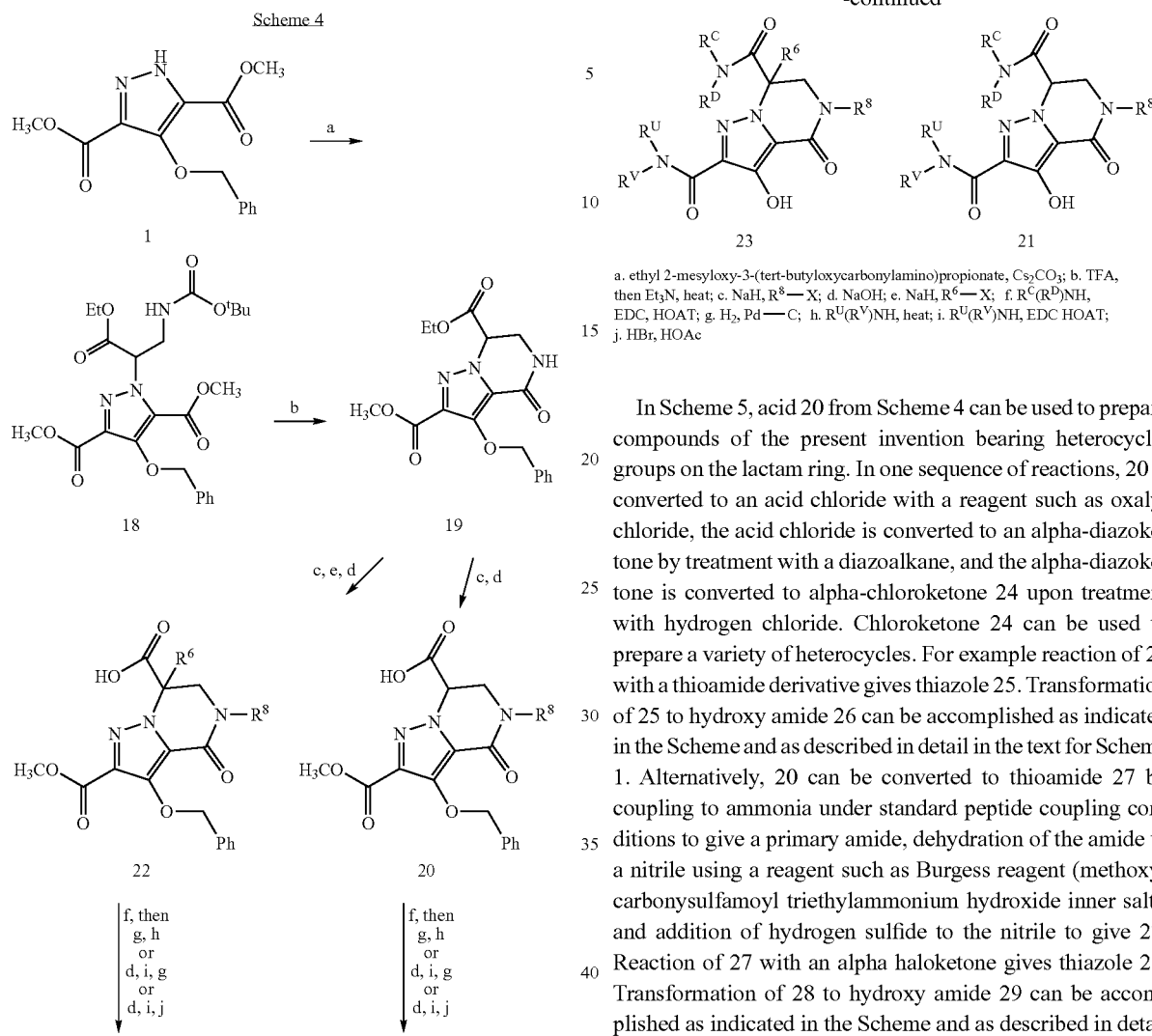

a. ethyl 2-mesyloxy-3-(tert-butyloxycarbonylamino)propionate, Cs$_2$CO$_3$; b. TFA, then Et$_3$N, heat; c. NaH, R$^8$—X; d. NaOH; e. NaH, R$^6$—X; f. R$^C$(R$^D$)NH, EDC, HOAT; g. H$_2$, Pd—C; h. R$^U$(R$^V$)NH, heat; i. R$^U$(R$^V$)NH, EDC HOAT; j. HBr, HOAc In Scheme 5, acid 20 from Scheme 4 can be used to prepare compounds of the present invention bearing heterocyclic groups on the lactam ring. In one sequence of reactions, 20 is converted to an acid chloride with a reagent such as oxalyl chloride, the acid chloride is converted to an alpha-diazoketone by treatment with a diazoalkane, and the alpha-diazoketone is converted to alpha-chloroketone 24 upon treatment with hydrogen chloride. Chloroketone 24 can be used to prepare a variety of heterocycles. For example reaction of 24 with a thioamide derivative gives thiazole 25. Transformation of 25 to hydroxy amide 26 can be accomplished as indicated in the Scheme and as described in detail in the text for Scheme 1. Alternatively, 20 can be converted to thioamide 27 by coupling to ammonia under standard peptide coupling conditions to give a primary amide, dehydration of the amide to a nitrile using a reagent such as Burgess reagent (methoxycarbonysulfamoyl triethylammonium hydroxide inner salt), and addition of hydrogen sulfide to the nitrile to give 27. Reaction of 27 with an alpha haloketone gives thiazole 28. Transformation of 28 to hydroxy amide 29 can be accomplished as indicated in the Scheme and as described in detail in the text for Scheme 1.

Scheme 5

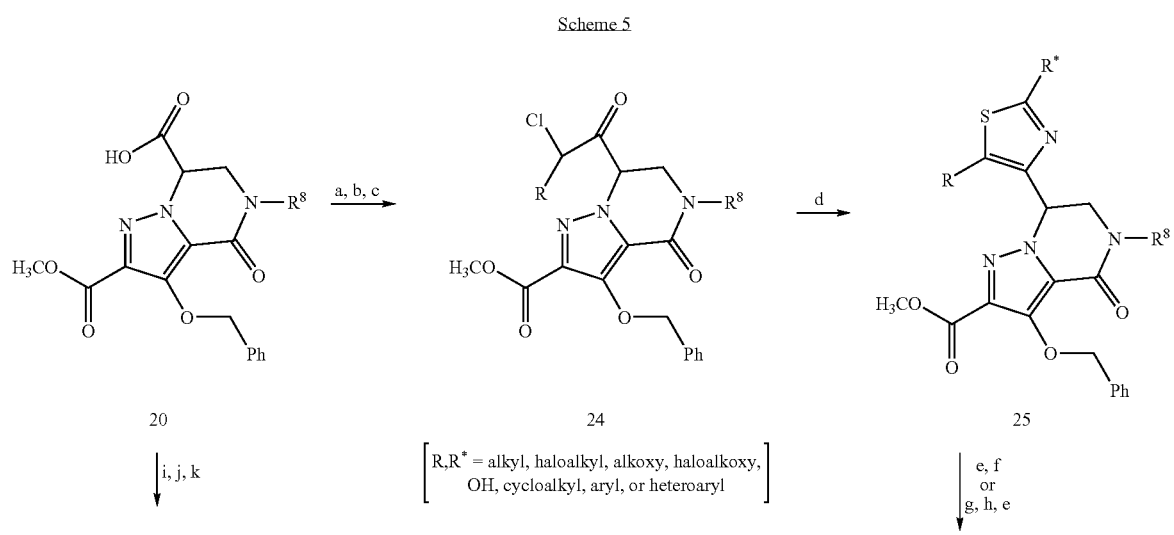

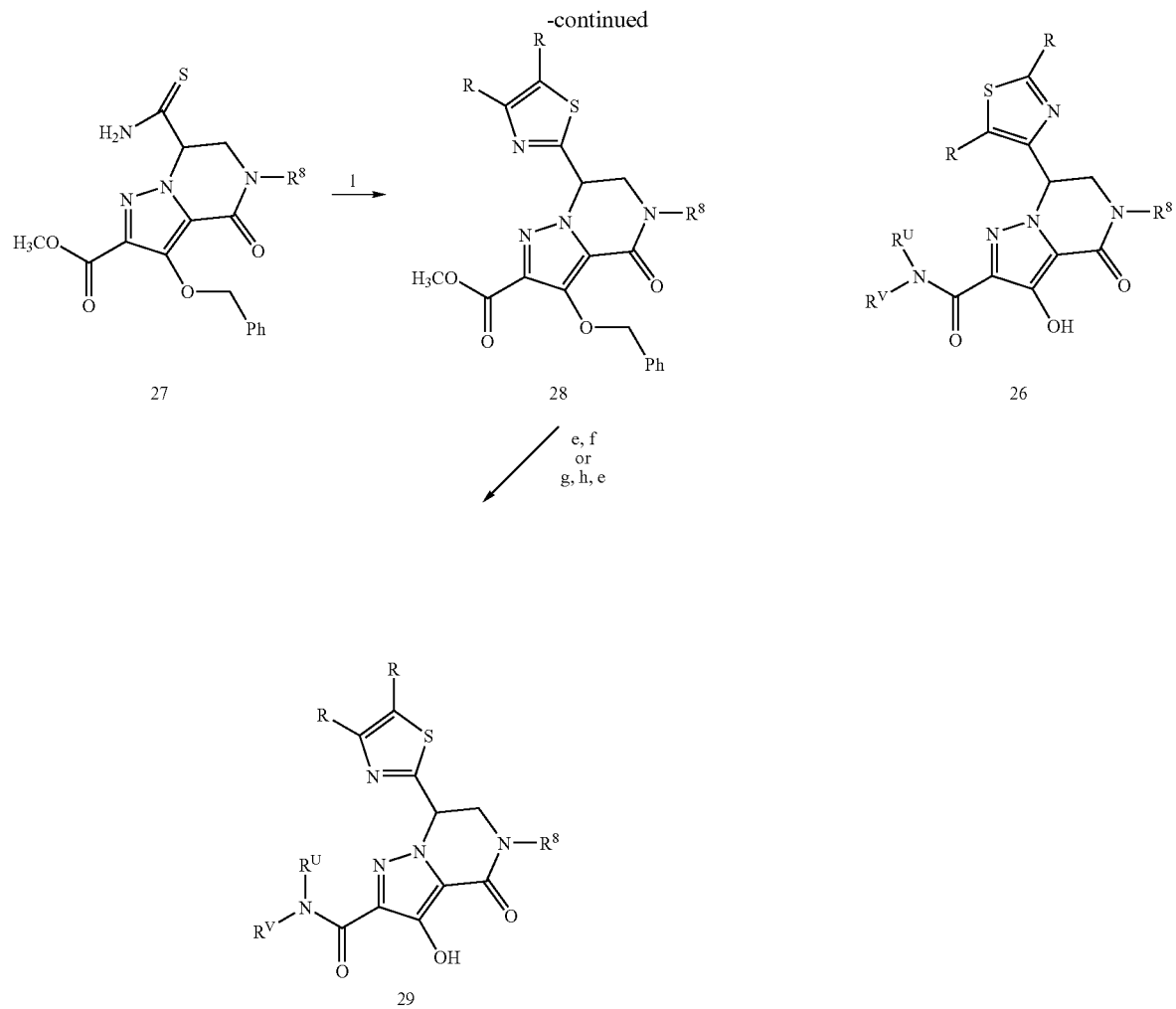

a. oxalyl chloride; b. RCHN₂; c. HCl; d. R*C(S)NH₂, heat; e. HBr, HOAc; f. R^U(R^V)NH, heat; g, NaOH; h. R^U(R^V)NH, EDC, HOBT; i. NH₃, EDC, HOBT; j. Burgess reagent; k. H₂S, pyridine; l. RCH(Cl)COR, heat As shown in Scheme 6, acid 20 from Scheme 4 can be used to prepare amino derivatives. For example, the acid in 20 can be reduced with a reagent such as borane to give an alcohol. The alcohol can be converted to a leaving group such as a mesylate. The mesylate can then be displaced by amines to give 30. Alternatively the mesylate can be displaced using a reagent such as sodium azide to give an alkyl azide. The azide can then be converted to a primary amine using a variety of conditions, including Staudinger conditions using triphenylphosphine and water, to give a primary amine product. The amine can then be reductively alkylated using a carbonyl compound and a reducing agent such as sodium cyanoborohydride to provide 30. Transformation of 30 to hydroxy amide 31 can be accomplished as indicated in the Scheme and as described in detail in the text for Scheme 1.

Scheme 6

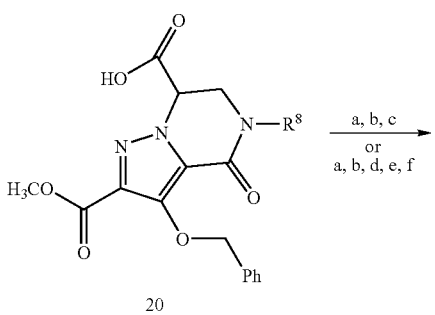

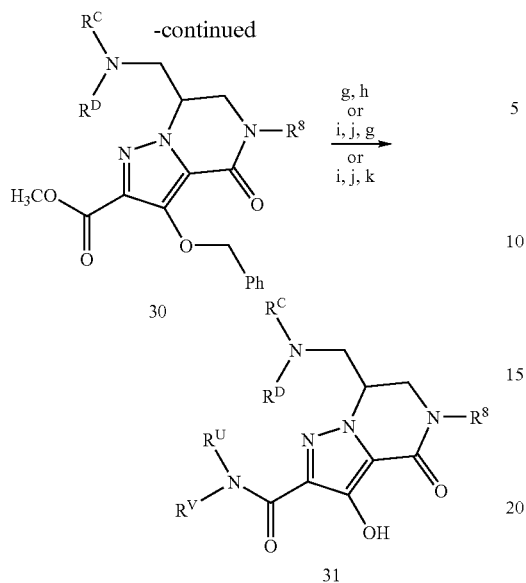

a. BH₃; b. CH₃SO₂Cl, Et₃N; c. R^C(R^D)NH; d. NaN₃; e. Ph₃P, H₂O;
f. R^CCHO, NaBH₃CN; g. H₂, Pd—C; h. R^U(R^V)NH, heat; i. NaOH;
j. R^U(R^V)NH, EDC, HOAT; k. HBr, HOAc As shown in Scheme 7, diester pyrazole 1 can be selectively converted to mono ester, mono acid 32 using dimethylhydrazine. Coupling acid 32 to an amino alcohol derivative using standard peptide coupling conditions gives amide 33. Ring closure of 33 to give 34 can be accomplished using Mitsunobu conditions using reagents such as diethyl azodicarboxylate and triphenylphosphine. Transformation of 34 to hydroxy amide 35 can be accomplished as indicated in the Scheme and as described in detail in the text for Scheme 1.

Scheme 7

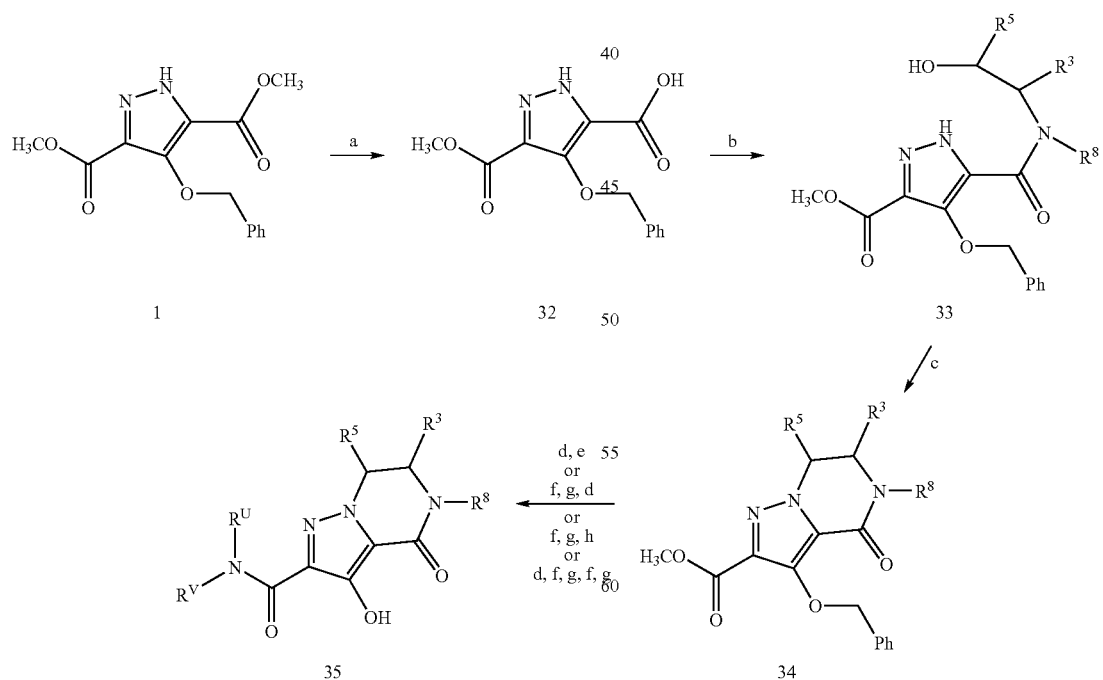

a. 1,1-dimethylhydrazine; b. HN(R⁸)CH(R³)CH(R⁵)OH, EDC, HOAT; c. DEAD, Ph₃P; d, H₂, Pd—C;
e. R^U(R^V)NH, heat; f. NaOH; g, R^U(R^V)NH, EDC, HOAT; h. HBr, HOAc As shown in Scheme 8, the pyrazole nitrogen in 1 can be arylated by reaction with 2-fluoronitrobenze derivatives or equivalent reagents in the presence of a base such as cesium carbonate to give 36. Reduction of the nitro group with hydrogen gas in the presence of a catalyst such as palladium on carbon is followed by lactamization to give 37. The lactam nitrogen in 37 can be alkylated with an alkyl halide in the presence of a base such as sodium hydride to give 38. Transformation of 38 to hydroxy amide 39 can be accomplished as indicated in the Scheme and as described in detail in the text for Scheme 1.

tivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley &

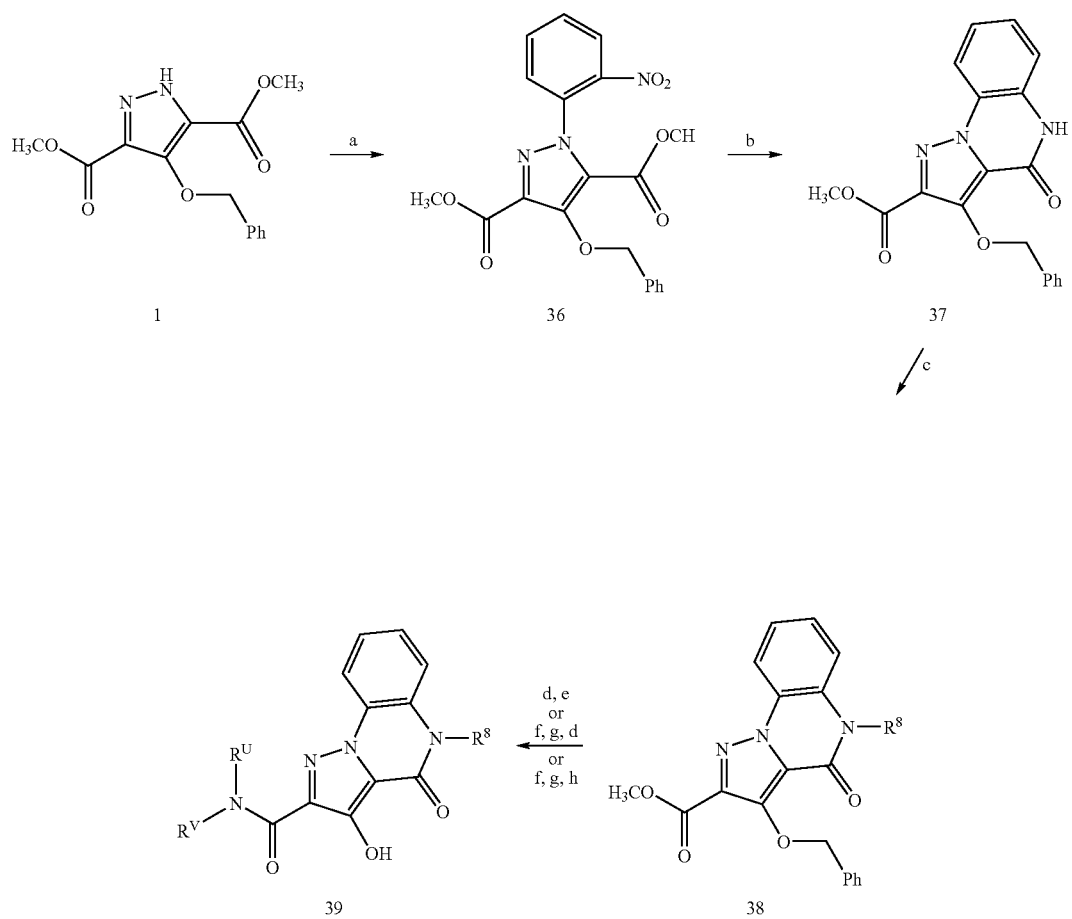

a. $Cs_2CO_3$, 2-fluoro-nitorbenzene; b. $H_2$ Pd—C; heat; c. NaH, $R^8$—X; d, $H_2$, Pd—C; e. $R^U(R^V)NH$, heat; f. NaOH; g, $R^U(R^V)NH$, EDC, HOAT; h. HBr, HOAc In the processes for preparing compounds of the present invention set forth in the foregoing schemes, functional groups in various moieties and substituents may be sensitive or reactive under the reaction conditions employed and/or in the presence of the reagents employed. Such sensitivity/reac- Sons, $3^{rd}$ edition, 1999, and $2^{nd}$ edition, 1991. The protecting groups may be removed at a convenient subsequent stage using methods known in the art. Alternatively the interfering group can be introduced into the molecule subsequent to the reaction step of concern.

The following examples serve only to illustrate the invention and its practice. The examples are not to be construed as limitations on the scope or spirit of the invention.

EXAMPLE 1

Methyl 5-(4-fluorobenzyl)-3-hydroxy-4-oxo-4,5,6,7-tetrahydropyrazolo[1,5-a]pyrazine-2-carboxylate

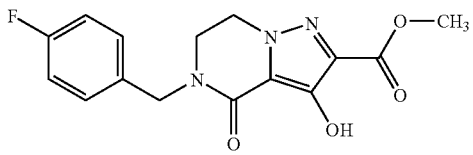

Step 1: Dimethyl 4-benzyloxy-1-(2-bromoethyl)-1H-pyrazole-3,5-dicarboxylate

To a solution of dimethyl 4-benzyloxy-1H-pyrazole-3,5-dicarboxylate (1.0 g, 3.45 mmol) in anhydrous DMF (20 mL) were added $Cs_2CO_3$ (1.35 g, 4.13 mmol) and dibromoethane (2.27 g, 12.1 mmol). The reaction mixture was stirred at room temperature for 2 hours and then filtered. The filtrate was concentrated in vacuo and the residue was purified by flash chromatography on silica gel using a 0-25% EtOAc/hexanes gradient elution. Collection and concentration of the appropriate fractions provided the title compound as a white solid. $^1$H NMR (400 MHz, $d_6$-DMSO) δ 7.45-7.34 (m, 5H), 5.06 (s, 2H), 4.88 (t, J=6.4 Hz, 2H), 3.86-3.79 (m, 8H).

Step 2: Dimethyl 1-(2-azidoethyl)-4-benzyloxy-1H-pyrazole-3,5-dicarboxylate

To a solution of dimethyl 4-benzyloxy-1-(2-bromoethyl)-1H-pyrazole-3,5-dicarboxylate (1.0 g, 2.52 mmol) in DMF was added sodium azide. The reaction mixture was stirred at 40° C. overnight and quenched with water (100 mL). The mixture was extracted with EtOAc four times, and the organic extracts were washed with brine, dried over $Na_2SO_4$, and concentrated in vacuo. The resulting residue was purified by flash chromatography on silica gel using 0-30% EtOAc/hexanes gradient elution. Collection and concentration of the appropriate fractions afforded the title compound as a white solid. ES MS (M+1)=360.

Step 3: Methyl 3-benzyloxy-4-oxo-4,5,6,7-tetrahydropyrazolo[1,5-a]pyrazine-2-carboxylate To a solution of dimethyl 1-(2-azidoethyl)-4-benzyloxy-1H-pyrazole-3,5-dicarboxylate (0.84 g, 2.34 mmol) in anhydrous DMF at 0° C. was added triphenylphosphine (0.92 g, 3.50 mmol). Water (300 μL) was added and the reaction was heated to 90° C. for 3 days. The solvent was removed in vacuo, and the resulting white solid was purified by flash chromatography on silica gel using 0-10% MeOH/$CHCl_3$ gradient elution. Collection and concentration of the appropriate fractions afforded an oily solid which was triturated with methanol to yield a white precipitate. The solid was collected by vacuum filtration to afford the title product. ES MS (M+1)=302.

Step 4: Methyl 3-benzyloxy-5-(4-fluorobenzyl)-4-oxo-4,5,6,7-tetrahydropyrazolo[1,5-a]pyrazine-2-carboxylate To a solution of methyl 3-benzyloxy-4-oxo-4,5,6,7-tetrahydropyrazolo[1,5-a]pyrazine-2-carboxylate (50 mg, 0.17 mmol) in anhydrous DMF at 0° C. was added NaH (6 mg, 0.25 mmol, 95% dispersion in oil). Once gas evolution had ceased, the mixture was treated with 4-fluorobenzyl bromide (31 μL, 0.25 mmol) and was stirred for 2 hours. The reaction was quenched by the addition of a few drops of water. Purification by reverse phase chromatography on a C-18 column using a gradient elution of 95-5% $H_2O$ (0.1% TFA)/$CH_3CN$ (0.1% TFA) and collection and concentration of the appropriate fractions afforded the title product. ES MS (M+1)=410.

Step 5: Methyl 5-(4-fluorobenzyl)-3-hydroxy-4-oxo-4,5,6,7-tetrahydropyrazolo[1,5-a]pyrazine-2-carboxylate Nitrogen gas was bubbled through a solution of methyl 3-benzyloxy-5-(4-fluorobenzyl)-4-oxo-4,5,6,7-tetrahydropyrazolo[1,5-a]pyrazine-2-carboxylate (37 mg, 0.09 mmol) in MeOH. To the solution was added a small amount of 10% Pd on carbon, and the mixture was stirred under an atmosphere of hydrogen gas overnight. The reaction mixture was filtered through celite, and the filter cake was washed with MeOH. The resulting filtrate was concentrated in vacuo to afford the title compound as a white solid. $^1$H NMR (400 MHz, $d_6$-DMSO) δ 9.20 (s, 1H), 7.41-7.37 (m, 2H), 7.21-7.16 (m, 2H), 4.65 (s, 2H), 4.32 (t, J=6.0 Hz, 2H), 3.79 (s, 3H), 3.69 (t, J=6.0H, 2H). HRMS (FT-ICR) $C_{15}H_{14}FN_3O_4$+H=320.1047; calculated 320.1041.

EXAMPLE 2

N-(4-Fluorobenzyl)-3-hydroxy-5-methyl-4-oxo-7-phenyl-4,5,6,7-tetrahydropyrazolo[1,5-a]pyrazine-2-carboxamide

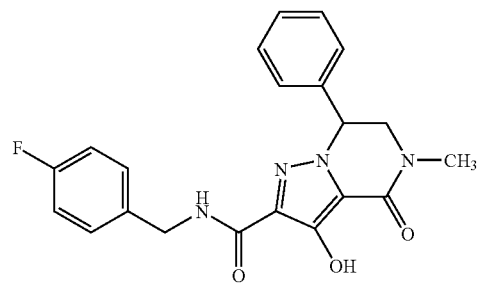

Step 1: Bromo(phenyl)acetonitrile

To a solution of benzyl cyanide (4.93 mL, 42.7 mmol) in $CCl_4$ (275 mL) were added dibenzoyl peroxide (517 mg, 2.13 mmol) and N-bromosuccinimide (9.12 g, 51.2 mmol). The reaction mixture was heated to reflux and stirred for 5 hours and concentrated in vacuo to a volume of 100 mL. The solution was partitioned between $CHCl_3$ and saturated $NaHCO_3$ solution, and the aqueous layer was extracted with several portions of $CHCl_3$. The combined organic layers were dried over $Na_2SO_4$ and concentrated in vacuo to afford a yellow oil. Purification was achieved by flash column chromatography on silica gel using a gradient elution of 0-20% EtOAc/hexanes. Collection and concentration of the appropriate fractions yielded the title compound as a pale yellow oil. $^1$H NMR (400 MHz, d$_6$-DMSO) δ 7.61-7.58 (m, 2H), 7.53-7.45 (m, 3H), 6.59 (s, 1H).

Step 2: Dimethyl 4-benzyloxy-1-[cyano(phenyl)methyl]-1H-pyrazole-3,5-dicarboxylate A solution of dimethyl 4-benzyloxy-1H-pyrazole-3,5-dicarboxylate (1.0 g, 3.45 mmol) and bromo(phenyl)acetonitrile (810 mg, 4.13 mmol) in anhydrous DMF was treated with Cs$_2$CO$_3$ (1.46 g, 4.48 mmol) and stirred at room temperature for 3 days. The solvent was removed in vacuo and the residue was partitioned between EtOAc and water. The aqueous layer was extracted with EtOAc several times, and the combined organic layers were dried over Na$_2$SO$_4$ and concentrated in vacuo. The resulting residue was purified by flash column chromatography on silica gel using a gradient elution of 0-20% EtOAc/hexanes. Collection and concentration of the appropriate fractions yielded the title product as a yellow oil. $^1$H NMR (400 MHz, d$_6$-DMSO) δ 7.70 (s, 1H), 7.50-7.45 (m, 3H), 7.43-7.29 (m, 7H), 5.08 (s, 2H), 3.86 (s, 3H), 3.81 (s, 3H); ES MS (M+1)=406.

Step 3: Methyl 3-benzyloxy-4-oxo-7-phenyl-4,5,6,7-tetrahydropyrazolo[1,5-a]pyrazine-2-carboxylate To a solution of dimethyl 4-benzyloxy-1-[cyano(phenyl) methyl]-1H-pyrazole-3,5-dicarboxylate (1.0 g, 2.47 mmol) in anhydrous MeOH (100 mL) through which nitrogen had been bubbled was added rhodium on alumina (50 mg). The mixture was then treated with ammonia gas for 5 minutes and stirred under an atmosphere of hydrogen gas overnight. The mixture was filtered through celite and the filter cake was washed with MeOH. The filtrate was concentrated and purified by reverse phase chromatography on a C-18 column using a gradient elution of 95-5% H$_2$O (0.1% TFA)/CH$_3$CN (0.1% TFA). Collection and concentration of the appropriate fractions afforded the title product as an off-white solid. $^1$H NMR (400 MHz, d$_6$-DMSO) δ 8.28 (s, 1H), 7.49-7.47 (m, 2H), 7.40-7.32 (m, 6H), 6.96-6.93 (m, 2H), 5.77 (s, 1H), 5.40-5.27 (m, 2H), 4.04-3.99 (m, 1H), 3.78 (s, 3H), 3.76-3.59 (m, 1H); ES MS (M+1)=378.

Step 4: 3-Benzyloxy-5-methyl-4-oxo-7-phenyl-4,5,6,7-tetrahydropyrazolo[1,5-a]pyrazine-2-carboxylic acid To a solution of methyl 3-benzyloxy-4-oxo-7-phenyl-4,5,6,7-tetrahydropyrazolo[1,5-a]pyrazine-2-carboxylate (28 mg, 0.074 mmol) in anhydrous DMF under inert atmosphere was added sodium hydride (3 mg, 0.111 mmol, 95% dispersion in oil). The mixture was treated with iodomethane (6 μL, 0.089 mmol) and stirred at room temperature for 1 hour. When the methylation was complete, several drops of H$_2$O were added and the mixture stirred at room temperature for 1 hour. The mixture was purified by reverse phase chromatography on a C-18 column using a gradient elution of 95-5% H$_2$O (0.1% TFA)/CH$_3$CN (0.1% TFA). Collection and concentration of the appropriate fractions yielded the title product as a white solid. $^1$H NMR (400 MHz, d$_6$-DMSO) δ 12.90 (s, 1H), 7.51-7.49 (m, 2H), 7.39-7.31 (m, 6H), 7.01-7.00 (m, 2H), 5.80 (s, 1H), 5.27 (dd, J=11.2, 25.2 Hz, 2H), 4.21 (d, J=4.8 hz, 1H), 4.18 (d, J=4.4 Hz, 1H), 2.92 (s, 3H); ES MS (M+1)=378.

Step 5: 3-Benzyloxy-N-(4-fluorobenzyl)-5-methyl-4-oxo-7-phenyl-4,5,6,7-tetrahydropyrazolo[1,5-a]pyrazine-2-carboxamide To a solution of 3-benzyloxy-5-methyl-4-oxo-7-phenyl-4,5,6,7-tetrahydropyrazolo[1,5-a]pyrazine-2-carboxylic acid (20 mg, 0.053 mmol) in anhydrous DMF were added HOBT (11 mg, 0.079 mmol), EDC (15 mg, 0.079 mmol), Et$_3$N (7 μL, 0.053 mmol), and 4-fluorobenzylamine (7 μL, 0.064 mmol). The reaction mixture was stirred at room temperature for 1 hour. Purification was achieved by reverse phase chromatography on a C-18 column using a gradient elution of 95-5% H$_2$O (0.1% TFA)/CH$_3$CN (0.1% TFA). Collection and concentration of the appropriate fractions yielded the title product as a white solid. ES MS (M+1)=485.

Step 6: N-(4-Fluorobenzyl)-3-hydroxy-5-methyl-4-oxo-7-phenyl-4,5,6,7-tetrahydropyrazolo[1,5-a]pyrazine-2-carboxamide The title compound was hydrogenated using a procedure similar to that described in Example 1, Step 5, except that the reaction time totaled 1 hour. $^1$H NMR (400 MHz, d$_6$-DMSO) δ 9.55 (br s, 1H), 8.79 (t, J=6.0 Hz, 1H), 7.39-7.31 (m, 5H), 7.15-7.10 (m, 2H), 7.05-7.03 (m, 2H), 5.74 (t, J=4.0 Hz, 1H), 4.44-4.32 (m, 2H), 4.21-4.13 (m, 1H), 3.82-3.77 (m, 1H), 2.87 (s, 3H); ES MS (M+1)=395.

Step 7: Enantiomers of N-(4-Fluorobenzyl)-3-hydroxy-5-methyl-4-oxo-7-phenyl-4,5,6,7-tetrahydropyrazolo[1,5-a]pyrazine-2-carboxamide The enantiomers of 3-benzyloxy-N-(4-fluorobenzyl)-5-methyl-4-oxo-7-phenyl-4,5,6,7-tetrahydropyrazolo[1,5-a] pyrazine-2-carboxamide were separated by chiral chromatography on a ChiralPak AD column using an isocratic elution of 1:1 MeOH/EtOH. The earlier eluting enantiomer had a positive sign of rotation while the later eluting enantiomer showed a negative sign of rotation. Each enantiomer of 3-benzyloxy-N-(4-fluorobenzyl)-5-methyl-4-oxo-7-phenyl-4,5,6, 7-tetrahydropyrazolo[1,5-a]pyrazine-2-carboxamide was hydrogenated using a procedure similar to that described in Example 1, Step 5, followed by purification using reverse phase chromatography on a C-18 column using a gradient elution of 95-5% H$_2$O (0.1% TFA)/CH$_3$CN (0.1% TFA). (+) Enantiomer: $^1$H NMR (400 MHz, d$_6$-DMSO) δ 9.51 (s, 1H), 8.80 (t, J=6.4 Hz, 1H), 7.39-7.31 (m, 5H), 7.16-7.12 (m, 2H), 7.11-7.03 (m, 2H), 5.74 (t, J=4.0 Hz, 1H), 4.45-4.32 (m, 2H), 4.18 (dd, J=4.8, 13.6 Hz, 1H), 3.80 (dd, J=4.0, 13.6 Hz, 1H), 2.87 (s, 3H); HRMS (FT-ICR) C$_{21}$H$_{19}$FN$_4$O$_3$+H=395.1521; calculated 395.1514. (−) Enantiomer: $^1$H NMR (400 MHz, d$_6$-DMSO) δ 9.53 (s, 1H), 8.81 (t, J=6.0 Hz, 1H), 7.39-7.31 (m, 5H), 7.15-7.10 (m, 2H), 7.05-7.03 (m, 2H), 5.74 (t, J=4.0 Hz, 1H), 4.44-4.32 (m, 2H), 4.18 (dd, J=4.4, 13.6 Hz, 1H), 3.79 (dd, J=4.0, 13.6 Hz, 1H), 2.87 (s, 3H); HRMS (FT-ICR) C$_{21}$H$_{19}$FN$_4$O$_3$+H=395.1552; calculated 395.1514.

EXAMPLE 3

N-(4-Fluoro-2-[(methylamino)carbonyl]benzyl)-3-hydroxy-5-methyl-4-oxo-7-phenyl-4,5,6,7-tetrahydropyrazolo[1,5-a]pyrazine-2-carboxamide

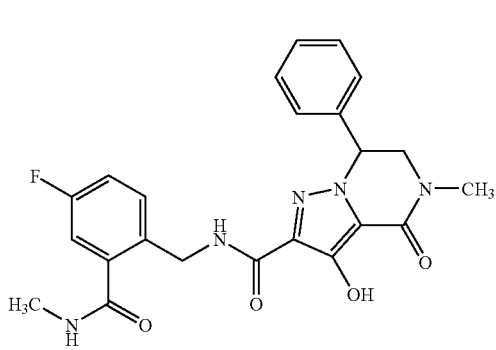

Step 1: 3-Benzyloxy-N-(4-fluoro-2-[(methylamino)carbonyl]benzyl)-5-methyl-4-oxo-7-phenyl-4,5,6,7-tetrahydropyrazolo[1,5-a]pyrazine-2-carboxamide The title compound was prepared from 3-benzyloxy-5-methyl-4-oxo-7-phenyl-4,5,6,7-tetrahydropyrazolo[1,5-a]pyrazine-2-carboxylic acid using a procedure similar to that described in Example 2, Step 5, except that 4-fluoro-2-[(methylamino)carbonyl]benzylamine hydrochloride was used in place of 4-fluorobenzylamine. $^1$H NMR (400 MHz, $d_6$-DMSO) δ 8.51 (d, J=4.8 Hz, 1H), 8.38 (t, J=4.0 Hz, 1H), 7.43-7.24 (m, 11H), 6.92-6.91 (m, 2H), 5.78-5.77 (m, 1H), 5.36 (dd, J=10.8, 38.4 Hz, 2H), 4.46 (dd, J=6.0, 18.4 Hz, 2H), 4.23 (dd, J=4.4, 13.6 Hz, 1H), 3.81 (dd, J=3.2, 13.6 Hz, 1H), 2.89 (s, 3H), 2.73 (s, 3H); ES MS (M+1)=542.

Step 2: N-(4-Fluoro-2-[(methylamino)carbonyl]benzyl)-3-hydroxy-5-methyl-4-oxo-7-phenyl-4,5,6,7-tetrahydropyrazolo[1,5-a]pyrazine-2-carboxamide The title compound was prepared from 3-benzyloxy-N-(4-fluoro-2-[(methylamino)carbonyl]benzyl)-5-methyl-4-oxo-7-phenyl-4,5,6,7-tetrahydropyrazolo[1,5-a]pyrazine-2-carboxamide using a hydrogenation procedure similar to that described in Example 1, Step 5, except that the reaction time totaled 2 hours. $^1$H NMR (400 MHz, $d_6$-DMSO) δ 9.51 (s, 1H), 8.55 (t, J=6.4 Hz, 1H), 7.40-7.31 (m, 4H), 7.28-7.23 (m, 2H), 7.03-7.02 (m, 2H), 5.75 (t, J=4.4 Hz, 1H), 4.56-4.42 (m, 2H), 4.18 (dd, J=4.4, 13.4 Hz, 1H), 3.80 (dd, J=4.0, 13.4 Hz, 1H), 2.87 (s, 3H), 2.75 (d, J=4.6 Hz, 3H); HRMS (FT-ICR) $C_{23}H_{22}FN_5O_4$+H=452.1731; calculated 452.1729.

EXAMPLE 4

5-(4-Fluorobenzyl)-3-hydroxy-N-methyl-4-oxo-7-phenyl-4,5,6,7-tetrahydropyrazolo[1,5-a]pyrazine-2-carboxamide

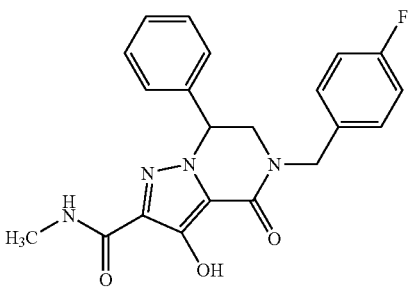

Step 1: 3-Benzyloxy-5-(4-fluorobenzyl)-4-oxo-7-phenyl-4,5,6,7-tetrahydropyrazolo[1,5-a]pyrazine-2-carboxylic acid The title compound was prepared from methyl 3-benzyloxy-4-oxo-7-phenyl-4,5,6,7-tetrahydropyrazolo[1,5-a]pyrazine-2-carboxylate using a procedure similar to that described in Example 2, Step 4, except that 4-fluorobenzyl bromide was used in place of iodomethane, and 1N aqueous NaOH was used to quench the reaction and saponify the ester. ES MS (M+1)=472.

Step 2: 3-Benzyloxy-5-(4-fluorobenzyl)-N-methyl-4-oxo-7-phenyl-4,5,6,7-tetrahydropyrazole[1,5-a]pyrazine-2-carboxamide The title compound was prepared from 3-benzyloxy-5-(4-fluorobenzyl)-4-oxo-7-phenyl-4,5,6,7-tetrahydropyrazolo[1,5-a]pyrazine-2-carboxylic acid using a procedure similar to that described in Example 2, Step 5, except that methylamine was used in place of 4-fluorobenzylamine. ES MS (M+1)=485.

Step 3: 5-(4-Fluorobenzyl)-3-hydroxy-N-methyl-4-oxo-7-phenyl-4,5,6,7-tetrahydropyrazolo[1,5-a]pyrazine-2-carboxamide The title compound was prepared from 3-benzyloxy-5-(4-fluorobenzyl)-N-methyl-4-oxo-7-phenyl-4,5,6,7-tetrahydropyrazole[1,5-a]pyrazine-2-carboxamide using a hydrogenation procedure similar to that described in Example 1, Step 5, except that the reaction time totaled 1 hour and the material was triturated with MeOH for further purification. $^1$H NMR (400 MHz, $d_6$-DMSO) δ 8.25-8.24 (m, 1H), 7.29-7.28 (m, 3H), 7.06-7.03 (m, 2H), 6.98-6.93 (m, 2H), 6.87-6.83 (m, 2H), 5.74 (t, J=3.6 Hz, 1H), 4.68 (d, J=14.8 Hz, 1H), 4.34 (d, J=15.2 Hz, 1H), 4.16 (dd, J=4.4, 13.2 Hz, 1H), 3.71 (d, J=3.2 Hz, 1H), 3.17 (s, 3H); ES MS (M+1)=395.

EXAMPLE 5

5,6-Dimethyl-N-(4-fluorobenzyl)-3-hydroxy-4-oxo-4,5,6,7-tetrahydropyrazolo[1,5-a]pyrazine-2-carboxamide

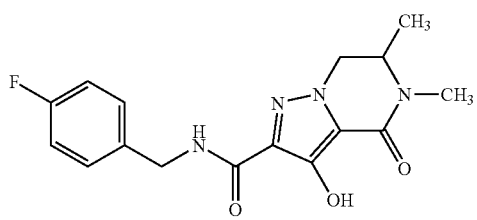

Step 1: Dimethyl 4-benzyloxy-1-(2-oxopropyl)-1H-pyrazole-3,5-dicarboxylate

The title compound was prepared from dimethyl 4-benzyloxy-1H-pyrazole-3,5-dicarboxylate using a procedure similar to that described in Example 2, Step 2, except that chloroacetone was used in place of bromo(phenyl)acetonitrile, and the silica gel chromatography gradient elution was 0-60% EtOAc/hexanes. $^1$H NMR (400 MHz, d$_6$-DMSO) δ 7.46-7.34 (m, 5h), 5.44 (s, 2H), 5.06 (s, 2H), 3.83 (s, 3H), 3.78 (s, 3H), 2.20 (s, 3H); ES MS (M+1)=347.

Step 2: Methyl 3-benzyloxy-5,6-dimethyl-4-oxo-4,5,6,7-tetrahydropyrazolo[1,5-a]pyrazine-2-carboxylate To a solution of dimethyl 4-benzyloxy-1-(2-oxopropyl)-1H-pyrazole-3,5-dicarboxylate (80 mg, 0.231 mmol) in anhydrous CH$_2$Cl$_2$ were added methylamine (173 µL, 2.0M in THF), sodium triacetoxyborohydride (98 mg, 0.462 mmol), and AcOH (20 µL, 0.346 mmol). The reaction was stirred at room temperature overnight. Toluene was added to replace the evaporated solvent, and the mixture was heated to 110° C. for 3 h. The solvent was removed in vacuo, and purification was achieved by reverse phase chromatography on a C-18 column using a gradient elution of 95-5% H$_2$O (0.1% TFA)/CH$_3$CN (0.1% TFA). Collection and concentration of the appropriate fractions afforded the title product as a yellow oil. ES MS (M+1)=330.

Step 3: 3(Benzyloxy-N-(4-fluorobenzyl)-5,6-dimethyl-4-oxo-4,5,6,7-tetrahydropyrazolo[1,5-a]pyrazine-2-carboxamide To a solution of methyl 3-benzyloxy-5,6-dimethyl-4-oxo-4,5,6,7-tetrahydropyrazolo[1,5-a]pyrazine-2-carboxylate (72 mg, 0.219 mmol) in MeOH was added 4-fluorobenzylamine (376 µL, 3.28 mmol). The mixture was heated to reflux overnight and then at 110° C. for 4 hours. The mixture was purified by reverse phase chromatography on a C-18 column using a gradient elution of 95-5% H$_2$O (0.1% TFA)/CH$_3$CN (0.1% TFA), and collection and concentration of the appropriate fractions afforded the amide as a yellow oil. ES MS (M+1)=423.

Step 4: 5,6-Dimethyl-N-(4-fluorobenzyl)-3-hydroxy-4-oxo-4,5,6,7-tetrahydropyrazolo[1,5-a]pyrazine-2-carboxamide The title compound was prepared from 3-benzyloxy-N-(4-fluorobenzyl)-5,6-dimethyl-4-oxo-4,5,6,7-tetrahydropyrazolo[1,5-a]pyrazine-2-carboxamide using a hydrogenation procedure similar to that described in Example 1, Step 5, except that the reaction time totaled 2 hours. $^1$H NMR (400 MHz, d$_6$-DMSO) δ 9.37 (s, 1H), 8.84 (t, J=6.0 Hz, 1H), 7.38-7.31 (m, 2H), 7.17-7.12 (m, 2H), 4.47-4.41 (m, 3H), 4.15 (dd, J=2.4, 13.6 Hz, 1H), 3.97-3.94 (m, 1H), 2.97 (s, 3H), 1.17 (d, J=6.8 Hz, 3H); HRMS (FT-ICR) C$_{16}$H$_{17}$FN$_4$O$_3$+ H=333.1366; calculated 333.1358.

EXAMPLE 6

5-(4-Fluorobenzyl)-3-hydroxy-N-methyl-6-methyl-4-oxo-4,5,6,7-tetrahydropyrazolo[1,5-a]pyrazine-2-carboxamide

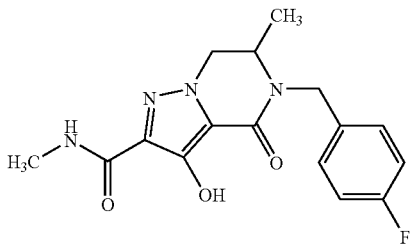

Step 1: Methyl 3-benzyloxy-5-(4-fluorobenzyl)-6-methyl-4-oxo-4,5,6,7-tetrahydropyrazolo[1,5-a]pyrazine-2-carboxylate The title compound was prepared from dimethyl 4-benzyloxy-1-(2-oxopropyl)-1H-pyrazole-3,5-dicarboxylate using a procedure similar to that described in Example 5, Step 2, except that the reaction mixture was heated to 110° C. overnight. $^1$H NMR (400 MHz, d$_6$-DMSO) δ 7.45-7.42 (m, 4H), 7.36-7.28 (m, 3H), 7.21-7.17 (m, 2H), 5.27 (dd, J=11.2, 18.4 Hz, 2H), 5.00 (d, J=15.2 Hz, 1H), 4.45-4.36 (m, 2H), 4.20 (d, J=13.6 Hz, 1H), 2.94 (t, J=4.8 Hz, 1H), 3.80 (s, 3H), 0.99 (d, J=6.8 Hz, 3H); ES MS (M+1)=424.

Step 2: 3-Benzyloxy-5-(4-fluorobenzyl)-N-methyl-6-methyl-4-oxo-4,5,6,7-tetrahydropyrazolo[1,5-a]pyrazine-2-carboxamide The title compound was prepared from methyl 3-benzyloxy-5-(4-fluorobenzyl)-6-methyl-4-oxo-4,5,6,7-tetrahydropyrazolo[1,5-a]pyrazine-2-carboxylate using a procedure similar to that described in Example 5, Step 3, except that methylamine (2M in MeOH) was used in place of 4-fluorobenzylamine, and the reaction was heated to reflux overnight. The solvent was removed in vacuo, and the material was used without purification. ES MS (M+1)=423.

Step 3: 5-(4-Fluorobenzyl)-3-hydroxy-N-methyl-6-methyl-4-oxo-4,5,6,7-tetrahydropyrazolo[1,5-a]pyrazine-2-carboxamide The title compound was prepared from 3-benzyloxy-5-(4-fluorobenzyl)-N-methyl-6-methyl-4-oxo-4,5,6,7-tetrahydropyrazolo[1,5-a]pyrazine-2-carboxamide using a procedure similar to that described in Example 1, Step 5, except that the reaction time totaled 1 hour. Purification was achieved by reverse phase chromatography on a C-18 column using a gradient elution of 95-5% H$_2$O (0.1% TFA)/CH$_3$CN (0.1% TFA). $^1$H NMR (400 MHz, $d_6$-DMSO) δ 9.57 (br s, 1H), 8.28-8.27 (m, 1H), 7.43-7.40 (m, 2H), 7.20-7.16 (m, 2H), 5.01 (d, J=15.2 Hz, 1H), 4.41-4.28 (m, 2H), 4.13 (dd, J=2.0, 13.2 Hz, 1H), 3.92-3.89 (m, 1H), 2.78 (s, 3H), 1.11 (d, J=6.4 Hz, 3H); ES MS (M+1)=333.

EXAMPLE 7

N-(4-Fluorobenzyl)-3-hydroxy-5-methyl-4-oxo-7-(piperidin-1-ylcarbonyl)-4,5,6,7-tetrahydropyrazolo[1,5-a]pyrazine-2-carboxamide

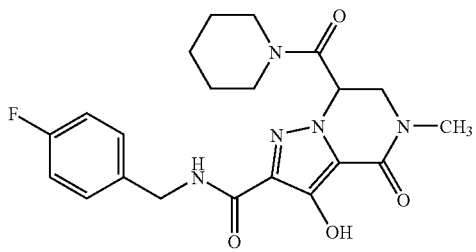

Step 1: Ethyl 3-bromo-2-hydroxypropanoate

To a solution of sodium cyanoborohydride (17.72 g, 282.0 mmol) in anhydrous MeOH (160 mL) under an atmosphere of nitrogen was added ethyl bromopyruvate (32.25 mL, 256.4 mmol, 80-85%) in anhydrous MeOH (160 mL). The mixture was treated with 1N HCl in diethyl ether to pH 4 and stirred for 1 h at 0° C. The solvent was removed in vacuo, and the resulting slurry was partitioned between diethyl ether and saturated aqueous NH$_4$Cl solution. The aqueous layer was extracted several times into diethyl ether, and the organic extracts were combined, dried over Na$_2$SO$_4$ and concentrated to a pale yellow oil. The oil was diluted with diethyl ether (300 mL) and chilled to −78° C. for 1 hour. The resulting precipitate was collected by filtration to afford the alcohol as a white solid. $^1$H NMR (400 MHz, $d_6$-DMSO) δ 5.99 (dd, J=1.2, 6.0 Hz, 1H), 4.43-4.39 (m, 1H), 4.21-4.08 (m, 2H), 3.69 (d, J=0.8 Hz, 2H), 1.23-1.18 (m, 3H).

Step 2: Ethyl 3-azido-2-hydroxypropanoate

To a solution of ethyl 3-bromo-2-hydroxypropanoate (22.1 g, 112.0 mmol) in EtOH/H$_2$O (1:1) was added sodium azide (10.9 g, 168.0 mmol). The reaction was stirred and heated to 90° C. for 3 days. The EtOH was removed in vacuo and the remaining aqueous solution was extracted with CHCl$_3$ several times. The combined organic extracts were dried over Na$_2$SO$_4$ and concentrated in vacuo to afford the azide as an orange oil. $^1$H NMR (400 MHz, $d_6$-DMSO) δ 5.96 (d, J=5.6 Hz, 1H), 4.31-4.28 (m, 1H), 4.19-4.08 (m, 2H), 3.51-3.40 (m, 2H), 1.28-1.17 (m, 3H).

Step 3: Ethyl 3-[(tert-butoxycarbonyl)amino]-2-hydroxypropanoate

To a solution of ethyl 3-azido-2-hydroxypropanoate (15.8 g, 99.47 mmol) in EtOAc purged with nitrogen were added di-tert-butyl dicarbonate (23.9 g, 109.4 mmol) and 10% palladium on carbon. The mixture was placed under an atmosphere of hydrogen at 35 psi and shaken for 4 days. The mixture was filtered through celite and the filter cake was washed with EtOAc. The filtrate was concentrated in vacuo and purified by flash column chromatography on silica gel using a gradient elution of 10-55% EtOAc/hexanes. Collection and concentration of the appropriate fractions afforded the amine as a yellow oil. $^1$H NMR (400 MHz, $d_6$-DMSO) δ 6.77 (t, J=5.6 Hz, 1H), 5.49 (br s, 1H), 4.09-4.03 (m, 2H), 3.23-3.08 (m, 2H), 1.36 (s, 9H), 1.19 (t, J=7.2 Hz, 3H); ES MS (M+Na)=256.

Step 4: Ethyl 3-[(tert-butoxycarbonyl)amino]-2-(methylsulfonyloxy)propanoate To a solution of ethyl 3-[(tert-butoxycarbonyl)amino]-2-hydroxypropanoate (18.6 g, 79.72 mmol) and diisopropylethylamine (34.7 mL, 199.3 mmol) in anhydrous CH$_2$Cl$_2$ at −30° C. was added methane sulfonic anhydride (16.7 g, 95.7 mmol). The reaction was stirred for 1 hour, and the solvent removed in vacuo. The residue was purified by flash column chromatography on silica gel using a gradient elution of 15-50% EtOAc/hexanes. Collection and concentration of appropriate fractions afforded the title product as a yellow oil. $^1$H NMR (400 MHz, $d_6$-DMSO) δ 7.18 (t, J=5.6 Hz, 1H), 5.03 (dd, J=4.4, 6.4 Hz, 1H), 4.16 (d, J=7.2, 14.0 Hz, 2H), 3.43-3.33 (m, 2H), 3.21 (s, 3H), 1.37 (s, 9H), 1.77 (t, J=7.2 Hz, 3H).

Step 5: Dimethyl 4-benzyloxy-1-{2-[(tert-butoxycarbonyl)amino]-1-(ethoxycarbonyl)ethyl}-1H-pyrazole-3,5-dicarboxylate To a solution of dimethyl 4-benzyloxy-1H-pyrazole-3,5-dicarboxylate (4.0 g, 13.8 mmol) and ethyl 3-[(tert-butoxycarbonyl)amino]-2-(methylsulfonyloxy)propanoate (4.29 g, 13.8 mmol) in anhydrous CH$_3$CN (200 mL) was added Cs$_2$CO$_3$ (4.49 g, 13.8 mmol). The mixture was heated to 50° C. overnight, cooled to room temperature, and filtered. The filtrate was concentrated in vacuo to afford the title product as a pale yellow oil. ES MS (M+H)=506.

Step 6: Methyl 3-benzyloxy-7-ethoxycarbonyl-4-oxo-4,5,6,7-tetrahydropyrazolo[1,5-a]pyrazine-2-carboxylate To a solution of dimethyl 4-(benzyloxy)-1-{2-[(tert-butoxycarbonyl)amino]-1-(ethoxycarbonyl)ethyl}-1H-pyrazole-3,5-dicarboxylate (6.97 g, 13.78 mmol) in CHCl$_3$ (150 mL) was added TFA (30 mL). The reaction was allowed to stir at room temperature overnight. The solvent was removed in vacuo, and the residue was partitioned between saturated aqueous NaHCO$_3$ solution and CHCl$_3$. The aqueous layer was extracted three times with CHCl$_3$, and the combined organic extracts were dried over Na$_2$SO$_4$. Concentration in vacuo afforded a yellow oil which was dissolved in EtOAc (30 mL) and sonicated. The resulting precipitate was collected by filtration to afford the title product as a white solid. The filtrate was further purified by reverse phase chromatography on a C-18 column using a gradient elution of 95-5% H$_2$O (0.1% TFA)/CH$_3$CN (0.1% TFA), and collection and concentration of the appropriate fractions afforded additional title product as a white solid. $^1$H NMR (400 MHz, $d_6$-DMSO) δ 8.38 (d, J=5.2 Hz, 1H), 6.45-7.43 (m, 2H), 7.38-7.30 (m, 3H), 5.55 (d, J=4.0 Hz, 1H), 5.26 (dd, J=11.2, 40.0 Hz, 2H), 4.23-4.14 (m, 2H), 3.97 (dd, J=5.0, 13.8 Hz, 1H), 3.79 (s, 3H), 3.71 (dd, J=5.4, 13.8 Hz, 1H), 1.18 (t, J=7.0 Hz, 3H); ES MS (M+H)=374.

Step 7: Methyl 3-benzyloxy-7-ethoxycarbonyl-5-methyl-4-oxo-4,5,6,7-tetrahydropyrazolo[1,5-a]pyrazine-2-carboxylate Methyl 3-benzyloxy-7-ethoxycarbonyl-4-oxo-4,5,6,7-tetrahydropyrazolo[1,5-a]pyrazine-2-carboxylate (4.0 g, 10.71 mmol) was azeotroped from toluene and dissolved in anhydrous DMF (20 mL), and iodomethane (700 µL, 11.25 mmol) was passed through a plug of activated basic alumina and added to the solution. After being cooled to 0° C., the solution was treated with sodium hydride (270 mg, 11.25 mmol, 95% dispersion in oil) and stirred for 1 hour. The reaction was quenched with acetic acid, and the solvent removed in vacuo. The resulting residue was triturated with diethyl ether to afford a solid which was partitioned between saturated aqueous $NaHCO_3$ and EtOAc. The aqueous layer was extracted into EtOAc three times more, and the combined organic extracts were dried over $Na_2SO_4$ and concentrated to afford the title product as a yellow oil. $^1$H NMR (400 MHz, $d_6$-DMSO) δ 7.49-7.44 (m, 2H), 7.39-7.32 (m, 3H), 5.29-5.15 (m, 2H), 4.23-4.13 (m, 3H), 4.00-3.80 (m, 1H), 3.79 (s, 3H), 3.41-3.36 (m, 1H), 3.00 (s, 3H), 1.20-1.11 (m, 3H); ES MS (M+H)=388.

Step 8: 3-Benzyloxy-2-methoxycarbonyl-5-methyl-4-oxo-4,5,6,7-tetrahydropyrazolo[1,5-a]pyrazine-7-carboxylic acid To a solution of methyl 3-benzyloxy-7-ethoxycarbonyl-5-methyl-4-oxo-4,5,6,7-tetrahydropyrazolo[1,5-a]pyrazine-2-carboxylate (195 mg, 0.503 mmol) in MeOH/THF (0.5 mL) was added aqueous 1N NaOH (554 µL, 0.554 mmol). The mixture was stirred for 1 hour and quenched by the addition aqueous 3N HCl (170 µL). Purification by reverse phase chromatography on a C-18 column using a gradient elution of 95-5% $H_2O$ (0.1% TFA)/$CH_3CN$ (0.1% TFA) and collection and concentration of the appropriate fractions afforded the title product as a white solid. $^1$H NMR (400 MHz, $d_6$-DMSO) δ 7.49-7.47 (m, 2H), 7.40-7.33 (m, 3H), 5.44 (br s, 1H), 5.21 (dd, J=11.2, 30.4 Hz, 2H), 4.18 (dd, J=4.8, 13.6 Hz, 1H), 3.91 (d, J=13.6 Hz, 1H), 3.80 (s, 3H), 3.01 (s, 3H); ES MS (M+H)=360.

Step 9: Methyl 3-benzyloxy-5-methyl-4-oxo-7-(piperidin-1-ylcarbonyl)-4,5,6,7-tetrahydropyrazolo[1,5-a]pyrazine-2-carboxylate The title compound was prepared from 3-benzyloxy-2-methoxycarbonyl-5-methyl-4-oxo-4,5,6,7-tetrahydropyrazolo[1,5-a]pyrazine-7-carboxylic acid using a procedure similar to that described in Example 2, Step 5 except that piperidine was used in place of 4-fluorobenzylamine, and the reaction time totaled 18 hours. $^1$H NMR (400 MHz, $d_6$-DMSO) δ 7.50-7.48 (m, 2H), 7.40-7.31 (m, 3H), 5.88 (d, J=2.4 Hz, 1H), 5.19 (dd, J=11.2, 25.6 Hz, 2H), 4.14 (dd, J=5.2, 13.6 Hz, 1H), 3.78 (s, 3H), 3.68-3.52 (m, 4H), 3.34-3.33 (m, 1H), 2.98 (s, 3H), 1.62 (br s, 4H), 1.47 (br s, 2H); ES MS (M+H)=427.

Step 10: Methyl 3-hydroxy-5-methyl-4-oxo-7-(piperidin-1-ylcarbonyl)-4,5,6,7-tetrahydropyrazolo[1,5-a]pyrazine-2-carboxylate The title compound was prepared from methyl 3-benzyloxy-5-methyl-4-oxo-7-(piperidin-1-ylcarbonyl)-4,5,6,7-tetrahydropyrazolo[1,5-a]pyrazine-2-carboxylate using a hydrogenation procedure similar to that described in Example 1, Step 5 except that the reaction time totaled 1 hour. $^1$H NMR (400 MHz, $d_6$-DMSO) δ 9.12 (br s, 1H), 5.80-5.79 (m, 1H), 4.09 (dd, J=5.2, 13.6 Hz, 1H), 3.78 (s, 3H), 3.63-3.51 (m, 4H), 3.34-3.31 (m, 1H), 2.93 (s, 3H), 1.60 (br s, 4H), 1.46 (br s, 2H); ES MS (M+H)=427.

Step 11: N-(4-Fluorobenzyl)-3-hydroxy-5-methyl-4-oxo-7-(piperidin-1-ylcarbonyl)-4,5,6,7-tetrahydropyrazolo[1,5-a]pyrazine-2-carboxamide The title compound was prepared from methyl 3-hydroxy-5-methyl-4-oxo-7-(piperidin-1-ylcarbonyl)-4,5,6,7-tetrahydropyrazolo[1,5-a]pyrazine-2-carboxylate using a procedure similar to that described in Example 5, Step 3 except that toluene was used in place of MeOH, and the reaction was heated to 90° C. overnight. $^1$H NMR (400 MHz, $d_6$-DMSO) δ 9.36 (br s, 1H), 8.79 (t, J=5.6 Hz, 1H), 7.36-7.33 (m, 2H), 7.16-7.12 (m, 2H), 5.78-5.76 (m, 1H), 4.41 (d, J=6.4 Hz, 2H), 4.11 (dd, J=4.8, 14.0 Hz, 1H), 3.61-3.46 (m, 4H), 3.37-3.33 (m, 1H), 2.93 (s, 3H), 1.61 (br s, 4H), 1.46 (br s, 2H); HRMS (FT-ICR) $C_{21}H_{24}FN_5O_4$+H=430.1868; calculated 430.1885.

EXAMPLE 8

5,7-Dimethyl-N-(4-fluorobenzyl)-3-hydroxy-7-(dimethylaminocarbonyl)-4-oxo-4,5,6,7-tetrahydropyrazolo[1,5-a]pyrazine-2-carboxamide

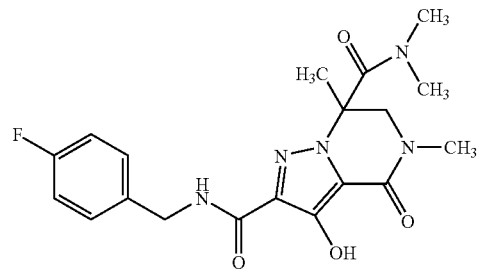

Step 1: Methyl 3-benzyloxy-5,7-dimethyl-7-ethoxycarbonyl-4-oxo-4,5,6,7-tetrahydropyrazolo[1,5-a]pyrazine-2-carboxylate To a solution of methyl 3-benzyloxy-7-ethoxycarbonyl-4-oxo-4,5,6,7-tetrahydropyrazolo[1,5-a]pyrazine-2-carboxylate (500 mg, 1.34 mmol) in anhydrous DMF at 0° C. were added sodium hydride (35 mg, 1.47 mmol, 95% dispersion in oil) and iodomethane (100 µL, 1.61 mmol). The reaction was stirred for 1 hour and allowed to warm to room temperature. The mixture was quenched with aqueous 3N HCl (447 µL, 1.34 mmol) and partitioned between EtOAc and $H_2O$. The aqueous layer was extracted several times with EtOAc, and the combined organic extracts were dried over $Na_2SO_4$ and concentrated to a yellow residue. Purification by reverse phase chromatography on a C-18 column using a gradient elution of 95-5% $H_2O$ (0.1% TFA)/$CH_3CN$ (0.1% TFA) and collection and concentration of the appropriate fractions afforded the title product as a clear oil. $^1$H NMR (400 MHz, $d_6$-DMSO) δ 7.49-7.47 (m, 2H), 7.43-7.31 (m, 3H), 5.20 (dd, J=11.2, 39.6 Hz, 2H), 4.19-4.11 (m, 2H), 3.98 (q, J=13.6 Hz, 2H), 3.80 (s, 3H), 2.99 (s, 3H), 1.81 (s, 3H), 1.13 (t, J=7.2 Hz, 3H); ES MS (M+H)=402.

Step 2: 3-Benzyloxy-2-methoxycarbonyl-5,7-dimethyl-4-oxo-4,5,6,7-tetrahydropyrazolo[1,5-a]pyrazine-7-carboxylic acid The title compound was prepared from methyl 3-benzyloxy-5,7-dimethyl-7-ethoxycarbonyl-4-oxo-4,5,6,7-tetrahydropyrazolo[1,5-a]pyrazine-2-carboxylate using a procedure similar to that described in Example 7, Step 8, except that the reaction time totaled 2 hours. $^1$H NMR (400 MHz, d$_6$-DMSO) δ 7.50-7.48 (m, 2H), 7.40-7.31 (m, 3H), 5.18 (dd, J=10.8, 38.4 Hz, 2H), 3.95 (s, 3H), 3.80 (s, 3H), 3.00 (s, 3H), 1.79 (s, 3H); ES MS (M+H)=374.

Step 3: Methyl 3-benzyloxy-5,7-dimethyl-7-dimethylaminocarbonyl-4-oxo-4,5,6,7-tetrahydropyrazolo[1,5-a]pyrazine-2-carboxylate The title compound was prepared from 3-benzyloxy-5,7-dimethyl-2-methoxycarbonyl-4-oxo-4,5,6,7-tetrahydropyrazolo[1,5-a]pyrazine-7-carboxylic acid using a procedure similar to that described in Example 2, Step 5 except that 2N dimethylamine in THF was used in place of 4-fluorobenzylamine, and the reaction time totaled 4 days. $^1$H NMR (400 MHz, d$_6$-DMSO) δ 7.47-7.45 (m, 2H), 7.38-7.32 (m, 3H), 5.23 (dd, J=10.8, 16.0 Hz, 2H), 4.16 (d, J=13.6 Hz, 1H), 3.81-3.76 (m, 4H), 3.00 (s, 3H), 2.72 (br s, 6H), 1.78 (s, 3H); ES MS (M+H)=401.

Step 4: Methyl 5,7-dimethyl-7-dimethylaminocarbonyl-3-hydroxy-4-oxo-4,5,6,7-tetrahydropyrazolo[1,5-a]pyrazine-2-carboxylate The title compound was prepared from methyl 3-benzyloxy-5,7-dimethyl-7-dimethylaminocarbony-4-oxo-4,5,6,7-tetrahydropyrazolo[1,5-a]pyrazine-2-carboxylate using a hydrogenation procedure similar to that described in Example 1, Step 5 except that the reaction time totaled 1 hour. ES MS (M+H)=311.

Step 5: 5,7-Dimethyl-7-dimethylaminocarbonyl-N-(4-fluorobenzyl)-3-hydroxy-4-oxo-4,5,6,7-tetrahydropyrazolo[1,5-a]pyrazine-2-carboxamide The title compound was prepared from methyl 5,7-dimethyl-7-dimethylaminocarbonyl-3-hydroxy-4-oxo-4,5,6,7-tetrahydropyrazolo[1,5-a]pyrazine-2-carboxylate using a procedure similar to that described in Example 5, Step 3 except that toluene was used in place of MeOH, and the reaction time totaled 2 hours. $^1$H NMR (400 MHz, d$_6$-DMSO) δ 9.45 (br s, 1H), 8.79 (t, J=6.0 Hz, 1H), 7.38-7.34 (m, 2H), 7.18-7.13 (m, 2H), 4.49-4.37 (m, 2H), 4.13 (d, J=13.6 Hz, 1H), 3.70 (d, J=13.2 Hz, 1H), 2.95 (s, 3H), 2.77 (s, 6H), 1.77 (s, 3H); HRMS (FT-ICR) C$_{19}$H$_{22}$FN$_5$O$_4$+H=404.1716; calculated 404.1729.

EXAMPLE 9

N-(4-fluorobenzyl)-3-hydroxy-5-methyl-4-oxo-7-(piperidin-1-ylmethyl)-4,5,6,7-tetrahydropyrazolo[1,5-a]pyrazine-2-carboxamide

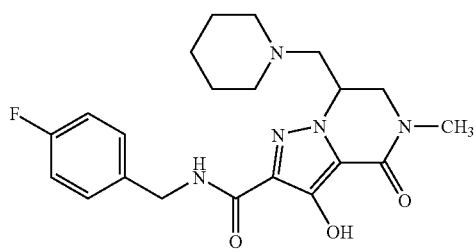

Step 1: Methyl 3-benzyloxy-7-hydroxymethyl-5-methyl-4-oxo-4,5,6,7-tetrahydropyrazolo[1,5-a]pyrazine-2-carboxylate To a solution of 3-benzyloxy-2-methoxycarbonyl-5-methyl-4-oxo-4,5,6,7-tetrahydropyrazolo[1,5-a]pyrazine-7-carboxylic acid (183 mg, 0.509 mmol) in anhydrous THF under an atmosphere of nitrogen was added 1M borane-THF complex (6.11 mL, 6.11 mmol). The reaction was stirred at room temperature for 1 hour and quenched with aqueous 6N HCl. The solvent was removed in vacuo, and the resulting residue was purified by reverse phase chromatography on a C-18 column using a gradient elution of 95-5% H$_2$O (0.1% TFA)/CH$_3$CN (0.1% TFA). Collection and concentration of the appropriate fractions afforded the alcohol as a sticky, clear oil. $^1$H NMR (400 MHz, d$_6$-DMSO) δ 7.49-7.47 (m, 2H), 7.39-7.30 (m, 3H), 5.18 (s, 2H), 4.50-4.47 (m, 1H), 4.27 (br s, 1H), 4.07 (dd, J=5.2, 13.6 Hz, 1H), 3.91 (dd, J=5.2, 13.2 Hz, 1H), 3.79 (s, 3H), 3.78-3.71 (m, 2H), 3.03 (s, 3H); ES MS (M+H)=346.

Step 2: Methyl 3-benzyloxy-5-methyl-7-methylsulfonyloxymethyl-4-oxo-4,5,6,7-tetrahydropyrazolo[1,5-a]pyrazine-2-carboxylate The title compound was prepared from methyl 3-benzyloxy-7-hydroxymethyl-5-methyl-4-oxo-4,5,6,7-tetrahydropyrazolo[1,5-a]pyrazine-2-carboxylate using a procedure similar to that described in Example 7, Step 4, except that the reaction was initially cooled to 0° C. for the addition of all reagents and then allowed to warm to room temperature while stirring overnight. $^1$H NMR (400 MHz, d$_6$-DMSO) δ 7.49-7.47 (m, 2H), 7.39-7.31 (m, 3H), 5.19 (s, 2H), 4.95 (t, J=4.8 Hz, 1H), 4.67 (dd, J=5.2, 10.8 Hz, 1H), 4.58 (dd, J=4.8, 11.2 Hz, 1H), 4.01 (dd, J=5.2, 13.6 Hz, 1H), 3.83-3.74 (m, 4H), 3.20 (s, 3H), 3.03 (s, 3H); ES MS (M+H)=424.

Step 3: Methyl 3-benzyloxy-5-methyl-4-oxo-7-(piperidin-1-ylmethyl)-4,5,6,7-tetrahydropyrazolo[1,5-a]pyrazine-2-carboxylate To a solution of methyl 3-benzyloxy-5-methyl-7-methylsulfonyloxymethyl-4-oxo-4,5,6,7-tetrahydropyrazolo[1,5-a]pyrazine-2-carboxylate (57 mg, 0.14 mmol) in anhydrous DMF under an atmosphere of nitrogen was added piperidine (133 µL, 1.35 mmol). The reaction was stirred at room temperature for 2 hours, heated to 50° C. for 2 hours, and stirred at room temperature overnight. Purification by reverse phase chromatography on a C-18 column using a gradient elution of 95-5% H$_2$O (0.1% TFA)/CH$_3$CN (0.1% TFA) and collection and concentration of the appropriate fractions afforded the title product as a yellow residue. ES MS (M+H)=413.

Step 4: Methyl 3-hydroxy-5-methyl-4-oxo-7-(piperidin-1-ylmethyl)-4,5,6,7-tetrahydropyrazolo[1,5-a]pyrazine-2-carboxylate The title compound was prepared from methyl 3-benzyloxy-5-methyl-4-oxo-7-(piperidin-1-ylmethyl)-4,5,6,7-tetrahydropyrazolo[1,5-a]pyrazine-2-carboxylate using a hydrogenation procedure similar to that described in Example 1, Step 5 except that the reaction time totaled 1.5 hours. ES MS (M+H)=323.

Step 5: N-(4-fluorobenzyl)-3-hydroxy-5-methyl-4-oxo-7-(piperidin-1-ylmethyl)-4,5,6,7-tetrahydropyrazolo[1,5-a]pyrazine-2-carboxamide The title compound was prepared as the trifluoroacetate salt from methyl 3-hydroxy-5-methyl-4-oxo-7-(piperidin-1-ylmethyl)-4,5,6,7-tetrahydropyrazolo[1,5-a]pyrazine-2-carboxylate using a procedure similar to that described in Example 5, Step 3 except that the amine was used in excess (143 equivalents) and the reaction was heated to 90° C. for 3 hours. $^1$H NMR (400 MHz, d$_6$-DMSO) δ 9.60 (br s, 1H), 8.95 (br s, 1H), 8.70 (t, J=5.6 Hz, 1H), 7.37-7.34 (m, 2H), 7.19-7.14 (m, 2H), 5.07 (s, 1H), 4.47 (d, J=6.0 Hz, 2H), 3.99 (dd, J=3.2, 12.8 Hz, 1H), 3.80-3.77 (m, 1H), 3.65-3.50 (m, 4H), 3.00 (s, 3H), 1.99-1.84 (m, 2H), 1.79-1.58 (m, 4H), 1.42-1.18 (m, 2H); ES MS (M+H)=416.

EXAMPLE 10

5,7-Dimethyl-N-(4-fluorobenzyl)-3-hydroxy-4-oxo-4,5-dihydropyrazolo[1,5-a]pyrazine-2-carboxamide

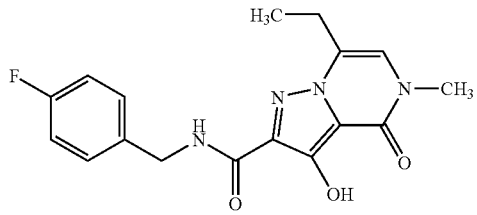

Step 1: Methyl 3-benzyloxy-5,7-dimethyl-4-oxo-4,5-dihydropyrazolo[1,5-a]pyrazine-2-carboxylate To a solution of methyl 3-benzyloxy-5-methyl-7-methylsulfonyloxymethyl-4-oxo-4,5,6,7-tetrahydropyrazolo[1,5-a]pyrazine-2-carboxylate (57 mg, 0.14 mmol) in anhydrous DMF under an atmosphere of nitrogen was added piperidine (133 µL, 1.35 mmol). The reaction was stirred at room temperature for 2 hours, heated to 50° C. for 2 hours, and stirred at room temperature overnight. Purification by reverse phase chromatography on a C-18 column using a gradient elution of 95-5% H$_2$O (0.1% TFA)/CH$_3$CN (0.1% TFA) and collection and concentration of the appropriate fractions afforded the title product. ES MS (M+H)=328.

Step 2: Methyl 3-hydroxy-5,7-dimethyl-4-oxo-4,5-dihydropyrazolo[1,5-a]pyrazine-2-carboxylate To a solution of methyl 3-benzyloxy-5,7-dimethyl-4-oxo-4,5-dihydropyrazolo[1,5-a]pyrazine-2-carboxylate (62 mg, 0.189 mmol) in CHCl$_3$ was added TFA (200 µL), and the reaction was stirred at room temperature for 2 hours. Following treatment with additional TFA (200 µL), the reaction was heated to 50° C. overnight. The solvent was removed in vacuo, and the resulting residue was purified by reverse phase chromatography on a C-18 column using a gradient elution of 95-5% H$_2$O (0.1% TFA)/CH$_3$CN (0.1% TFA). Collection and concentration of the appropriate fractions afforded the title product as a white solid. $^1$H NMR (400 MHz, d$_6$-DMSO) δ 6.44 (s, 1H), 4.03 (s, 3H), 3.48 (s, 3H), 2.44 (s, 3H); ES MS (M+Na)=260.

Step 3: 5,7-Dimethyl-N-(4-fluorobenzyl)-3-hydroxy-4-oxo-4,5-dihydropyrazolo[1,5-a]pyrazine-2-carboxamide The title compound was prepared from methyl 3-hydroxy-5,7-dimethyl-4-oxo-4,5-dihydropyrazolo[1,5-a]pyrazine-2-carboxylate using a procedure similar to that described in Example 5, Step 3 except that the amine was used in excess (103 equivalents) and the reaction was heated to 90° C. for 3 hours. $^1$H NMR (400 MHz, d$_6$-DMSO) δ 9.69 (s, 1H), 8.88 (t, J=6.0 Hz, 1H), 7.40-7.37 (m, 2H), 7.18-7.13 (m, 2H), 6.99 (s, 1H), 4.47 (d, J=6.0 Hz, 2H), 3.33 (s, 3H), 2.32 (s, 3H); HRMS (FT-ICR) C$_{16}$H$_{15}$FN$_4$O$_3$+H=331.1188; calculated 331.1201.

EXAMPLE 11

N-(4-Fluorobenzyl)-3-hydroxy-5-methyl-7-(4-methyl-1,3-thiazol-2-yl)-4-oxo-4,5,6,7-tetrahydropyrazolo[1,5-a]pyrazine-2-carboxamide

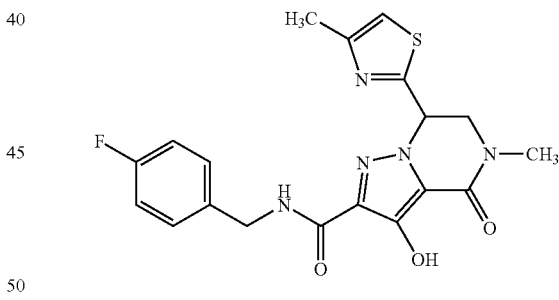

Step 1: Ethyl 7-aminocarbonyl-3-benzyloxy-5-methyl-4-oxo-4,5,6,7-tetrahydropyrazolo[1,5-a]pyrazine-2-carboxylate The title compound was prepared from 3-benzyloxy-2-ethoxycarbonyl-5-methyl-4-oxo-4,5,6,7-tetrahydropyrazolo[1,5-a]pyrazine-7-carboxylic acid using a procedure similar to that described in Example 2, Step 5 except that NH$_4$Cl was used in place of 4-fluorobenzylamine, and the reaction time totaled 18 hours. The mixture was partitioned between EtOAc and saturated aqueous NaHCO$_3$, and the aqueous layer was extracted twice more into EtOAc. The combined organic extracts were dried over Na$_2$SO$_4$, concentrated in vacuo, and azeotroped with toluene to afford the title product as a yellow solid. $^1$H NMR (400 MHz, d$_6$-DMSO) δ 7.69 (s, 1H), 7.55 (s, 1H), 7.50-7.49 (m, 2H), 7.29-7.32 (m, 3H), 5.19 (dd, J=10.8, 24.4 Hz, 2H), 4.28-4.24 (m, 3H), 4.16 (dd, J=5.2, 13.6 Hz, 1H), 3.86-3.83 (m, 1H), 2.99 (s, 3H), 1.27 (t, J=6.8 Hz, 3H); ES MS (M+H)=373.

Step 2: Ethyl 3-benzyloxy-7-cyano-5-methyl-4-oxo-4,5,6,7-tetrahydropyrazolo[1,5-a]pyrazine-2-carboxylate To a suspension of ethyl 7-aminocarbonyl-3-benzyloxy-5-methyl-4-oxo-4,5,6,7-tetrahydropyrazolo[1,5-a]pyrazine-2-carboxylate (273 mg, 0.733 mmol) in anhydrous THF under an atmosphere of nitrogen was added Burgess reagent ((methoxycarbonylsulfamoyl)triethylammonium hydroxide, inner salt, 349 mg, 1.47 mmol). The reaction was stirred at room temperature for 2 hours and then heated to 50° C. for 45 minutes. Additional Burgess reagent (4.89 g, 10.26 mmol) was added in portions and the reaction was heated to 60° C. overnight. The solvent was removed in vacuo, and the resulting residue was partitioned between saturated aqueous NH$_4$Cl and EtOAc. The layers were separated and the aqueous was extracted twice more with EtOAc. The combined organic extracts were dried over Na$_2$SO$_4$ and concentrated in vacuo to afford the title product. $^1$H NMR (400 MHz, d$_6$-DMSO) δ 7.49-7.47 (m, 2H), 7.40-7.31 (m, 3H), 6.23 (t, J=4.0 Hz, 1H), 5.23 (dd, J=10.8, 24.6 Hz, 2H), 4.33-4.23 (m, 3H), 4.13 (dd, J=3.8, 13.8 Hz, 1H), 3.09 (s, 3H), 1.27 (t, J=7.2 Hz, 3H); ES MS (M+H)=355.

Step 3: Ethyl 7-aminothionocarbonyl-3-benzyloxy-5-methyl-4-oxo-4,5,6,7-tetrahydropyrazolo[1,5-a]pyrazine-2-carboxylate Ethyl 3-benzyloxy-7-cyano-5-methyl-4-oxo-4,5,6,7-tetrahydropyrazolo[1,5-a]pyrazine-2-carboxylate (126 mg, 0.356 mmol) was dissolved in pyridine (3.9 mL) and Et$_3$N (1.6 mL) in a glass pressure tube and cooled to 0° C. The solution was treated with hydrogen sulfide gas, sealed, and allowed to warm to room temperature for 24 hours. The solution was again cooled to 0° C. and purged with nitrogen. The solvent was removed in vacuo, and the resulting orange residue was partitioned between saturated aqueous NH$_4$Cl and EtOAc. The aqueous layer was extracted three times more with EtOAc, and the combined organic extracts were dried over Na$_2$SO$_4$ and concentrated to an orange oil. $^1$H NMR (400 MHz, d$_6$-DMSO) δ 10.01 (s, 1H), 9.38 (s, 1H), 7.51-7.50 (m, 2H), 7.40-7.31 (m, 3H), 5.43 (dd, J=2.0, 5.2 Hz, 1H), 5.21 (dd, J=11.4, 24.8 Hz, 2H), 4.32-4.11 (m, 3H), 3.89 (dd, J=2.2, 14.0 Hz, 1H), 2.98 (s, 3H), 1.27 (t, J=7.0 Hz, 3H); ES MS (M+H)=389.

Step 4: Ethyl 3-benzyloxy-5-methyl-7-(4-methyl-1,3-thiazol-2-yl)-4-oxo-4,5,6,7-tetrahydropyrazolo[1,5-a]pyrazine-2-carboxylate To a solution of ethyl 7-aminothionocarbonyl-3-benzyloxy-5-methyl-4-oxo-4,5,6,7-tetrahydropyrazolo[1,5-a]pyrazine-2-carboxylate (69 mg, 0.178 mmol) in anhydrous MeOH was added chloroacetone (28 µL, 0.355 mmol). The reaction was heated to reflux for 1 hours, treated with additional chloroacetone (140 µL, 1.778 mmol), and again heated to reflux overnight. The solvent was removed in vacuo to afford the title product as a yellow oil. ES MS (M+H)=427.

Step 5: Ethyl 3-hydroxy-5-methyl-7-(4-methyl-1,3-thiazol-2-yl)-4-oxo-4,5,6,7-tetrahydropyrazolo[1,5-a]pyrazine-2-carboxylate Ethyl 3-benzyloxy-5-methyl-7-(4-methyl-1,3-thiazol-2-yl)-4-oxo-4,5,6,7-tetrahydropyrazolo[1,5-a]pyrazine-2-carboxylate (76 mg, 0.178 mmol) was treated with a 5% solution of HBr in AcOH, and the reaction was stirred for 2 hours at room temperature. The solvent was removed in vacuo and the residue azeotroped twice with MeOH to afford the title product as a bright orange solid. ES MS (M+H)=337.

Step 6: N-(4-Fluorobenzyl)-3-hydroxy-5-methyl-(4-methyl-1,3-thiazol-2-yl)-4-oxo-4,5,6,7-tetrahydropyrazolo[1,5-a]pyrazine-2-carboxamide The title compound was prepared from ethyl 3-hydroxy-5-methyl-7-(4-methyl-1,3-thiazol-2-yl)-4-oxo-4,5,6,7-tetrahydropyrazolo[1,5-a]pyrazine-2-carboxylate using a procedure similar to that described in Example 5, Step 3 to afford the title product as the trifluoroacetate salt. $^1$H NMR (400 MHz, d$_6$-DMSO) δ 8.89 (t, J=6.4 Hz, 1H), 7.36-7.33 (m, 2H), 7.27 (s, 1H), 7.16-7.12 (m, 2H), 6.07-6.06 (m, 1H), 4.46-4.29 (m, 3H), 3.98 (dd, J=2.0, 13.6 Hz, 1H), 2.94 (s, 3H), 2.34 (s, 3H); HRMS (FT-ICR) C$_{19}$H$_{18}$FN$_5$O$_3$S+H=416.1188; calculated 416.1187.

EXAMPLE 12

N-(4-Fluorobenzyl)-3-hydroxy-5-methyl-(2-methyl-1,3-thiazol-4-yl)-4-oxo-4,5,6,7-tetrahydropyrazolo[1,5-a]pyrazine-2-carboxamide

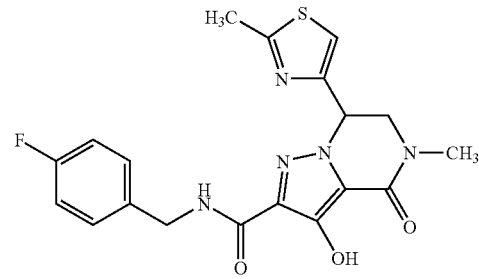

Step 1: Ethyl 3-benzyloxy-7-chlorocarbonyl-5-methyl-4-oxo-4,5,6,7-tetrahydropyrazolo[1,5-a]pyrazine-2-carboxylate To a suspension of 3-benzyloxy-2-ethoxycarbonyl-5-methyl-4-oxo-4,5,6,7-tetrahydropyrazolo[1,5-a]pyrazine-7-carboxylic acid (250 mg, 0.670 mmol) in anhydrous CH$_2$Cl$_2$ at 0° C. were added 2M oxalyl chloride in CH$_2$Cl$_2$ (1.339 mL, 2.678 mmol) and DMF (1 drop). The reaction was stirred at 0° C. for 30 minutes and allowed to warm to room temperature for 1 hour. The mixture was concentrated in vacuo and azeotroped twice with anhydrous CH$_2$Cl$_2$ to afford the title product. ES MS (M+H)=392.

Step 2: Ethyl 3-benzyloxy-7-diazoacetyl-5-methyl-4-oxo-4,5,6,7-tetrahydropyrazolo[1,5-a]pyrazine-2-carboxylate To a stirring biphasic mixture of 40% aqueous KOH (20 mL) and Et$_2$O (10 mL) at 0° C. was slowly added N-methyl- N-nitroso-N'-nitroguanidine (492 mg, 3.34 mmol). The mixture was stirred for 15 minutes, and the Et₂O layer was transferred to a solution of ethyl 3-benzyloxy-7-chlorocarbonyl-5-methyl-4-oxo-4,5,6,7-tetrahydropyrazolo[1,5-a]pyrazine-2-carboxylate (262 mg, 0.669 mmol) in CH₂Cl₂ (10 mL). The reaction was stirred at room temperature for 30 minutes, and the solvent was removed in vacuo to afford the title product. ES MS (M+H)=398.

Step 3: Ethyl 3-benzyloxy-7-chloroacetyl-5-methyl-4-oxo-4,5,6,7-tetrahydropyrazolo[1,5-a]pyrazine-2-carboxylate To a solution of ethyl 3-benzyloxy-7-diazoacetyl-5-methyl-4-oxo-4,5,6,7-tetrahydropyrazolo[1,5-a]pyrazine-2-carboxylate (90 mg, 0.226 mmol) in Et₂O (5 mL) and anhydrous CH₂Cl₂ (5 mL) was added 1.0M HCl in Et₂O (272 µL, 0.272 mmol). The reaction was stirred at room temperature for 15 minutes, and the solvent was removed in vacuo to afford the title product as a yellow solid. $^1$H NMR (400 MHz, d₆-DMSO) δ 7.49-7.48 (m, 2H), 7.39-7.30 (m, 3H), 7.12 (br s, 1H), 6.03 (s, 1H), 5.57 (s, 1H), 5.22 (dd, J=11.4, 26.0 Hz, 2H), 4.28-4.24 (m, 2H), 4.09 (dd, J=4.6, 13.4 Hz, 1H), 3.88 (dd, J=4.6, 13.4 Hz, 1H), 2.98 (s, 3H), 1.26 (t, J=7.2, 3H); ES MS (M+Na)=428.

Step 4: Ethyl 3-benzyloxy-5-methyl-7-(2-methyl-1,3-thiazol-4-yl)-4-oxo-4,5,6,7-tetrahydropyrazolo[1,5-a]pyrazine-2-carboxylate To a suspension of ethyl 3-benzyloxy-7-chloroacetyl-5-methyl-4-oxo-4,5,6,7-tetrahydropyrazolo[1,5-a]pyrazine-2-carboxylate (90 mg, 0.222 mmol) in anhydrous MeOH (5 mL) was added thioacetamine (20 mg, 0.266 mmol). The reaction was heated to reflux for 1 hour, and the solvent was removed in vacuo. The resulting residue was purified by reverse phase chromatography on a C-18 column using a gradient elution of 95-5% H₂O (0.1% TFA)/CH₃CN (0.1% TFA). Collection and concentration of the appropriate fractions afforded the title product as the trifluoroacetate salt. $^1$H NMR (400 MHz, d₆-DMSO) δ 7.50-7.48 (m, 2H), 7.39-7.20 (m, 3H), 7.02 (s, 1H), 5.87 (t, J=4.4, 1H), 5.24 (dd, J=11.8, 25.2 Hz, 2H), 4.32-4.21 (m, 3H), 4.17 (dd, J=3.8, 13.6 Hz, 1H), 2.96 (s, 3H), 2.64 (s, 3H), 1.25 (t, J=7.0 Hz, 3H); ES MS (M+H)=427.

Step 5: Ethyl 3-hydroxy-5-methyl-7-(2-methyl-1,3-thiazol-4-yl)-4-oxo-4,5,6,7-tetrahydropyrazolo[1,5-a]pyrazine-2-carboxylate To a solution of ethyl 3-(benzyloxy)-5-methyl-7-(2-methyl-1,3-thiazol-4-yl)-4-oxo-4,5,6,7-tetrahydropyrazolo[1,5-a]pyrazine-2-carboxylate (64 mg, 0.150 mmol) in anhydrous CH₂Cl₂ at 0° C. was added 2.0M boron tribromide in CH₂Cl₂ (112 µL, 0.225 mmol). The reaction was stirred at room temperature overnight, and the solvent was removed in vacuo. The resulting residue was dissolved in 0.025M H₂SO₄ in EtOH (1.2 mL) and heated to reflux overnight. Purification by reverse phase chromatography on a C-18 column using a gradient elution of 95-5% H₂O (0.1% TFA)/CH₃CN (0.1% TFA) and collection and concentration of the appropriate fractions afforded the title product as a viscous oil. ES MS (M+H)=337.

Step 6: N-(4-Fluorobenzyl)-3-hydroxy-5-methyl-(2-methyl-1,3-thiazol-4-yl)-4-oxo-4,5,6,7-tetrahydropyrazolo[1,5-a]pyrazine-2-carboxamide The title compound was prepared from ethyl 3-hydroxy-5-methyl-7-(2-methyl-1,3-thiazol-4-yl)-4-oxo-4,5,6,7-tetrahydropyrazolo[1,5-a]pyrazine-2-carboxylate (27 mg, 0.080 mmol) using a procedure similar to that described in Example 5, Step 3, except that MeOH was used in place of toluene and the reaction was heated to 100° C. for 2 hours and to 120° C. for 2 hours. Purification by reverse phase chromatography on a C-18 column using a gradient elution of 95-5% H₂O (0.1% TFA)/CH₃CN (0.1% TFA) and collection and concentration of the appropriate fractions afforded the title product as a the trifluoroacetate salt. $^1$H NMR (400 MHz, d₆-DMSO) δ 8.83 (t, J=6.6 Hz, 1H), 7.36-7.33 (m, 2H), 7.16-7.11 (m, 2H), 7.01 (s, 1H), 5.77 (t, J=4.0 Hz, 1H), 4.40 (qd, J=6.6, 15.2, 21.6 Hz, 2H), 4.16 (dd, J=4.6, 13.6 Hz, 1H), 3.92 (dd, J=3.8, 13.6 Hz, 1H), 2.90 (s, 3H), 2.62 (s, 3H); HRMS (FT-ICR) C₁₉H₁₈FN₅O₃S+H=416.1174; calculated 416.1187.

EXAMPLE 13

2-[4-fluorobenzyl(methyl)aminocarbonyl]-3-hydroxy-5-methyl-4-oxo-4,5,6,7-tetrahydropyrazolo[1,5-a]pyrazine-2-carboxamide

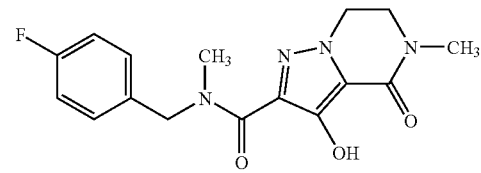

Step 1: Methyl 3-benzyloxy-5-methyl-4-oxo-4,5,6,7-tetrahydropyrazolo[1,5-a]pyrazine-2-carboxylate To a solution of methyl 3-benzyloxy-4-oxo-4,5,6,7-tetrahydropyrazolo[1,5-a]pyrazine-2-carboxylate (300 mg, 0.966 mmol) in DMF (5 mL) was added iodomethane (74 µL, 1.20 mmol). The solution was cooled to 0° C., treated with NaH (36 mg, 1.49 mmol, 95% dispersion in oil), and stirred for 10 minutes. The reaction was removed from the ice bath and allowed to gradually warm to room temperature. The mixture was partitioned between EtOAc and brine, and the organic extract was dried over Na₂SO₄ and concentrated in vacuo. Purification by reverse phase chromatography on a C-18 column using a gradient elution of 95-5% H₂O (0.1% TFA)/CH₃CN (0.1% TFA) and collection and concentration of the appropriate fractions afforded the title product. $^1$H NMR (400 MHz, CDCl₃) δ 7.54-7.53 (m, 2H), 7.37-7.28 (m, 3H), 5.36 (s, 2H), 4.38-4.41 (t, 2H), 3.92 (s, 3H), 3.76-3.72 (t, 2H), 3.16 (s, 3H); ES MS (M+1)=316.

Step 2: 3-Benzyloxy-5-methyl-4-oxo-4,5,6,7-tetrahydropyrazolo[1,5-a]pyrazine-2-carboxylic acid To a solution of methyl 3-benzyloxy-5-methyl-4-oxo-4,5,6,7-tetrahydropyrazolo[1,5-a]pyrazine-2-carboxylate (221 mg, 0.701 mmol) in MeOH (5 mL) was added 1N aqueous NaOH (2 mL, 2 mmol). The reaction was stirred for several hours at room temperature and treated with 1N aqueous HCl (2 mL, 2 mmol). The solvents were removed in vacuo to afford the title product. ¹H NMR (400 MHz, CD₃OD) δ 7.51-7.49 (m, 2H), 7.54-7.26 (m, 3H), 5.26 (s, 2H), 4.39-4.36 (t, 2H), 3.82-3.72 (t, 2H), 3.12 (s, 3H); ES MS (M+1)=302.

Step 3: 3-Benzyloxy-2-[4-fluorobenzyl(methyl)aminocarbonyl]-5-methyl-4-oxo-4,5,6,7-tetrahydropyrazolo[1,5-a]pyrazine To a solution of 3-benzyloxy-5-methyl-4-oxo-4,5,6,7-tetrahydropyrazolo[1,5-a]pyrazine-2-carboxylic acid (50 mg, 0.166 mmol) in DMF (2 mL) were added EDC (32 mg, 0.166 mmol), HOBT (27 mg, 0.199 mmol), and 4-fluoro-N-methylbenzylamine (23 mg, 0.166 mmol). The reaction was stirred at room temperature overnight and partitioned between EtOAc and brine. The aqueous layer was extracted several times with EtOAc, and the combined organic extracts were dried over Na₂SO₄ and concentrated in vacuo. Purification by reverse phase chromatography on a C-18 column using a gradient elution of 95-5% H₂O (0.1% TFA)/CH₃CN (0.1% TFA) and collection and concentration of the appropriate fractions afforded the title product. ¹H NMR (400 MHz, CDCl₃) δ 7.44-7.42 (m, 1H), 7.38-7.29 (m, 4H), 7.16-7.12 (m, 1H), 6.98-6.92 (m, 3H), 5.30-5.24 (m, 4H), 4.39-4.34 (m, 2H), 3.80-3.73 (m, 2H), 3.19-3.17 (d, 3H), 2.89-2.86 (d, 3H); ES MS (M+1)=423.

Step 4: 2-[4-Fluorobenzyl(methyl)aminocarbonyl]-3-hydroxy-5-methyl-4-oxo-4,5,6,7-tetrahydropyrazolo[1,5-a]pyrazine The title compound was prepared from 3-benzyloxy-2-[4-fluorobenzyl(methyl)aminocarbonyl]-5-methyl-4-oxo-4,5,6,7-tetrahydropyrazolo[1,5-a]pyrazine using a hydrogenation procedure similar to that described in Example 1, Step 5, except that the reaction time totaled 45 minutes. ¹H NMR (400 MHz, d₆-DMSO) δ 7.35-7.29 (m, 2H), 7.19-7.14 (m, 2H), 5.76 (s, 2H), 4.21 (br s, 2H), 3.66 (br s, 2H), 3.32 (s, 3H), 2.95 (s, 3H); ES MS (M+1)=333.

EXAMPLE 14

3-Hydroxy-5-methyl-4-oxo-2-[(1,2,3,4-tetrahydro-isoquinolin-2-yl)carbonyl]-4,5,6,7-tetrahydropyrazolo[1,5-a]pyrazine

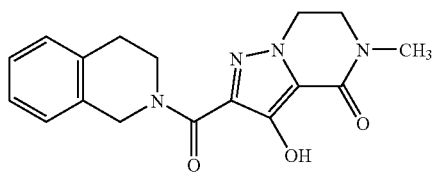

Step 1: 3-Benzyloxy-5-methyl-4-oxo-2-[(1,2,3,4-tetrahydro-isoquinolin-2-yl)carbonyl]-4,5,6,7-tetrahydropyrazolo[1,5-a]pyrazine To a solution of 3-benzyloxy-5-methyl-4-oxo-4,5,6,7-tetrahydropyrazolo[1,5-a]pyrazine-2-carboxylic acid (60 mg, 0.199 mmol) in DMF (2 mL) under an atmosphere of nitrogen was added HATU (152 mg, 0.398 mmol) and 1,2,3,4-tetrahydroisoquinoline (32 mg, 0.239 mmol). The reaction was stirred at room temperature for 1 hour. Purification by reverse phase chromatography on a C-18 column using a gradient elution of 95-5% H₂O (0.1% TFA)/CH₃CN (0.1% TFA) and collection and concentration of the appropriate fractions afforded the title product. ¹H NMR (400 MHz, CDCl₃) δ 7.69-7.58 (m, 1H), 7.53-7.48 (m, 1H), 7.33-7.30 (m, 1H), 7.22-7.10 (m, 4H), 7.08-7.06 (d, 1H), 6.94-6.92 (d, 1H), 5.24-5.22 (d, 2H), 4.81 (s, 1H), 4.60 (s, 1H), 4.39-4.35 (t, 2H), 3.90-3.87 (m, 1H), 3.78-3.75 (t, 2H), 3.64-3.61 (t, 1H), 3.18 (s, 3H), 2.93-2.90 (t, 1H), 2.82-2.79 (t, 1H); ES MS (M+1) =417.

Step 2: 3-Hydroxy-5-methyl-4-oxo-2-[(1,2,3,4-tetrahydro-isoquinolin-2-yl)carbonyl]-4,5,6,7-tetrahydropyrazolo[1,5-a]pyrazine 3-Benzyloxy-5-methyl-4-oxo-2-[(1,2,3,4-tetrahydro-isoquinolin-2-yl)carbonyl]-4,5,6,7-tetrahydropyrazolo[1,5-a]pyrazine (46 mg, 0.110 mmol) was dissolved in a 30% solution of HBr in AcOH, and the reaction was stirred at room temperature for 30 minutes. The solvent was removed in vacuo, and purification of the product was achieved by reverse phase chromatography on a C-18 column using a gradient elution of 95-5% H₂O (0.1% TFA)/CH₃CN (0.1% TFA). Collection and concentration of the appropriate fractions afforded the title compound. ¹H NMR (400 MHz, d₆-DMSO) δ 9.88 (s, 1H), 7.24-7.13 (m, 4H), 5.19 (br s, 1H), 4.78 (br s, 1H), 4.37-4.34 (t, 2H), 4.20 (br s, 1H), 3.85 (br s, 1H), 3.76-3.73 (t, 2H), 2.98 (s, 3H), 2.90 (br s, 2H); ES MS (M+1)=327.

EXAMPLES 15-19

The compounds listed in the following table were synthesized in two steps from 3-benzyloxy-5-methyl-4-oxo-4,5,6,7-tetrahydropyrazolo[1,5-a]pyrazine-2-carboxylic acid and the appropriate amine using procedures similar to those of Steps 3 and 4 of Example 13 and Steps 1 and 2 of Example 14. Method A refers to the procedure of Step 1 of Example 13, Method B is Step 1 of Example 14, Method C is Step 2 of Example 13, and Method D is Step 2 of Example 14.

| Example | Compound (Method of Preparation) | Data |
|---|---|---|
| 15 | N-[4-Fluoro-2-(methylsulfonyl)benzyl]-3-hydroxy-5-methyl-4-oxo-4,5,6,7-tetrahydropyrazolo[1,5-a]pyrazine-2-carboxamide (Methods A and C) | $^1$H NMR (400 MHz, CD$_{3}$OD) δ 7.74-7.72 (d, 2H), 7.42 (br s, 1 H), 5.48 (s, 2 H), 4.23 (br s, 2 H), 3.69 (br s, 2 H), 3.33 (s, 6 H); ES MS (M + 1) = 397. |
| 16 | 3-Hydroxy-5-methyl-4-oxo-2-[(2-phenylpyrrolidin-1-yl)carbonyl]-4,5,6,7-tetrahydropyrazolo[1,5-a]pyrazine (Methods B and D) | $^1$H NMR (400 MHz, CD$_{3}$OD) δ 7.33-7.12 (m, 5 H), 4.42-4.39 (t, 2 H), 4.33-4.18 (m, 1 H), 4.08-3.89 (m, 1 H), 3.84-3.80 (t, 2 H), 3.68-3.64 (m, 1 H), 3.10 & 3.02 (s, rotamers, 3 H), 2.47-2.33 (m, 1 H), 2.06-1.86 (m, 3 H); ES MS (M + 1) = 341. |
| 17 | 3-Hydroxy-5-methyl-4-oxo-2-{[quinoxalin-6-ylmethyl(methyl)amino]carbonyl}-4,5,6,7-tetrahydropyrazolo[1,5-a]pyrazine (Methods B and D) | $^1$H NMR (400 MHz, d$_6$-DMSO) δ 8.95-8.93 (m, 2 H), 8.12-8.10 (d, 1 H), 7.98-7.95 (d, 1 H), 7.81-7.78 (m, 1 H), 5.42 (br s, 1 H), 4.97 (s, 2 H), 4.37-4.34 (t, 1 H), 4.28-4.25 (t, 1 H), 3.76-3.67 (m, 2 H), 2.98 & 2.95 (s, rotamers, 3 H), 2.51 (s, 3 H); ES MS (M + 1) = 367 |
| 18 | 2-[Benzyl(2-hydroxyethyl)aminocarbonyl]-3-hydroxy-5-methyl-4-oxo-4,5,6,7-tetrahydropyrazolo[1,5-a]pyrazine (Methods B and C) | $^1$H NMR (400 MHz, d$_6$-DMSO) δ 7.36-7.26 (m, 5 H), 5.76 (s, 2 H), 5.26 (br s, 1 H), 4.71 (br s, 2 H), 4.23 (br s, 2 H), 3.67 (br s, 2 H), 3.56 (br s, 2 H), 2.95 (s, 3 H); ES MS (M + 1) = 345. |
| 19 | 2-{Benzyl[2-(dimethylamino)ethyl]aminocarbonyl}-3-hydroxy-5-methyl-4-oxo-4,5,6,7-tetrahydropyrazolo[1,5-a]pyrazine (Methods B and D) | $^1$H NMR (400 MHz, d$_6$-DMSO) δ 7.40-7.28 (m, 5 H), 5.20 (s, 1 H), 4.72 (s, 1 H), 4.38-4.35 (t, 1 H), 4.31-4.28 (t, 1 H), 4.07-4.03 (m, 1 H), 3.77-3.70 (m, 2 H), 3.65-3.61 (t, 1 H), 3.40 (br s, 1 H), 3.32-3.28 (m, 1 H), 2.99 & 2.96 (s, rotamers, 3 H), 2.86-2.76 (m, 6 H); ES MS (M + 1) = 372. |

EXAMPLE 20

N-(3,4-Dichlorobenzyl)-3-hydroxy-5-[2-(4-morpholinyl)-2-oxoethyl]-4-oxo-4,5,6,7-tetrahydropyrazolo[1,5-a]pyrazine-2-carboxamide

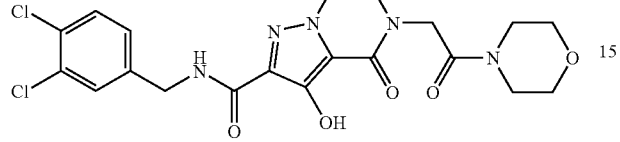

Step 1: Methyl 3-benzyloxy-5-[(2-morpholin-4-yl)-2-oxoethyl]-4-oxo-4,5,6,7-tetrahydropyrazolo[1,5-a]pyrazine-2-carboxylate The title compound was prepared from methyl 3-benzyloxy-4-oxo-4,5,6,7-tetrahydropyrazolo[1,5-a]pyrazine-2-carboxylate using a procedure similar to Example 13, Step 1, except that 4-(2-chloroacetyl)morpholine was used in place of iodomethane. $^1$H NMR (400 MHz, CDCl$_3$) δ 7.53-7.50 (d, 2H), 7.37-7.28 (m, 3H), 5.31-5.30 (m, 3H), 4.49-4.46 (t, 2H), 4.41 (s, 2H), 3.93 (s, 3H), 3.88-3.84 (t, 2H), 3.77-3.71 (m, 3H), 3.65-3.62 (t, 2H), 3.55-3.52 (t, 2H); ES MS (M+1)=429.

Step 2: Methyl 3-hydroxy-5-[(2-morpholin-4-yl)-2-oxoethyl]-4-oxo-4,5,6,7-tetrahydropyrazolo[1,5-a]pyrazine-2-carboxylate The title compound was prepared from methyl 3-benzyloxy-5-[(2-morpholin-4-yl)-2-oxoethyl]-4-oxo-4,5,6,7-tetrahydropyrazolo[1,5-a]pyrazine-2-carboxylate using a hydrogenation procedure similar to Example 1, Step 5, except that the reaction time totaled 45 minutes. ES MS (M+1)=339.

Step 3: N-(3,4-Dichlorobenzyl)-3-hydroxy-5-[2-(4-morpholinyl)-2-oxoethyl]-4-oxo-4,5,6,7-tetrahydropyrazolo[1,5-a]pyrazine-2-carboxamide Methyl 3-hydroxy-5-[(2-morpholin-4-yl)-2-oxoethyl]-4-oxo-4,5,6,7-tetrahydropyrazolo[1,5-a]pyrazine-2-carboxylate (15 mg, 0.044 mmol) was dissolved in 3,4-dichlorobenzylamine (1.5 mL) and heated to 90° C. for 30 minutes. Purification by reverse phase chromatography on a C-18 column using a gradient elution of 95-5% H$_2$O (0.1% TFA)/CH$_3$CN (0.1% TFA) and collection and concentration of the appropriate fractions afforded the title product. $^1$H NMR (400 MHz, d$_6$-DMSO) δ 8.89-8.86 (t, 1H), 7.55-7.51 (m, 2H), 7.27-7.25 (d, 1H), 4.40-4.38 (d, 2H), 4.33-4.29 (m, 4H), 3.84 (br s, 1H), 3.74-3.71 (t, 2H), 3.58-3.52 (m, 4H), 3.42-3.39 (m, 4H); ES MS (M+1)=482.

EXAMPLE 21

5-Cyclopropylmethyl-N-(3,4-dichlorobenzyl)-3-hydroxy-4-oxo-4,5,6,7-tetrahydropyrazolo[1,5-a]pyrazine-2-carboxamide

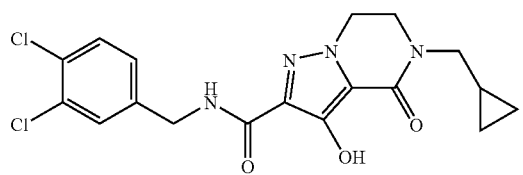

The title compound was prepared as the from methyl 3-benzyloxy-4-oxo-4,5,6,7-tetrahydropyrazolo[1,5-a]pyrazine-2-carboxylate using the three step procedure of Example 20, except that cyclopropylmethyl bromide was used in place of iodomethane in Step 1. $^1$H NMR (400 MHz, d$_6$-DMSO) δ 8.90-8.87 (m, 1H), 7.60-7.54 (m, 2H), 7.31-7.28 (m, 1H), 4.43-4.41 (d, 2H), 4.34-4.31 (t, 2H), 3.85-3.81 (t, 2H), 3.34-3.32 (d, 2H), 1.15-0.97 (m, 1H), 0.45-0.43 (d, 2H), 0.28-0.25 (d, 2H); ES MS (M+1)=409.

EXAMPLE 22

N-(3,4-Dichlorobenzyl)-3-hydroxy-5-[2-(4-morpholinyl)ethyl]-4-oxo-4,5,6,7-tetrahydropyrazolo[1,5-a]pyrazine-2-carboxamide

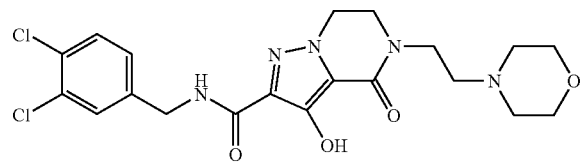

The title compound was prepared as the trifluoroacetate salt from methyl 3(benzyloxy-4-oxo-4,5,6,7-tetrahydropyrazolo[1,5-a]pyrazine-2-carboxylate using the three step procedure of Example 20 except that N-(2-chloroethyl)morpholine was used in place of iodomethane in Step 1. $^1$H NMR (400 MHz, d$_6$-DMSO) δ 8.92-8.88 (t, 1H), 7.54-7.49 (m, 2H), 7.26-7.23 (m, 1H), 4.40-4.38 (d, 2H), 4.36-4.32 (t, 2H), 3.98-3.52 (m, 11H), 3.36 (br s, 2H), 3.14-3.10 (m, 2H); ES MS (M+1)=468.

EXAMPLE 23

5-(4-Fluorobenzyl)-3-hydroxy-N-[2-(4-morpholinyl)ethyl]-4-oxo-4,5,6,7-tetrahydropyrazolo[1,5-a]pyrazine-2-carboxamide

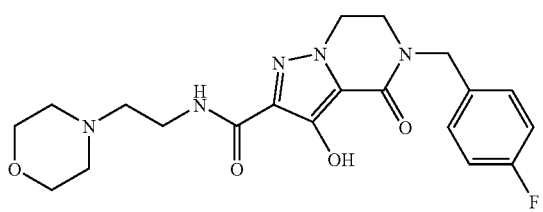

Step 1: Methyl 3-benzyloxy-5-(4-fluorobenzyl)-4-oxo-4,5,6,7-tetrahydropyrazolo[1,5-a]pyrazine-2-carboxylate The title compound was prepared from methyl 3-benzyloxy-4-oxo-4,5,6,7-tetrahydropyrazolo[1,5-a]pyrazine-2-carboxylate using a procedure similar to that found in Example 13, Step 1, except that 4-fluorobenzyl bromide was used in place of iodomethane. Purification was achieved by flash column chromatography on silica gel using a gradient elution of 0-6% MeOH/CH$_2$Cl$_2$, and collection and concentration of appropriate fractions afforded the title product. $^1$H NMR (400 MHz, CDCl$_3$) δ 7.57-7.55 (d, 2H), 7.38-7.29 (m, 5H), 7.08-7.03 (m, 2H), 5.40 (s, 2H), 4.74 (s, 2H), 4.33-4.30 (t, 2H), 3.93 (s, 3H), 3.63-3.59 (t, 2H); ES MS (M+1)=410.

Step 2: 3-Benzyloxy-5-(4-fluorobenzyl)-4-oxo-4,5,6,7-tetrahydropyrazolo[1,5-a]pyrazine-2-carboxylic acid The title compound was prepared from methyl 3-benzyloxy-5-(4-fluorobenzyl)-4-oxo-4,5,6,7-tetrahydropyrazolo[1,5-a]pyrazine-2-carboxylate using a procedure similar to that found in Example 13, Step 2. $^1$H NMR (400 MHz, CD$_3$OD) δ 7.50-7.47 (m, 2H), 7.40-7.36 (m, 2H), 7.32-7.26 (m, 3H), 7.11-7.07 (m, 2H), 5.13 (s, 2H), 4.74 (s, 2H), 4.33-4.30 (t, 2H), 3.70-3.67 (t, 2H).

Step 3: 3-Benzyloxy-5-(4-fluorobenzyl)-N-[(2-morpholin-4-yl)ethyl]-4-oxo-4,5,6,7-tetrahydropyrazolo[1,5-a]pyrazine-2-carboxamide The title compound was prepared as the trifluoroacetate salt from 3-benzyloxy-5-(4-fluorobenzyl)-4-oxo-4,5,6,7-tetrahydropyrazolo[1,5-a]pyrazine-2-carboxylic acid using a procedure similar to that found in Example 15, Step 1, except that 4-(2-aminoethyl)morpholine was used in place of 1,2,3,4-tetrahydroisoquinoline. $^1$H NMR (400 MHz, CDCl$_3$) δ 7.70-7.67 (t, 1H), 7.48-7.46 (m, 2H), 7.36-7.27 (m, 5H), 7.08-7.04 (m, 2H), 5.46 (s, 2H), 5.30 (s, 2H), 4.74 (s, 2H), 4.28-4.25 (t, 2H), 3.96 (br s, 4H), 3.78-3.68 (m, 4H), 3.61-3.58 (t, 2H), 3.30-3.26 (t, 2H); ES MS (M+1)=508.

Step 4: 5-(4-Fluorobenzyl)-3-hydroxy-N-[2-(4-morpholinyl)ethyl]-4-oxo-4,5,6,7-tetrahydropyrazolo[1,5-a]pyrazine-2-carboxamide The title compound was prepared as the trifluoroacetate salt from 3-benzyloxy-5-(4-fluorobenzyl)-N-[(2-morpholin-4-yl)ethyl]-4-oxo-4,5,6,7-tetrahydropyrazolo[1,5-a]pyrazine-2-carboxamide using a hydrogenation procedure similar to that found in Example 1, Step 5, except that the reaction time totaled 40 minutes. $^1$H NMR (400 MHz, CD$_3$OD) δ 7.41-7.38 (m, 2H), 7.12-7.07 (m, 2H), 5.49 (s, 2H), 4.72 (br s, 2H), 4.28 (br s, 2H), 3.90 (br s, 6H), 3.75-3.71 (m, 6H); ES MS (M+1)=418.

EXAMPLES 24-28

The following compounds were synthesized in two steps from 3-benzyloxy-5-(4-fluorobenzyl)-4-oxo-4,5,6,7-tetrahydropyrazolo[1,5-a]pyrazine-2-carboxylic acid and the appropriate amine using procedures similar to those of Steps 3 and 4 of Example 23 (Method A) or similar to Step 3 of Example 23 and Step 2 of Example 14 (Method B).

| Example | Compound (Method of Preparation) | Data |
| --- | --- | --- |
| 24 | N-Butyl-5-(4-fluorobenzyl)-3-hydroxy-4-oxo-4,5,6,7-tetrahydropyrazolo[1,5-a]pyrazine-2-carboxamide (Method B) | $^1$H NMR (400 MHz, CD$_{3OD}$) δ 7.40-7.36 (m, 2 H), 7.10-7.06 (m, 2 H), 4.72 (s, 2 H), 4.31-4.28 (t, 2 H), 3.72-3.68 (t, 2 H), 3.39-3.35 (t, 2 H), 1.62-1.54 (m, 2 H), 1.45-1.35 (m, 2 H), 0.98-0.94 (t, 3 H); ES MS (M + 1) = 361. |
| 25 | 5-(4-Fluorobenzyl)-3-hydroxy-4-oxo-N-(4-piperidinyl)-4,5,6,7-tetrahydropyrazolo[1,5-a]pyrazine-2-carboxamide (Method B) | $^1$H NMR (400 MHz, CD$_{3OD}$) δ 7.40-7.37 (m, 2 H), 7.11-7.06 (m, 2 H), 5.24 (br s, 1 H), 4.79-4.72 (m, 3 H), 4.33-4.29 (t, 2 H), 3.73-3.70 (t, 2 H), 3.49-3.40 (m, 1 H), 2.91 (br s, 1 H), 2.10 (br s, 2 H), 1.60 (br s, 2 H); ES MS (M + 1) = 388. |
| 26 | N-[2-(Dimethylamino)-2-oxoethyl]-5-(4-fluorobenzyl)-3-hydroxy-4-oxo-N-(4-piperidinyl)-4,5,6,7-tetrahydropyrazolo[1,5-a]pyrazine-2-carboxamide (Method A) | $^1$H NMR (400 MHz, CD$_{3OD}$) δ 7.42-7.38 (m, 2 H), 7.12-7.07 (m, 2 H), 4.73 |

| Example | Compound (Method of Preparation) | Data |
|---|---|---|
| | | (s, 2 H), 4.34-4.31 (t, 2 H), 4.26 (s, 2 H), 3.73-3.70 (t, 2 H), 3.08 (s, 3 H), 2.99 (s, 3 H); ES MS (M + 1) = 390. |
| 27 | 2-(Azetidin-1-ylcarbonyl)-5-(4-fluorobenzyl)-3-hydroxy-4-oxo-4,5,6,7-tetrahydropyrazolo[1,5-a]pyrazine (Method A) | $^1$H NMR (400 MHz, CD$_{3OD}$) δ 7.40-7.36 (m, 2 H), 7.11-7.06 (m, 2 H), 4.71 (s, 2 H), 4.60-4.56 (t, 2 H), 4.31-4.28 (t, 2 H), 4.21-4.17 (t, 2 H), 3.72-3.69 (t, 2 H), 2.45-2.37 (m, 2 H); ES MS (M + 1) = 345. |
| 28 | 5-(4-Fluorobenzyl)-3-hydroxy-2-(morpholin-4-ylcarbonyl)-4-oxo-4,5,6,7-tetrahydropyrazolo[1,5-a]pyrazine (Method A) | $^1$H NMR (400 MHz, d$_6$-DMSO) δ 9.98 (br s, 1 H), 7.41-7.37 (m, 2 H), 7.20-7.16 (m, 2 H), 4.64 (s, 2 H), 4.32-4.28 (t, 2 H), 4.00 (br s, 2 H), 3.68-3.63 (m, 8 H); ES MS (M + 1) = 375. |

EXAMPLE 29

N-(4-Fluorobenzyl)-3-hydroxy-4-oxo-5,6,7,8-tetrahydro-4H-pyrazolo[1,5-a][1,4]diazepine-2-carboxamide

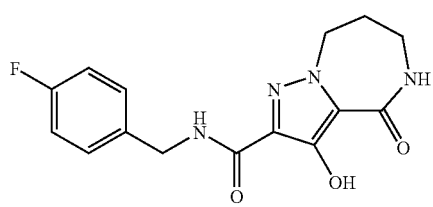

Step 1: Dimethyl 4-benzyloxy-1-(3-bromopropyl)-1H-pyrazole-3,5-dicarboxylate To a solution of dimethyl 4-benzyloxy-1H-pyrazole-3,5-dicarboxylate (200 mg, 0.689 mmol) in DMF (3 mL) under an atmosphere of nitrogen at 0° C. was added dibromopropane (211 µL, 2.067 mmol) and Cs$_2$CO$_3$ (269 mg, 0.827 mmol). The ice bath was removed, and the reaction was stirred at room temperature overnight. The solvent was removed in vacuo, and the resulting residue was partitioned between EtOAc and water. The aqueous layer was extracted into EtOAc once, and the combined organic extracts were washed with brine, dried over Na$_2$SO$_4$, and concentrated in vacuo. the residue was purified by flash column chromatography on silica gel using a 0-50% EtOAc/hexanes gradient elution. Collection and concentration of the appropriate fractions afforded the compound. $^1$H NMR (400 MHz, CDCl$_3$) δ 7.47-7.44 (m, 2H), 7.40-7.34 (m, 3M), 5.13 (s, 2H), 4.71-4.67 (t, 2H), 3.96 (s, 3H), 3.87 (s, 3H), 3.39-3.36 (t, 2H), 2.45-2.38 (dt, 2H); ES MS (M+1)=412.

Step 2: Dimethyl 1-(3-azidopropyl)-4-benzyloxy-1H-pyrazole-3,5-dicarboxylate To a solution of dimethyl 4(benzyloxy-1-(3-bromopropyl)-1H-pyrazole-3,5-dicarboxylate (176 mg, 0.428 mmol) in DMF (2 mL) was added sodium azide (83 mg, 1.284 mmol). The reaction was stirred at room temperature for 1 hour, and the solvent was removed in vacuo. The resulting residue was partitioned between CH$_2$Cl$_2$ and brine, and the aqueous layer was extracted into CH$_2$Cl$_2$ once more. The combined organic extracts were dried over Na$_2$SO$_4$ and concentrated to afford the title product. $^1$H NMR (400 MHz, CDCl$_3$) δ 7.47-7.44 (m, 2H), 7.40-7.34 (m, 3H), 5.13 (s, 2H), 4.65-4.62 (t, 2H), 3.96 (s, 3H), 3.87 (s, 3H), 3.35-3.31 (t, 2H), 2.15-2.08 (dt, 2H).

Step 3: Methyl 3-benzyloxy-4-oxo-5,6,7,8-tetrahydro-4H-pyrazolo[1,5-a][1,4]diazepine-2-carboxylate To a solution of dimethyl 1-(3-azidopropyl)-4-benzyloxy-1H-pyrazole-3,5-dicarboxylate (152 mg, 0.407 mmol) in THF (2 mL) were added triphenylphosphine (107 mg, 0.407 mmol) and water (37 µL, 2.036 mmol). The reaction was stirred at room temperature overnight, and the solvent was removed in vacuo. The residue was dissolved in toluene and heated to 110° C. overnight. Purification by reverse phase chromatography on a C-18 column using a gradient elution of 95-5% $H_2O$ (0.1% TFA)/$CH_3CN$ (0.1% TFA) and collection and concentration of the appropriate fractions afforded the title product. $^1$H NMR (400 MHz, $CDCl_3$) δ 7.44-7.41 (m, 2H), 7.34-7.28 (m, 3H), 6.70 (br s, 1H), 5.29 (s, 2H), 4.46-4.42 (t, 2H), 3.96 (s, 3H), 3.06-3.00 (m, 2H), 2.20-2.13 (m, 2H); ES MS (M+1)=316.

Step 4: 3-Benzyloxy-4-oxo-5,6,7,8-tetrahydro-4H-pyrazolo[1,5-a][1,4]diazepine-2-carboxylic acid To a solution of methyl 3-benzyloxy-4-oxo-5,6,7,8-tetrahydro-4H-pyrazolo[1,5-a][1,4]diazepine-2-carboxylate (50 mg, 0.159 mmol) in MeOH (2 mL) was added aqueous 1M NaOH (159 µL, 0.159 mmol). The reaction was stirred at room temperature for 4 hours, treated with additional aqueous 1N NaOH (159 µL, 0.159 mmol), and stirred at room temperature overnight. Aqueous 1N HCl (318 µL, 0.318 mmol) was added to the solution, and the solvents were removed in vacuo to afford the title product. $^1$H NMR (400 MHz, $CD_3OD$) δ 7.39-7.36 (m, 2H), 7.32-7.28 (m, 3H), 5.24 (s, 3H), 4.38-4.34 (t, 2H), 2.90-2.86 (t, 2H), 2.13-2.06 (dt, 2H); ES MS (M+1)=302.

Step 5: 3-Benzyloxy-N-(4-fluorobenzyl)-4-oxo-5,6,7,8-tetrahydro-4H-pyrazolo[1,5-a]91,4]diazepine-2-carboxamide The title compound was prepared from 3-benzyloxy-4-oxo-5,6,7,8-tetrahydro-4H-pyrazolo[1,5-a][1,4]diazepine-2-carboxylic acid using a procedure similar to that found in Example 13, Step 3, except that 4-fluorobenzylamine was used in place of 4-fluoro-N-methylbenzylamine and the reaction time totaled 10 minutes. Purification by reverse phase chromatography was not necessary. $^1$H NMR (400 MHz, $CDCl_3$) δ 7.26-7.22 (m, 7H), 7.01-6.96 (m, 2H), 6.15 (br s, 1H), 5.30 (s, 2H), 4.57-4.55 (d, 2H), 4.46-4.43 (t, 2H), 3.16-3.11 (m, 2H), 2.20-2.13 (dt, 2H); ES MS (M+1)=409.

Step 6: N-(4-Fluorobenzyl)-3-hydroxy-4-oxo-5,6,7,8-tetrahydro-4H-pyrazolo[1,5-a][1,4]diazepine-2-carboxamide The title compound was prepared from 3-benzyloxy-N-(4-fluorobenzyl)-4-oxo-5,6,7,8-tetrahydro-4H-pyrazolo[1,5-a]91,4]diazepine-2-carboxamide using a hydrogenation procedure similar to that found in Example 1, Step 5, except that the mixture was treated with acetic acid (3 drops) and the reaction time totaled 2 hours. Purification by reverse phase chromatography on a C-18 column using a gradient elution of 95-5% $H_2O$ (0.1% TFA)/$CH_3CN$ (0.1% TFA) and collection and concentration of the appropriate fractions afforded the title product. $^1$H NMR (400 MHz, $CD_3OD$) δ 7.40-7.36 (m, 2H), 7.08-7.03 (m, 2H), 4.56 (s, 2H), 4.51-4.47 (m, 2H), 3.51-3.48 (m, 2H), 2.32-2.26 (m, 2H); ES MS (M+1)=319.

EXAMPLE 30

Methyl 5-(4-Fluorobenzyl)-3-hydroxy-4-oxo-5,6,7,8-tetrahydro-4H-pyrazolo[1,5-a][1,4]diazepine-2-carboxylate

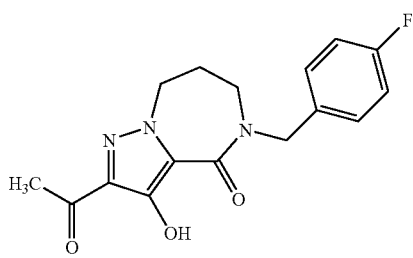

Step 1: Methyl 3-benzyloxy-5-(4-fluorobenzyl)-4-oxo-5,6,7,8-tetrahydro-4H-pyrazolo[1,5-a][1,4]diazepine-2-carboxylate The title compound was prepared from methyl 3-benzyloxy-4-oxo-5,6,7,8-tetrahydro-4H-pyrazolo[1,5-a][1,4]diazepine-2-carboxylate using a procedure similar to that found in Example 13, Step 1, except that 4-fluorobenzyl bromide was used in place of iodomethane and purification was not necessary. $^1$H NMR (400 MHz, $CDCl_3$) δ 7.42-7.32 (m, 5H), 7.08-7.00 (m, 4H), 5.33 (s, 2H), 4.64 (s, 2H), 4.26-4.22 (t, 2H), 3.95 (s, 3H), 1.88-1.81 (m, 2H), 1.62 (br s, 2H); ES MS (M+1)=424.

Step 2: Methyl 5-(4-Fluorobenzyl)-3-hydroxy-4-oxo-5,6,7,8-tetrahydro-4H-pyrazolo[1,5-a][1,4]diazepine-2-carboxylate The title compound was prepared from methyl 3-benzyloxy-5-(4-fluorobenzyl)-4-oxo-5,6,7,8-tetrahydro-4H-pyrazolo[1,5-a][1,4]diazepine-2-carboxylate using a hydrogenation procedure similar to that found in Example 1, Step 5, except that the mixture was treated with acetic acid (3 drops) and the reaction time totaled 2 hours. $^1$H NMR (400 MHz, $CD_3OD$) δ 7.42-7.38 (m, 2H), 7.10-7.06 (m, 2M), 4.75 (s, 2H), 4.40-4.36 (t, 2H), 3.89 (s, 3H), 3.56-3.53 (m, 2H), 2.22-2.16 (m, 2H); ES MS (M+1)=334.

EXAMPLE 31

N-(4-fluorobenzyl)-3-hydroxy-5-methyl-4-oxo-7-pyridin-3-yl-4,5,6,7-tetrahydropyrazolo[1,5-a]pyrazine-2-carboxamide

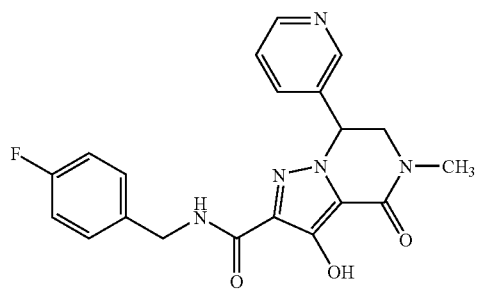

Step 1: Methyl 4-benzyloxy-3-carboxy-1H-pyrazole-5-carboxylate

Dimethyl 4-benzyloxy-1H-pyrazole-3,5-dicarboxylate (25 g, 86 mmol) was dissolved in N,N-dimethylhydrazine (75 mL) and the stirred mixture heated to reflux under nitrogen atmosphere for 30 hours. The solvent was removed in vacuo to give a white solid. The residue was dissolved in water (200 mL), 1N HCl (75 mL), and ethyl acetate (100 mL). The mixture was stirred and warmed to 35° C. until all the solids had dissolved. The layers were then separated and the aqueous layer was extracted with more ethyl acetate (3×100 mL). The combined organic extracts were dried over $Na_2SO_4$, filtered, and concentrated under reduced pressure to give the product as a white solid. $^1$H NMR (400 MHz, $d_6$-DMSO) δ 13.2 (br s, 1H), 7.3-7.45 (m, 5H), 5.09 (s, 2H), 3.81 (s, 3H); ES MS (M+1)=277.

Step 2: N-Methyl-N-[2-hydroxy-2-(pyridin-3-yl)ethyl]-4-benzyloxy-3-methoxycarbonyl-1H-pyrazole-5-carboxamide To a solution of methyl 4-benzyloxy-3-carboxy-1H-pyrazole-5-carboxylate (2.0 g, 7.24 mmol) in DMF (30 mL) were added HOBT (1.17 g, 8.69 mmol), 1-(3-pyridyl)-2-methylaminoethanol (1.21 g, 7.96 mmol; prepared by the methods of Tsushima, S., et al., EP 278621 and Cudahy, M. M., et al., WO 2003059911), triethylamine (0.88 g, 8.69 mmol), and EDC (1.67 g, 8.69 mmol). The reaction mixture was stirred at ambient temperature for 18 hours. The DMF was removed in vacuo and the residue was purified by prep HPLC (Waters prep LC 4000 System using a Waters Nova Pak column (3 100×40 mm I.D. cartridges, C18, 6 μM pore size) eluting with 95-5% water (0.10% TFA)/acetonitrile (0.10% TFA) at 60 mL/minute). Appropriate fractions were combined and the solvent was removed under reduced pressure to give a yellow solid. The free base of the product was obtained by partitioning between aqueous $NaHCO_3$ and ethyl acetate. The combined organic extracts were dried over $Na_2SO_4$, filtered and concentrated in vacuo to give a gum. ES MS (M+1)=277.

Step 3: Methyl 3-benzyloxy-5-methyl-4-oxo-7-pyridin-3-yl-4,5,6,7-tetrahydropyrazolo[1,5-a]pyrazine-2-carboxylate To a solution of N-methyl-N-[2-hydroxy-2-(pyridin-3-yl)ethyl]-4-benzyloxy-3-methoxycarbonyl-1H-pyrazole-5-carboxamide (1.0 g, 2.44 mmol) and triphenylphosphine (2.24 g, 8.53 mmol) in THF (30 mL) was added diethyl azodicarboxylate (1.55 mL, 8.53 mmol) dropwise over a period of 5 minutes. The mixture was stirred for 2 hours. The solvent was removed in vacuo and the residue was purified by preparative HPLC (Waters prep LC 4000 System using a Waters Nova Pak column (3 100×40 mm I.D. cartridges, C18, 6 μM pore size) eluting with 95-5% water (0.10% TFA)/acetonitrile (0.10% TFA) at 60 mL/minute). Appropriate fractions were combined and the solvents were removed under reduced pressure to give a gum. $^1$H NMR (400 MHz, $d_6$-DMSO) δ 8.66 (s, 1H), 8.50 (s, 1H), 7.5-7.6 (m, 4H), 7.3-7.4 (m, 3H), 5.96 (t, J=4.4 Hz, 1H), 5.28 (AB quartet, J=10.9 Hz, 2H), 4.20 (dd, J=13, 4.2 Hz, 1H), 4.00 (dd, J=13, 4.4 Hz, 1H), 3.76 (s, 3H), 2.97 (s, 3H); ES MS (M+1)=393.

Step 4: Methyl 3-hydroxy-5-methyl-4-oxo-7-pyridin-3-yl-4,5,6,7-tetrahydropyrazolo[1,5-a]pyrazine-2-carboxylate To a solution of methyl 3-benzyloxy-5-methyl-4-oxo-7-pyridin-3-yl-4,5,6,7-tetrahydropyrazolo[1,5-a]pyrazine-2-carboxylate (0.48 g, 1.2 mmol) in MeOH (25 mL) was added 10% palladium on carbon (60 mg). The mixture was stirred under an atmosphere of hydrogen gas for 2 hours. The reaction was then filtered through celite, and the filtrate solvent was removed in vacuo to give the product as a gum. ES MS (M+1)=303.

Step 5: N-(4-fluorobenzyl)-3-hydroxy-5-methyl-4-oxo-7-pyridin-3-yl-4,5,6,7-tetrahydropyrazolo[1,5-a]pyrazine-2-carboxamide Methyl 3-hydroxy-5-methyl-4-oxo-7-pyridin-3-yl-4,5,6,7-tetrahydropyrazolo[1,5-a]pyrazine-2-carboxylate (40 mg, 0.13 mmol) and 4-fluorobenzylamine (130 mg, 1.06 mmol) were combined in MeOH (0.5 mL) and the mixture was heated to reflux, allowing the solvent to slowly evaporate over 18 hours. The residue was purified by preparative HPLC (Waters Nova Pak column (100×40 mm I.D. cartridge, C18, 6 μM pore size) eluting with 95-5% water (0.1% TFA)/acetonitrile (0.1% TFA) at 35 mL/minute.). The appropriate fractions were combined and the solvent was removed to give the title compound as a gum. $^1$H NMR (400 MHz, $d_6$-DMSO) δ 8.77 (t, J=6 Hz, 1H), 8.67 (s, 1H), 8.53 (s, 1H), 7.6-7.7 (m, 2H), 7.33 (dd, J=5.7, 8.6 Hz, 2H), 7.13 (t, J=9.0 Hz, 2H), 5.90 (t, J=4.6 Hz, 1H), 4.39 (ABX, J=15, 6.1 Hz, 2H), 4.19 (dd, J=13, 4.6 Hz, 1H), 3.91 (dd, J=13, 4.5 Hz, 1H), 2.91 (s, 3H); ES MS (M+1)=396.

EXAMPLE 32

N-(4-fluorobenzyl)-3-hydroxy-5-methyl-4-oxo-4,5-dihydropyrazolo[1,5-a]quinoxaline-2-carboxamide

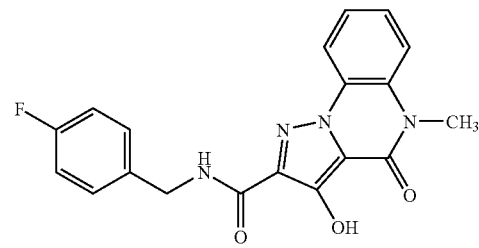

Step 1: Dimethyl 4-benzyloxy-1-(2-nitrophenyl)-1H-pyrazole-3,5-dicarboxylate A solution of dimethyl 4-benzyloxy-1H-pyrazole-3,5-dicarboxylate (2.5 g, 8.63 mmol) and 2-fluoronitrobenzene (1.45 g, 10.3 mmol) in anhydrous DMF (15 mL) was treated with $Cs_2CO_3$ (3.6 g, 11 mmol) and stirred at 50° C. for 6 hours. The solvent was removed in vacuo, the residue was suspended EtOAc, and the insoluble salts were removed by filtration. The filtrate solvent was removed under reduced pressure and the residue was purified by flash column chromatography on silica gel using a gradient elution of 1:4 to 1:2 to 1:1 EtOAc:hexanes. Collection and concentration of the appropriate fractions yielded the product as an oil. $^1$H NMR (400 MHz, CDCl₃) δ 8.21 (d, J=8.0 Hz, 1H), 7.75 (t, J=7.6 Hz, 1H), 7.68 (t, J=7.9 Hz, 1H), 7.48-7.53 (m, 3H), 7.36-7.42 (m, 3H), 5.24 (s, 2H), 3.96 (s, 3H), 3.69 (s, 3H); ES MS (M+1)=412.

Step 2: Methyl 3-hydroxy-4-oxo-4,5-dihydropyrazolo[1,5-a]quinoxaline-2-carboxylate To a solution of dimethyl 4-benzyloxy-1-(2-nitrophenyl)-1H-pyrazole-3,5-dicarboxylate (2.0 g, 4.85 mmol) in MeOH (100 mL) was added palladium on carbon (200 mg). The mixture was then stirred and purged with hydrogen gas. The mixture was stirred at ambient temperature under 1 atmosphere of hydrogen gas for 72 hours. The mixture was filtered through celite and the filter cake was washed with MeOH. The filtrate solvent was removed under reduced pressure. Trituration of the residue in a small volume of MeOH gave the product as a white solid. ¹H NMR (400 MHz, d₆-DMSO) δ 11.65 (s, 1H), 9.74 (s, 1H), 8.07 (d, J=8.2 Hz, 1H), 7.41 (t, J=7.9 Hz, 1H), 7.25-7.34 (m, 2H), 3.88 (s, 3H); ES MS (M+1)=260.

Step 3: Methyl 3-methoxy-5-methyl-4-oxo-4,5-dihydropyrazolo[1,5-a]quinoxaline-2-carboxylate To a solution of methyl 3-hydroxy-4-oxo-4,5-dihydropyrazolo[1,5-a]quinoxaline-2-carboxylate (525 mg, 2.02 mmol) in DMF (5 mL) under inert atmosphere was added iodomethane (1.0 g, 7.0 mmol) and cesium carbonate (1.6 g, 5.0 mmol). The mixture was stirred at ambient temperature for 18 hours. The solvent was removed under reduced pressure and the residue was suspended in EtOAc. The solids were removed by filtration. The filtrate solvent was removed under reduced pressure to give the product as an oil. ES MS (M+1)=288.

Step 4: 3-Methoxy-5-methyl-4-oxo-4,5-dihydropyrazolo[1,5-a]quinoxaline-2-carboxylic acid To a solution of methyl 3-methoxy-5-methyl-4-oxo-4,5-dihydropyrazolo[1,5-a]quinoxaline-2-carboxylate (220 mg, 0.7 mmol) in MeOH (5 mL) was added aqueous NaOH (0.91 mL of a 1.0 N solution, 0.91 mmol). The mixture was stirred at ambient temperature for 18 hours. Aqueous HCl (0.16 mL of a 6.0 N solution, 0.96 mmol) was added to the mixture and the solvents were removed under reduced pressure. The residue was triturated in 1:1 MeOH:water and filtered to give the product as a white solid. ¹H NMR (400 MHz, d₆-DMSO) δ 13.31 (s, 1H), 8.20 (d, J=8.1 Hz, 1H), 7.61 (d, J=7.9 Hz, 1H), 7.55 (t, f=8.0 Hz, 1H), 7.41 (t, J=8.0 Hz, 1H), 7.55 (t, J=8.0 Hz, 1H), 3.99 (s, 3H), 3.60 (s, 3H); ES MS (M+1)=274.

Step 5: N-(4-fluorobenzyl)-3-methoxy-5-methyl-4-oxo-4,5-dihydropyrazolo[1,5-a]quinoxaline-2-carboxamide To a solution of 3-methoxy-5-methyl-4-oxo-4,5-dihydropyrazolo[1,5-a]quinoxaline-2-carboxylic acid (75 mg, 0.27 mmol) in DMF were added HOBT (46 mg, 0.3 mmol), EDC (76 mg, 0.4 mmol), DIEA (0.05 mL, 0.29 mmol), and 4-fluorobenzylamine (50 mg, 0.4 mmol). The reaction mixture was stirred at room temperature for 24 hours. The solvent was removed under reduced pressure and the residue was partitioned between EtOAc and aqueous sodium bicarbonate. The EtOAc layer was dried (MgSO₄), filtered and the solvent was removed under reduced pressure. The residue was triturated in MeOH to give the product as a white solid. ¹H NMR (400 MHz, d₆-DMSO) δ 8.91 (t, J=5.9 Hz, 1H), 8.26 (d, J=8.0 Hz, 1H), 7.62 (d, J=7.8 Hz, 1H), 7.54 (t, J=7.9 Hz, 1H), 7.39-7.44 (m, 3H), 7.17 (t, J=8.9 Hz, 2H), 4.49 (d, J=6.1 Hz, 2H), 4.02 (s, 3H), 3.61 (s, 3H); ES MS (M+1)=381.

Step 6: N-(4-fluorobenzyl)-3-hydroxy-5-methyl-4-oxo-4,5-dihydropyrazolo[1,5-a]quinoxaline-2-carboxamide To a solution of N-(4-fluorobenzyl)-3-methoxy-5-methyl-4-oxo-4,5-dihydropyrazolo[1,5-a]quinoxaline-2-carboxamide (85 mg, 0.22 mmol) in AcOH (1 mL) was added 30% HBr in AcOH (2 mL). The mixture was stirred and warmed to 50° C. for 8 hours. The solvent was removed under reduced pressure. The residue was triturated in AcOH to give the title compound as a white solid. ¹H NMR (400 MHz, d₆-DMSO) δ 9.82 (br s, 1H), 9.06 (t, J=6.0 Hz, 1H), 8.20 (d, J=8.0 Hz, 1H), 7.58 (d, J=7.8 Hz, 1H), 7.51 (t, J=7.8 Hz, 1H), 7.38-7.43 (m, 3H), 7.17 (t, J=9.0 Hz, 2H), 4.50 (d, J=6.2 Hz, 2H), 4.02 (s, 3H), 3.57 (s, 3H); ES MS (M+1)=367.

EXAMPLE 33

(7S)—N-{4-Fluoro-2-[(methylamino)carbonyl]benzyl}-3-hydroxy-5-methyl-4-oxo-7-phenyl-4,5,6,7-tetrahydropyrazolo[1,5-a]pyrazine-2-carboxamide

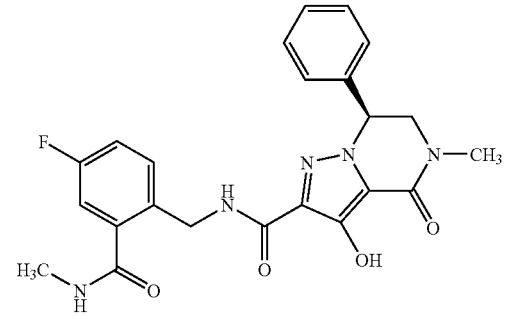

Step 1: Methyl 4-(benzyloxy)-5-{[[(2R)-2-hydroxy-2-phenylethyl](methyl)amino]carbonyl}-1H-pyrazole-3-carboxylate To a solution of methyl 4-benzyloxy-3-carboxy-1H-pyrazole-5-carboxylate (1.5 g, 5.43 mmol; prepared as in Example 31, Step 1) in DMF (20 mL) were added HOAT (1.11 g, 8.15 mmol), (1R)-2-(methylamino)-1-phenylethanol (1.23 g, 8.15 mmol; prepared as described in Gurjar, M. K., et al., *Org. Process Res. Dev.* 1998, 2, 422.), triethylamine (0.82 g, 8.15 mmol), and EDC (1.56 g, 8.15 mmol). The reaction mixture was stirred at ambient temperature for 3 hours. The DMF was removed in vacuo and the residue was partitioned between saturated aqueous NH₄Cl and EtOAc. The layers were separated and the aqueous was extracted twice more with EtOAc. The combined organic extracts were dried over Na₂SO₄ and concentrated in vacuo to afford the title product. ES MS (M+1)=410.

Step 2: Methyl (7S)-3-(benzyloxy)-5-methyl-4-oxo-7-phenyl-4,5,6,7-tetrahydropyrazolo[1,5-a]pyrazine-2-carboxylate The title compound was prepared from methyl 4-(benzyloxy)-5-{[[(2R)-2-hydroxy-2-phenylethyl](methyl)amino]carbonyl}-1H-pyrazole-3-carboxylate using a procedure similar to that described in Example 31, Step 3. $^1$H NMR (400 MHz, d$_6$-DMSO) ☐ 7.49 (m, 2H), 7.3-7.4 (m, 6H), 7.02 (m, 2H), 5.81 (t, J=4.4 Hz, 1H), 5.27 (AB quartet, J=10.9 Hz, 2H), 4.19 (dd, J=13.5, 4.7 Hz, 1M), 3.88 (dd, J=13.5, 4.5 Hz, 1H), 3.77 (s, 3H), 2.93 (s, 3H); ES MS (M+1)=392.

Step 3: Methyl (7S)-3-hydroxy-5-methyl-4-oxo-7-phenyl-4,5,6,7-tetrahydropyrazolo[1,5-a]pyrazine-2-carboxylate The title compound was prepared from methyl (7S)-3-(benzyloxy)-5-methyl-4-oxo-7-phenyl-4,5,6,7-tetrahydropyrazolo[1,5-a]pyrazine-2-carboxylate using a hydrogenation procedure similar to that described in Example 31, Step 4. $^1$H NMR (400 MHz, d$_6$-DMSO) δ 9.23 (br s, 1H), 7.37 (m, 3H), 7.10 (m, 2H), 5.75 (t, J=4.5 Hz, 1H), 4.12 (m, 1H), 3.86 (m, 1H), 3.76 (s, 3H), 2.90 (s, 3H); ES MS (M+1)=302.

Step 4: (7S)-3-Hydroxy-5-methyl-4-oxo-7-phenyl-4,5,6,7-tetrahydropyrazolo[1,5-a]pyrazine-2-carboxylic acid To a solution of ethyl (7S)-3-hydroxy-5-methyl-4-oxo-7-phenyl-4,5,6,7-tetrahydropyrazolo[1,5-a]pyrazine-2-carboxylate (0.30 g, 1.00 mmol) in MeOH (10 mL) was added aqueous 1N NaOH (5.97 mL, 5.97 mmol). The reaction was stirred at 50° C. overnight and quenched by the addition of aqueous 3N HCl (2.00 mL, 2.00 mmol). Purification by reverse phase chromatography on a C-18 column using a gradient elution of 95-5% H$_2$O (0.1% TFA)/CH$_3$CN (0.1% TFA) and collection and concentration of the appropriate fractions afforded the title product as a light pink solid. $^1$H NMR (400 MHz, d$_6$-DMSO) δ 8.90 (bs, 1H), 7.37 (m, 3H), 7.08 (m, 2H), 5.74 (t, J=4.6 Hz, 1H), 4.15 (dd, J=13.4, 4.6 Hz, 1H), 3.86 (dd, J=13.4, 4.7 Hz, 1H), 2.89 (s, 3H); ES MS (M+1)=288.

Step 5: Methyl 5-fluoro-2-[({[(7S)-3-hydroxy-5-methyl-4-oxo-7-phenyl-4,5,6,7-tetrahydropyrazolo[1,5-a]pyrazin-2-yl]carbonyl}amino)methyl]benzoate To a solution of (7S)-3-hydroxy-5-methyl-4-oxo-7-phenyl-4,5,6,7-tetrahydropyrazolo[1,5-a]pyrazine-2-carboxylic acid (246 mg, 0.856 mmol) in DMF (3 mL) were added HOAT (175 mg, 1.28 mmol), and EDC (246 mg, 1.28 mmol). The reaction mixture was stirred at ambient temperature 15 minutes then methyl 2-(aminomethyl)-5-fluorobenzoate hydrochloride (226 mg, 1.03 mmol) and triethylamine (0.13 g, 1.28 mmol) were added. The reaction was stirred at ambient temperature overnight. The solvent was removed in vacuo, and the resulting residue was purified by reverse phase chromatography on a C-18 column using a gradient elution of 95-5% H$_2$O (0.1% TFA)/CH$_3$CN (0.1% TFA). Collection and concentration of the appropriate fractions afforded the product as a light pink solid. $^1$H NMR (400 MHz, d$_6$-DMSO) δ 9.60 (bs, 1H), 8.60 (t, J=6.2 Hz, 1H), 7.61 (dd, J=9.5, 2.3 Hz, 1H), 7.45 (m, 2H), 7.36 (m, 3H), 7.04 (d, J=7.1 Hz, 2H), 5.75 (t, J=4.0 Hz, 1H), 4.68 (ABX, J=15.8, 6.2 Hz, 2H), 4.18 (dd, J=13.4, 4.5 Hz, 1H), 3.86 (s, 3H), 3.81 (dd, J=13.4, 4.0 Hz, 1H), 2.88 (s, 3H); ES MS (M+1)-453.

Step 6: 5-Fluoro-2-[({[(7S)-3-hydroxy-5-methyl-4-oxo-7-phenyl-4,5,6,7-tetrahydropyrazolo[1,5-a]pyrazin-2-yl]carbonyl}amino)methyl]benzoic acid To a solution of methyl 5-fluoro-2-[({[(7S)-3-hydroxy-5-methyl-4-oxo-7-phenyl-4,5,6,7-tetrahydropyrazolo[1,5-a]pyrazin-2-yl]carbonyl}amino)methyl]benzoate (48 mg, 0.106 mmol) in MeOH (1 mL) was added aqueous 1N NaOH (233 µL, 0.233 mmol). The reaction was stirred at 45° C. overnight. Purification by reverse phase chromatography on a C-18 column using a gradient elution of 95-5% H$_2$O (0.1% TFA)/CH$_3$CN (0.1% TFA) and collection and concentration of the appropriate fractions afforded the title product. ES MS (M+1)=439.

Step 7: (7S)—N-{4-Fluoro-2-[(methylamino)carbonyl]benzyl}-3-hydroxy-5-methyl-4-oxo-7-phenyl-4,5,6,7-tetrahydropyrazolo[1,5-a]pyrazine-2-carboxamide To a solution of 5-fluoro-2-[({[(7S)-3-hydroxy-5-methyl-4-oxo-7-phenyl-4,5,6,7-tetrahydropyrazolo[1,5-a]pyrazin-2-yl]carbonyl}amino)methyl]benzoic acid (47 mg, 0.106 mmol) in DMF (1 mL) were added HOAT (44 mg, 0.322 mmol), and EDC (62 mg, 0.322 mmol). The reaction mixture was stirred at ambient temperature 15 minutes then 2M methylamine in THF (214 µL, 0.429 mmol) and triethylamine (45 µL, 0.322 mmol) were added. The reaction was stirred at ambient temperature for 5 hours. The crude reaction was purified by reverse phase chromatography on a C-18 column using a gradient elution of 95-5% H$_2$O (0.1% TFA)/CH$_3$CN (0.1% TFA). Collection and concentration of the appropriate fractions afforded the product as a light pink solid. $^1$H NMR (400 MHz, d$_6$-DMSO) δ 8.55 (t, J=6.2 Hz, 1H), 8.48 (m, 1H), 7.3-7.4 (m, 4H), 7.25 (m, 2H), 7.03 (m, 2H), 5.75 (t, J=4.0 Hz, 1H), 4.68 (ABX, J=15.2, 6.4 Hz, 2H), 4.18 (dd, J=13.4, 4.6 Hz, 1H), 3.79 (dd, J=13.4, 3.8 Hz, 1H), 2.87 (s, 3H), 2.75 (d, J=4.6 Hz, 3H); HRMS (FT-ICR) $C_{23}H_{22}FN_5O_4$+H=452.1735; calculated 452.1729.

EXAMPLES 34-42

The compounds in the following table were prepared in accordance with the procedure set forth in Example 33.

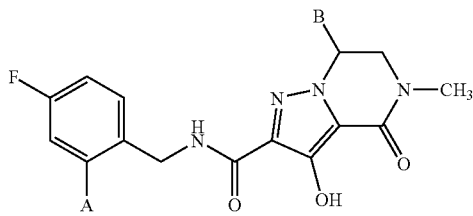

| Ex. | Name | A | B | HRMS (FT-ICR) |
|---|---|---|---|---|
| 34 | (7R)-N-{4-Fluoro-2-[(methylamino)carbonyl]benzyl}-3-hydroxy-5-methyl-4-oxo-7-phenyl-4,5,6,7-tetrahydropyrazolo[1,5-a]pyrazine-2-carboxamide | —C(O)N(H)Me | phenyl | $C_{23}H_{22}FN_5O_4 + H = 452.1740$; calculated 452.1729 |
| 35 | (7R)-N-{2-[(Cyclopropylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | *—C(O)NH-cyclopropyl | phenyl | $C_{25}H_{24}FN_5O_4 + H = 478.1891$; calculated 478.1885 |
| 36 | (7S)-N-{2-[(Cyclopropylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | *—C(O)NH-cyclopropyl | phenyl | $C_{25}H_{24}FN_5O_4 + H = 478.1892$; calculated 478.1885 |
| 37 | (7R)-N-{2-[(Dimethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | —C(O)NMe₂ | phenyl | $C_{24}H_{24}FN_5O_4 + H = 466.1894$; calculated 466.1885 |
| 38 | (7S)-N-{2-[(Dimethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | —C(O)NMe₂ | phenyl | $C_{24}H_{24}FN_5O_4 + H = 466.1894$; calculated 466.1885 |
| 39 | (7R)-N-{2-[(Ethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | —C(O)N(H)Et | phenyl | $C_{24}H_{24}FN_5O_4 + H = 466.1891$; calculated 466.1885 |
| 40 | (7S)-N-{2-[(Ethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide | —C(O)N(H)Et | phenyl | $C_{24}H_{24}FN_5O_4 + H = 466.1890$; calculated 466.1885 |

-continued

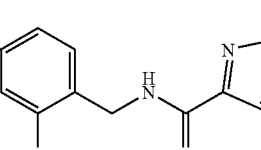

| Ex. | Name | A | B | HRMS (FT-ICR) |
|---|---|---|---|---|
| 41 | (7R)-N-[2-(Aminocarbonyl)-4-fluorobenzyl]-3-hydroxy-5-methyl-4-oxo-7-phenyl-4,5,6,7-tetrahydropyrazolo[1,5-a]pyrazine-2-carboxamide | —C(O)NH$_2$ | 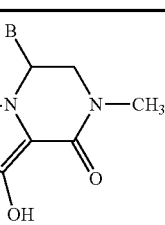 | $C_{22}H_{20}FN_5O_4$ + H = 438.1580; calculated 438.1572 |
| 42 | (7S)-N-[2-(Aminocarbonyl)-4-fluorobenzyl]-3-hydroxy-5-methyl-4-oxo-7-phenyl-4,5,6,7-tetrahydropyrazolo[1,5-a]pyrazine-2-carboxamide | —C(O)NH$_2$ | 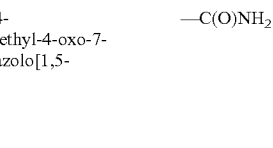 | $C_{22}H_{20}FN_5O_4$ + H = 438.1575; calculated 438.1572 |

EXAMPLE 43

7-(3-Bromophenyl)-N-(4-fluorobenzyl)-3-hydroxy-5-methyl-4-oxo-4,5,6,7-tetrahydropyrazolo[1,5-a]pyrazine-2-carboxamide

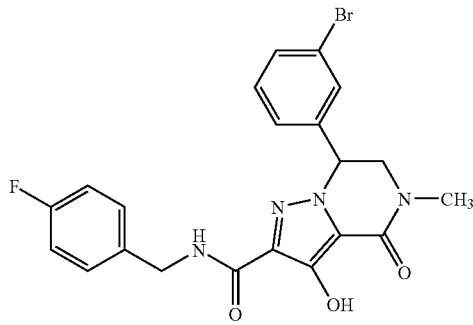

Step 1: Methyl 4-(benzyloxy)-5-{[[2-(3-bromophenyl)-2-hydroxyethyl](methyl)amino]carbonyl}-1H-pyrazole-3-carboxylate The title compound was prepared from methyl 4-benzyloxy-3-carboxy-1H-pyrazole-5-carboxylate (prepared as in Example 31, Step 1) using a procedure similar to that described in Example 31, Step 2, except that 1-(3-bromophenyl)-2-(methylamino)ethanol (prepared as described in Tsushima, S., et al., EP 278621 and Cudahy, M. M., et al., WO 2003059911) was used in place of (1R)-2-(methylamino)-1-phenylethanol. ES MS (M+2)=490.

Step 2: Methyl 3-(benzyloxy)-7-(3-bromophenyl)-5-methyl-4-oxo-4,5,6,7-tetrahydropyrazolo[1,5-a]pyrazine-2-carboxylate The title compound was prepared from methyl 4-(benzyloxy)-5-{[[2-(3-bromophenyl)-2-hydroxyethyl](methyl)amino]carbonyl}-1H-pyrazole-3-carboxylate using a procedure similar to that described in Example 31, Step 3. $^1$H NMR (400 MHz, d$_6$-DMSO) δ 7.58 (m, 1H), 7.49 (m, 2H), 7.3-7.4 (m, 5H), 6.94 (d, J=7.8 Hz, 1H), 5.85 (t, J=4.7 Hz, 1H), 5.27 (AB quartet, J=11.0 Hz, 2H), 4.17 (dd, J=13.7, 4.6 Hz, 1H), 3.93 (dd, J=13.5, 4.9 Hz, 1H), 3.77 (s, 3H), 2.95 (s, 3H); ES MS (M+2)=472.

Step 3: 3-(Benzyloxy)-7-(3-bromophenyl)-5-methyl-4-oxo-4,5,6,7-tetrahydropyrazolo[1,5-a]pyrazine-2-carboxylic acid The title compound was prepared from methyl 3-(benzyloxy)-7-(3-bromophenyl)-5-methyl-4-oxo-4,5,6,7-tetrahydropyrazolo[1,5-a]pyrazine-2-carboxylate using a procedure similar to that described in Example 33, Step 4. Purification was achieved by removing the solvent in vacuo and partitioning the residue between saturated aqueous NH$_4$Cl and EtOAc. The layers were separated and the aqueous was extracted twice more with EtOAc. The combined organic extracts were dried over Na$_2$SO$_4$ and concentrated in vacuo to afford the title product as a white solid. $^1$H NMR (400 MHz, d$_6$-DMSO) δ 13.0 (bs, 1H), 7.58 (d, J=8.1 Hz, 1H), 7.52 (d, J=7.3 Hz, 2H), 7.3-7.4 (m, 5H), 6.93 (d, J=7.9 Hz, 1H), 5.83 (t, J=4.4 Hz, 1H), 5.27 (AB quartet, J=11.0 Hz, 2H), 4.17 (dd, J=13.7, 4.6 Hz, 1H), 3.92 (dd, J=13.6, 4.4 Hz, 1H), 2.94 (s, 3H); ES MS (M+2)=458.

Step 4: 3-(Benzyloxy)-7-(3-bromophenyl)-N-(4-fluorobenzyl)-5-methyl-4-oxo-4,5,6,7-tetrahydropyrazolo[1,5-a]pyrazine-2-carboxamide The title compound was prepared from 3-(benzyloxy)-7-(3-bromophenyl)-N-(4-fluorobenzyl)-5-methyl-4-oxo-4,5,6,7-tetrahydropyrazolo[1,5-a]pyrazine-2-carboxamide using a procedure similar to that described in Example 33, Step 5, except that 4-fluorobenzylamine was used in place of methyl 2-(aminomethyl)-5-fluorobenzoate hydrochloride and the total reaction time was 3 hours. Purification was achieved by removing the solvent in vacuo and partitioning the residue between saturated aqueous NH₄Cl and EtOAc. The layers were separated and the aqueous was extracted twice more with EtOAc. The combined organic extracts were dried over Na₂SO₄ and concentrated in vacuo to afford the title product as a yellow oil. ES MS (M+1)=563.

Step 5: 7-(3-Bromophenyl)-N-(4-fluorobenzyl)-3-hydroxy-5-methyl-4-oxo-4,5,6,7-tetrahydropyrazolo[1,5-a]pyrazine-2-carboxamide A solution of 3-(benzyloxy)-7-(3-bromophenyl)-5-methyl-4-oxo-4,5,6,7-tetrahydropyrazolo[1,5-a]pyrazine-2-carboxylic acid (50 mg, 0.089 mmol) and 30% HBr in AcOH in AcOH (0.857 mL) was stirred at ambient temperature overnight. The solvent was removed in vacuo, and the resulting residue was purified by reverse phase chromatography on a C-18 column using a gradient elution of 95-5% H₂O (0.1% TFA)/CH₃CN (0.1% TFA). Collection and concentration of the appropriate fractions afforded the product. ¹H NMR (400 MHz, d₆-DMSO) δ 9.56 (s, 1H), 8.78 (t, J=6.1 Hz, 1H), 7.54 (d, J=7.7 Hz, 1H), 7.31-7.36 (m, 4H), 7.13 (t, J=8.7 Hz, 2H), 6.97 (d, J=7.6 Hz, 1H), 5.77 (t, J=4.3 Hz, 1H), 4.39 (ABX, J=15.0, 6.4 Hz, 2H), 4.16 (dd, J=13.5, 4.5 Hz, 1H), 3.84 (dd, J=13.3, 3.9 Hz, 1H), 3.32 (s, 3H); HRMS (FT-ICR) C₂₁H₁₈BrFN₄O₃=473.0637; calculated 473.0619.

EXAMPLE 44

7-(3-Cyanophenyl)-N-(4-fluorobenzyl)-3-hydroxy-5-methyl-4-oxo-4,5,6,7-tetrahydropyrazolo[5,5-a]pyrazine-2-carboxamide

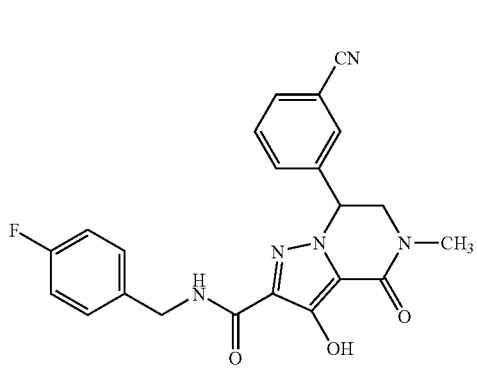

Step 1: 3-(Benzyloxy)-7-(3-cyanophenyl)-N-(4-fluorobenzyl)-5-methyl-4-oxo-4,5,6,7-tetrahydropyrazolo[1,5-a]pyrazine-2-carboxamide To solution of 3-(benzyloxy)-7-(3-bromophenyl)-N-(4-fluorobenzyl)-5-methyl-4-oxo-4,5,6,7-tetrahydropyrazolo[1,5-a]pyrazine-2-carboxamide (0.40 g, 0.71 mmol; from Example 43, Step 4) in dry degassed DMF (2.0 mL) in a sealable pressure tube were added zinc cyanide (50 mg, 0.426 mmol) and tetrakis(triphenylphosphine)palladium(0) (164 mg, 0.142 mmol). The reaction tube was capped and the reaction mixture was stirred at 110° C. for 1.5 hours. The DMF was removed in vacuo and the residue was partitioned between saturated aqueous NH₄Cl and EtOAc. The layers were separated and the aqueous was extracted twice more with EtOAc. The combined organic extracts were dried over Na₂SO₄ and concentrated in vacuo. The resulting residue was purified by reverse phase chromatography on a C-18 column using a gradient elution of 95-5% H₂O (0.1% TFA)/CH₃CN (0.1% TFA). Collection and concentration of the appropriate fractions afforded the product as sticky gum. ES MS (M+1)=510.

Step 2: 7-(3-Cyanophenyl)-N-(4-fluorobenzyl)-3-hydroxy-5-methyl-4-oxo-4,5,6,7-tetrahydropyrazolo[1,5-a]pyrazine-2-carboxamide The title compound was prepared from 3-(benzyloxy)-7-(3-cyanophenyl)-N-(4-fluorobenzyl)-5-methyl-4-oxo-4,5,6,7-tetrahydropyrazolo[1,5-a]pyrazine-2-carboxamide in a procedure similar to that described in Example 43, Step 5. ¹H NMR (400 MHz, d₆-DMSO) δ 9.6 (bs, 1H), 8.78 (t, J=6.0 Hz, 1H), 7.84 (d, J=7.7 Hz, 1H), 7.70 (s, 1H), 7.59 (t, J=7.9 Hz, 1H), 7.33 (m, 2H), 7.25 (d, J=8.1 Hz, 1H), 7.13 (m, 2H), 5.84 (t, J=4.4 Hz, 1H), 4.39 (ABX, J=14.8, 6.2 Hz, 2H), 4.17 (dd, J=13.4, 4.6 Hz, 1H), 3.89 (dd, J=13.4, 4.6 Hz, 1H), 2.88 (s, 3H); HRMS (FT-ICR) C₂₂H₁₈FN₅O₃+H=420.1480; calculated 420.1466.

EXAMPLE 45

N-(4-Fluorobenzyl)-3-hydroxy-5-methyl-4-oxo-7-pyridin-4-yl-4,5,6,7-tetrahydropyrazolo[1,5-a]pyrazine-2-carboxamide

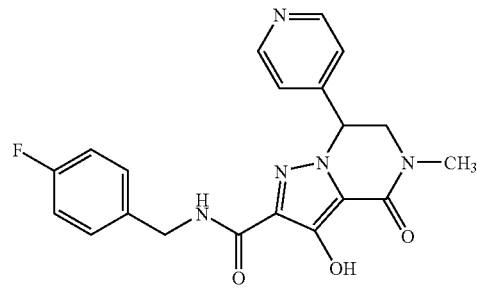

Step 1: N-(4-Fluorobenzyl)-3-hydroxy-5-methyl-4-oxo-7-pyridin-4-yl-4,5,6,7-tetrahydropyrazolo[1,5-a]pyrazine-2-carboxamide The title compound was prepared from methyl 4-benzyloxy-3-carboxy-1H-pyrazole-5-carboxylate (prepared in Example 31, Step 1) using a procedure similar to that described in Example 31, Steps 2-5, except that in Step 2,1-(4-pyridyl)-2-methylaminoethanol (prepared by the methods of Tsushima, S., et al., EP 278621 and Cudahy, M. M., et al., WO 2003059911) was used in place of 1-(3-pyridyl)-2-methylaminoethanol. ¹H NMR (400 MHz, d₆-DMSO) δ 8.83 (t, J=6.4 Hz, 1H), 8.67 (s, 2H), 7.34 (dd, J=8.1, 5.6 Hz, 2H), 7.20 (d, J=5.0 Hz, 2H), 7.14 (t, J=8.8 Hz, 2H), 5.92 (m, 1H), 4.39 (ABX, J=15, 6.4 Hz, 2H), 4.27 (dd, J=14, 4.6 Hz, 1H), 3.89 (dd, J=13.5, 3.3 Hz, 1H), 2.86 (s, 3H); ES MS (M+1)=396.

EXAMPLE 46

N-(3-Chloro-4-fluorobenzyl)-3-hydroxy-5-methyl-4-oxo-7-pyridin-4-yl-4,5,6,7-tetrahydropyrazolo[1,5-a]pyrazine-2-carboxamide

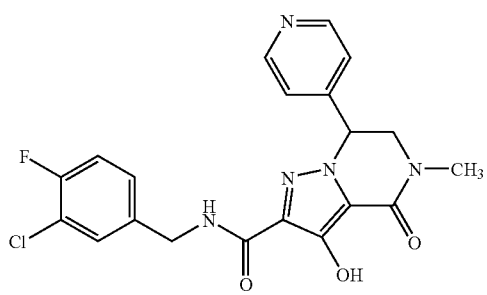

The title compound was prepared in accordance with the procedure set forth in Example 45. ES MS (M+1)=430

EXAMPLE 47

N-{4-Fluoro-2-[(methylamino)carbonyl]benzyl}-3-hydroxy-5-methyl-4-oxo-7-pyridin-2-yl-4,5,6,7-tetrahydropyrazolo[1,5-a]pyrazine-2-carboxamide

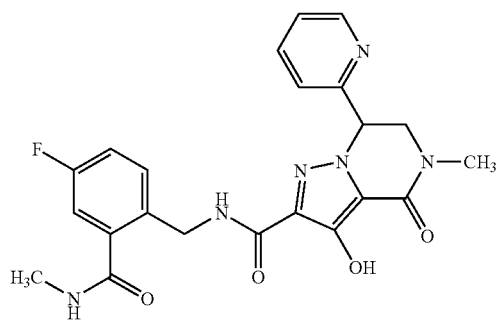

Step 1: Methyl 4-(benzyloxy)-5-{[(2-hydroxy-2-pyridin-2-ylethyl)(methyl)amino]carbonyl}-1H-pyrazole-3-carboxylate The title compound was prepared from methyl 4-benzyloxy-3-carboxy-1H-pyrazole-5-carboxylate (prepared as in Example 31, Step 1) using a procedure similar to that described in Example 31, Step 2, except that 1-(2-pyridyl)-2-methylaminoethanol (prepared by the methods of Tsushima, S., et al., EP 278621 and Cudahy, M. M., et al., WO 2003059911) was used in place of 1-(3-pyridyl)-2-methylaminoethanol. ES MS (M+1)=410.

Step 2: 3-(Benzyloxy)-N-{4-fluoro-2-[(methylamino)carbonyl]benzyl}-5-methyl-4-oxo-7-pyridin-2-yl-4,5,6,7-tetrahydropyrazolo[1,5-a]pyrazine-2-carboxamide The title compound was prepared from methyl 4-(benzyloxy)-5-{[(2-hydroxy-2-pyridin-2-ylethyl)(methyl)amino]carbonyl}-1H-pyrazole-3-carboxylate using a procedure similar to that described in Example 43, Steps 2-4, except that 4-fluoro-2-[(methylamino)carbonyl]benzylamine hydrochloride was used in place of 4-fluorobenzylamine. Purification was achieved by removing the solvent in vacuo, and purifying the resulting residue by reverse phase chromatography on a C-18 column using a gradient elution of 95-5% $H_2O$ (0.1% TFA)/$CH_3CN$ (0.1% TFA). Collection and concentration of the appropriate fractions afforded the product. ES MS (M+1)=543.

Step 3: N-{4-Fluoro-2-[(methylamino)carbonyl]benzyl}-3-hydroxy-5-methyl-4-oxo-7-pyridin-2-yl-4,5,6,7-tetrahydropyrazolo[1,5-a]pyrazine-2-carboxamide The title compound was prepared from 3-(benzyloxy)-N-{4-fluoro-2-[(methylamino)carbonyl]benzyl}-5-methyl-4-oxo-7-pyridin-2-yl-4,5,6,7-tetrahydropyrazolo[1,5-a]pyrazine-2-carboxamide using a hydrogenation procedure similar to that described in Example 1, Step 5. The resulting residue was purified by reverse phase chromatography on a C-18 column using a gradient elution of 95-5% $H_2O$ (0.1% TFA)/$CH_3CN$ (0.1% TFA). Collection and concentration of the appropriate fractions afforded the product. $^1H$ NMR (400 MHz, $d_6$-DMSO) δ 8.37 (m, 2H), 8.50 (d, J=4.5 Hz, 1H), 7.80 (dt, J=7.8, 1.7 Hz, 1H), 7.3-7.4 (m, 2H), 7.25 (d, J=8.9 Hz, 2H), 6.85 (d, J=7.8 Hz, 1H), 5.79 (t, J=3.5 Hz, 1H), 5.50 (ABX, J=15, 6.4 Hz, 2H), 4.25 (dd, J=13, 4.5 Hz, 1H), 3.99 (dd, J=13, 2.8 Hz, 1H), 2.83 (s, 3H), 2.75 (d, J=4.6 Hz, 3H); HRMS (FT-ICR) $C_{22}H_{21}FN_6O_4$+H=453.1675, calculated 453.1681.

EXAMPLE 48

N-(4-Fluorobenzyl)-3-hydroxy-7-isopropyl-5-methyl-4-oxo-4,5,6,7-tetrahydropyrazolo[1,5-a]pyrazine-2-carboxamide

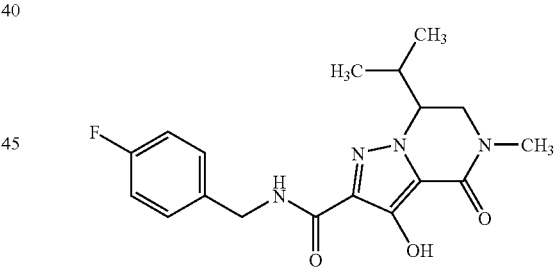

Step 1: N-(4-Fluorobenzyl)-3-hydroxy-7-isopropyl-5-methyl-4-oxo-4,5,6,7-tetrahydropyrazolo[1,5-a]pyrazine-2-carboxamide The title compound was prepared from methyl 4-benzyloxy-3-carboxy-1H-pyrazole-5-carboxylate (prepared in Example 31, Step 1) using a procedure similar to that described in Example 31, Steps 2-5, except that in Step 2,3-methyl-1-(methylamino)butan-2-ol (prepared by the methods of Horne, D. A. *Heterocycles*, 1994, 39, 139-153 and Sawarmura, M., et al., *J. Org. Chem.* 1990, 50, 5935.) was used in place of 1-(3-pyridyl)-2-methylaminoethanol. $^1H$ NMR (400 MHz, $d_6$-DMSO) δ 9.2 (bs, 1H), 8.76 (t, J=6.2 Hz, 1H), 7.35 (dd, J=8.4, 5.7 Hz, 2H), 7.14 (t, J=8.8 Hz, 2H), 4.41 (ABX, J=14.9, 6.3 Hz, 2H), 4.20 (dd, J=10.2, 4.4 Hz, 1H), 3.86 (dd, J=13.6, 4.7 Hz, 1H), 3.63 (dd, J=13.6, 3.8 Hz, 1H), 2.98 (s, 3H), 2.24 (m, 1H), 0.89 (dd, J=14.8, 6.9 Hz, 6H); HRMS (FT-ICR) $C_{18}H_{21}FN_4O_3$+H=361.1661; calculated 361.1671.

EXAMPLE 49

Enantiomers of N-{4-Fluoro-2-[(methylamino)carbonyl]benzyl}-3-hydroxy-7-isopropyl-5-methyl-4-oxo-4,5,6,7-tetrahydropyrazolo[1,5-a]pyrazine-2-carboxamide

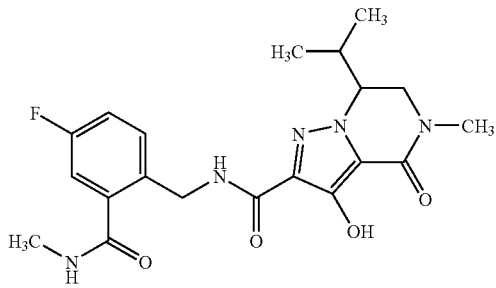

Step 1: 3-(Benzyloxy)-N-{4-fluoro-2-[(methylamino)carbonyl]benzyl}-7-isopropyl-5-methyl-4-oxo-4,5,6,7-tetrahydropyrazolo[1,5-a]pyrazine-2-carboxamide The title compound was prepared from methyl 4-benzyloxy-3-carboxy-1H-pyrazole-5-carboxylate (prepared as in Example 31, Step 1) in a procedure similar to that described in Example 47, Steps 1-2, except that 3-methyl-1-(methylamino)butan-2-ol (prepared by the methods of Horne, D. A. *Heterocycles*, 1994, 39, 139-153 and Sawarmura, M., et al., *J. Org. Chem.* 1990, 50, 5935.) was used in place of 1-(3-pyridyl)-2-methylaminoethanol. ES MS (M+1)=508.

Step 2: Enantiomers of N-{4-Fluoro-2-[(methylamino)carbonyl]benzyl}-3-hydroxy-7-isopropyl-5-methyl-4-oxo-4,5,6,7-tetrahydropyrazolo[1,5-a]pyrazine-2-carboxamide The enantiomers of 3-(benzyloxy)-N-{4-fluoro-2-[(methylamino)carbonyl]benzyl}-7-isopropyl-5-methyl-4-oxo-4,5,6,7-tetrahydropyrazolo[1,5-a]pyrazine-2-carboxamide were separated by chiral chromatography on a ChiralPak AD column using an isocratic elution of 2:3 hexane/i-PrOH. Each enantiomer of 3-(benzyloxy)-N-{4-fluoro-2-[(methylamino)carbonyl]benzyl}-7-isopropyl-5-methyl-4-oxo-4,5,6,7-tetrahydropyrazolo[1,5-a]pyrazine-2-carboxamide was hydrogenated using a procedure similar to that described in Example 1, Step 5. Early eluting enantiomer: $^1$H NMR (400 MHz, $d_6$-DMSO) δ 9.3 (bs, 1H), 8.52 (m, 2H), 7.41 (t, J=7.3 Hz, 1H), 7.27 (m, 2H), 4.51 (ABX, J=15, 6.4 Hz, 2H), 4.21 (dd, J=10.1, 4.4 Hz, 1H), 3.85 (dd, J=13.6, 4.7 Hz, 1H), 3.63 (dd, J=13.6, 3.8 Hz, 1H), 2.97 (s, 3H), 2.78 (d, J=4.6 Hz, 3H), 2.23 (m, 1H), 0.89 (dd, J=14.3, 6.9 Hz, 6H); HRMS (FT-ICR) $C_{20}H_{24}FN_5O_4$+H=418.1875; calculated 418.1885. Later eluting enantiomer: $^1$H NMR (400 MHz, $d_6$-DMSO) δ 9.28 (bs, 1H), 8.55 (m, 2H), 7.41 (t, J=7.3 Hz, 1H), 7.27 (m, 2H), 4.51 (ABX, J=15, 6.2 Hz, 2H), 4.20 (dd, J=9.9, 4.5 Hz, 1H), 3.85 (dd, J=13.6, 4.7 Hz, 1H), 3.62 (dd, J=13.6, 3.8 Hz, 1H), 2.97 (s, 3H), 2.78 (d, J=4.6 Hz, 3H), 2.23 (m, 1H), 0.89 (dd, J=14.6, 6.9 Hz, 6H); HRMS (FT-ICR) $C_{20}H_{24}FN_5O_4$+H=418.1875; calculated 418.1885.

EXAMPLE 50

Encapsulated Oral Compositions

A capsule formulation is prepared by filling standard two-piece gelatin capsules each with 100 mg of the compound of Example 1, 150 mg of lactose, 50 mg of cellulose, and 3 mg of stearic acid. Encapsulated oral compositions containing any one of the compounds of Examples 2-49 can be similarly prepared.

EXAMPLE 51

HIV Integrase Assay

Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-49 were tested in the integrase assay and all but Examples 14, 16 and 19 were found to have $IC_{50}$ values of less than or equal to 3 micromolar. The compounds of Examples 14, 16 and 19 were found to have $IC_{50}$ values of greater than 10 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 52

Assays for Inhibition of HIV Replication

An assay for the inhibition of acute HIV infection of T-lymphoid cells (alternatively referred to herein as the "spread assay") was conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 2-5, 7-13, 15, 20-24, 27 and 29-49 were found to have $IC_{95}$ values of less than or equal to 10 micromolar in the spread assay. The compounds of Examples 1, 6, 14, 16-19, 25, 26 and 28 were found to have $IC_{95}$ values of greater than 10 micromolar.

An assay for measuring the inhibition of acute HIV infection with HeLa P4-2 cells in a single cycle infectivity assay (alternatively referred to herein as the "vertical assay") was conducted in accordance with Joyce, J. G. et al., *J. Biol. Chem.* 2002, 277: 45811, Hazuda, D. J. et al., *Science*, 2000, 287, 646, and Kimpton, J. et al, *J. Virol.* 1992, 66: 2232. Representative compounds of the present invention exhibit inhibition of HIV replication in this assay. For example, the compounds of Examples 6, 17, 25 and 28 were found to have $IC_{50}$ values of less than 40 micromolar in the vertical assay. The compounds of Examples 1, 18, 19 and 26 were found to have $IC_{50}$ values of greater than 100 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of Formula I, or a pharmaceutically acceptable salt thereof:

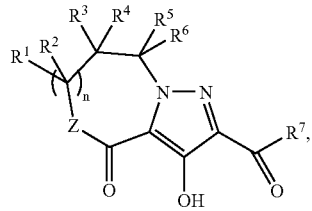

wherein:
Z is O or N(R$^8$);
R$^1$ and R$^2$ are each independently
(1) H,
(2) C$_{1-6}$ alkyl,
(3) C$_{1-6}$ haloalkyl,
(4) C$_{1-6}$ alkyl substituted with —OH, —O—C$_{1-6}$ alkyl, —O—C$_{1-6}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)SO$_2$R$^B$, —N(R$^A$)SO$_2$N(R$^C$)R$^D$, —OC(O)N(R$^C$)R$^D$, —N(R$^A$)C(O)N(R$^C$)R$^D$, or —N(R$^A$)C(O)C(O)N(R$^C$)R$^D$,
(5) CycA,
(6) AryA,
(7) HetA, or
(8) C$_{1-6}$ alkyl substituted with CycA, AryA, or HetA;
R$^3$, R$^4$, R$^5$ and R$^6$ are defined as follows:
(A) R$^3$, R$^4$, R$^5$ and R$^6$ are each independently:
(1) H,
(2) C$_{1-6}$ alkyl,
(3) C$_{1-6}$ haloalkyl,
(4) C$_{1-6}$ alkyl substituted with —OH, —O—C$_{1-6}$ alkyl, —O—C$_{1-6}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)SO$_2$R$^B$, —N(R$^A$)SO$_2$N(R$^C$)R$^D$, —OC(O)N(R$^C$)R$^D$, —N(R$^A$)C(O)N(R$^C$)R$^D$, or —N(R$^A$)C(O)C(O)N(R$^C$)R$^D$,
(5) C(O)N(R$^C$)R$^D$,
(6) CycA,
(7) AryA,
(8) HetA, or
(9) C$_{1-6}$ alkyl substituted with CycA, AryA, or HetA; or
(B) R$^4$ and R$^5$ are each independently defined as in Part (A) above; and R$^3$ and R$^6$ together form a direct bond resulting in a carbon-carbon double bond; or
(C) R$^4$ and R$^5$ together with the carbon atoms to which they are attached form a 5- to 7-membered saturated or unsaturated ring optionally containing 1 or 2 heteroatoms independently selected from N, O and S, wherein the ring is optionally substituted with from 1 to 6 substituents each of which is independently halogen, —C$_{1-6}$ alkyl, —OH, —O—C$_{1-6}$ alkyl, oxo, —CN, —NO$_2$, or —N(R$^A$)R$^B$; and R$^3$ and R$^6$ are either both absent or are each independently defined as in Part (A) above;
R$^7$ is:
(1) OH,
(2) O—C$_{1-6}$ alkyl,
(3) O-CycA,
(4) O—C$_{1-6}$ alkylene-CycA,
(5) O—C$_{1-6}$ alkylene-AryA,
(6) O—C$_{1-6}$ alkylene-HetA, or
(7) N(R$^U$)R$^V$;
R$^8$ is:
(1) H,
(2) C$_{1-6}$ alkyl,
(3) C$_{1-6}$ haloalkyl,
(4) C$_{1-6}$ alkyl substituted with —OH, —O—C$_{1-6}$ alkyl, —O—C$_{1-6}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)SO$_2$R$^B$, —N(R$^A$)SO$_2$N(R$^C$)R$^D$, —OC(O)N(R$^C$)R$^D$, —N(R$^A$)C(O)N(R$^C$)R$^D$, or —N(R$^A$)C(O)C(O)N(R$^C$)R$^D$,
(5) CycA, or
(6) C$_{1-6}$ alkyl substituted with CycA, AryA, or HetA;
n is an integer equal to zero or 1;
each R$^A$ is independently —H or —C$_{1-6}$ alkyl;
each R$^B$ is independently —H or —C$_{1-6}$ alkyl;
R$^C$ and R$^D$ are each independently —H or —C$_{1-6}$ alkyl; or R$^C$ and R$^D$ together with the N atom to which they are both attached form a 3- to 8-membered saturated ring containing (i) the N atom to which they are both attached, (ii) at least two carbon atoms, and (iii) optionally 1 or 2 additional heteroatoms independently selected from N, O and S; wherein the ring is optionally substituted with from 1 to 6 substituents each of which is independently halogen, —C$_{1-6}$ alkyl, —OH, —O—C$_{1-6}$ alkyl, oxo, —CN, —NO$_2$, or —N(R$^A$)R$^B$;
R$^U$ and R$^V$ are each independently:
(i) H,
(ii) C$_{1-6}$ alkyl,
(iii) C$_{1-6}$ haloalkyl,
(iv) C$_{1-6}$ alkyl substituted with —OH, —O—C$_{1-6}$ alkyl, —O—C$_{1-6}$ haloalkyl, —CN, —NO$_2$, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)SO$_2$R$^B$, —N(R$^A$)SO$_2$N(R$^C$)R$^D$, —OC(O)N(R$^C$)R$^D$, —N(R$^A$)C(O)N(R$^C$)R$^D$, or —N(R$^A$)C(O)C(O)N(R$^C$)R$^D$,
(v) CycA,
(vi) HetC, or
(vii) C$_{1-6}$ alkyl substituted with CycA, AryA, HetA, or HetC, with the proviso that the atom in HetC attached to the alkyl group is not a N atom; or
R$^U$ and R$^V$ together with the N atom to which they are both attached form a 3- to 8-membered saturated ring containing (i) the N atom to which they are both attached, (ii) at least two carbon atoms, and (iii) optionally containing 1 or 2 additional heteroatoms independently selected from N, O and S; wherein the saturated ring is optionally fused with a benzene ring and the optionally fused, saturated ring is:
(i) optionally substituted with from 1 to 6 substituents each of which is independently halogen, —C$_{1-6}$ alkyl, —OH, —O—C$_{1-6}$ alkyl, oxo, —CN, —NO$_2$, or —N(R$^A$)R$^B$, and
(ii) optionally substituted with 1 or 2 substituents each of which is independently CycA, AryA, HetA, HetC, or C$_{1-6}$ alkyl substituted with CycA, AryA, HetA or HetC;
each CycA is independently a C$_{3-8}$ cycloalkyl which is:
(i) optionally substituted with from 1 to 6 substituents each of which is independently halogen, —C$_{1-6}$ alkyl, —OH, —O—C$_{1-6}$ alkyl, or —C$_{1-6}$ haloalkyl, and (ii) optionally substituted with 1 or 2 substituents each of which is independently:
  (1) AryB,
  (2) HetB,
  (3) CycB, or
  (4) $C_{1-6}$ alkyl substituted with CycB, AryB, or HetB;
each AryA is independently an aryl which is:
  (i) optionally substituted with from 1 to 5 substituents each of which is independently:
    (1) —$C_{1-6}$ alkyl, which is optionally substituted with —OH, —O—$C_{1-6}$ alkyl, —O—$C_{1-6}$ haloalkyl, —CN, —$NO_2$, —$N(R^A)R^B$, —$C(O)N(R^A)R^B$, —$C(O)R^A$, —$CO_2R^A$, —$SR^A$, —$S(O)R^A$, —$SO_2R^A$, —$SO_2N(R^A)R^B$, —$N(R^A)C(O)R^B$, —$N(R^A)CO_2R^B$, —$N(R^A)SO_2R^B$, —$N(R^A)SO_2N(R^A)R^B$, —$OC(O)N(R^A)R^B$, —$N(R^A)C(O)N(R^A)R^B$, or —$N(R^A)C(O)C(O)N(R^A)R^B$,
    (2) —O—$C_{1-6}$ alkyl,
    (3) —$C_{1-6}$ haloalkyl,
    (4) —O—$C_{1-6}$ haloalkyl,
    (5) —OH,
    (6) halogen,
    (7) —CN,
    (8) —$NO_2$,
    (9) —$N(R^A)R^B$,
    (10) —$C(O)N(R^A)R^B$,
    (11) —$C(O)R^A$,
    (12) —$CO_2R^A$,
    (13) —$SR^A$,
    (14) —$S(=O)R^A$,
    (15) —$SO_2R^A$,
    (16) —$SO_2N(R^A)R^B$,
    (17) —$N(R^A)SO_2R^B$,
    (18) —$N(R^A)SO_2N(R^A)R^B$,
    (19) —$N(R^A)C(O)R^B$,
    (20) —$N(R^A)C(O)$—$C(O)N(R^A)R^B$, or
    (21) —$N(R^A)CO_2R^B$, and
  (ii) optionally substituted with 1 or 2 substituents each of which is independently:
    (1) AryB,
    (2) HetB,
    (3) CycB,
    (4) —$C_{1-6}$ alkyl substituted with CycB, AryB or HetB,
    (5) —$C(O)N(R^A)$-CycB or
    (6) —C(O)O-CycB;
each HetA is independently a heteroaryl which is:
  (i) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, or —OH; and
  (ii) optionally substituted with 1 or 2 substituents each of which is independently AryB, HetB, CycB, or —$C_{1-6}$ alkyl substituted with AryB, HetB or CycB;
each AryB is independently phenyl or naphthyl, wherein the phenyl or naphthyl is optionally substituted with from 1 to 5 substituents each of which is independently any one of the substituents (1) to (21) as defined above in part (i) of the definition of AryA;
each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy;

each CycB is independently a $C_{3-8}$ cycloalkyl which is optionally substituted with from 1 to 6 substituents each of which is independently halogen, —$C_{1-6}$ alkyl, —OH, —O—$C_{1-6}$ alkyl, or —$C_{1-6}$ haloalkyl;
HetC is a 4- to 7-membered saturated heterocyclic ring containing from 1 to 4 heteroatoms independently selected from N, O and S, wherein the heterocyclic ring is optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo;
each aryl is independently (i) phenyl or (ii) a 9- or 10-membered bicyclic, fused carbocyclic ring system in which at least one ring is aromatic; and
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

2. A compound according to claim 1, or a pharmaceutically acceptable salt thereof, wherein:
one of $R^1$ and $R^2$ is H or $C_{1-4}$ alkyl; and the other of $R^1$ and $R^2$ is:
  (1) H,
  (2) $C_{1-4}$ alkyl,
  (3) $C_{1-4}$ alkyl substituted with —OH, —O—$C_{1-4}$ alkyl, —$N(R^C)R^D$, —$C(O)N(R^C)R^D$, —$C(O)R^A$, —$CO_2R^A$, —$SR^A$, —$S(O)R^A$, —$SO_2R^A$, —$SO_2N(R^C)R^D$, —$N(R^A)C(O)R^B$, —$N(R^A)CO_2R^B$, —$N(R^A)C(O)N(R^C)R^D$, or —$N(R^A)C(O)C(O)N(R^C)R^D$,
  (4) CycA,
  (5) AryA,
  (6) HetA, or
  (7) $C_{1-4}$ alkyl substituted with CycA, AryA, or HetA;
$R^3$, $R^4$, $R^5$ and $R^6$ are defined as follows:
  (A) $R^3$, $R^4$, $R^5$ and $R^6$ are each independently
    (1) H,
    (2) $C_{1-4}$ alkyl,
    (3) $C_{1-4}$ alkyl substituted with —OH, —O—$C_{1-4}$ alkyl, —$N(R^C)R^D$, —$C(O)N(R^C)R^D$, —$C(O)R^A$, —$CO_2R^A$, —$SR^A$, —$S(O)R^A$, —$SO_2R^A$, —$SO_2N(R^C)R^D$, —$N(R^A)C(O)R^B$, —$N(R^A)CO_2R^B$, —$N(R^A)C(O)N(R^C)R^D$, or —$N(R^A)C(O)C(O)N(R^C)R^D$,
    (4) $C(O)N(R^C)R^D$,
    (5) CycA,
    (6) AryA,
    (7) HetA, or
    (8) $C_{1-4}$ alkyl substituted with CycA, AryA, or HetA;
  (B) $R^4$ and $R^5$ are each independently defined as in Part (A) above; and $R^3$ and $R^6$ together form a direct bond resulting in a carbon-carbon double bond; or
  (C) $R^4$ and $R^5$ together with the carbon atoms to which they are attached form a 5- to 7-membered saturated or unsaturated carbocyclic ring which is optionally substituted with from 1 to 4 substituents each of which is independently halogen, —$C_{1-4}$ alkyl, —OH, or —O—$C_{1-4}$ alkyl; and $R^3$ and $R^6$ are either both absent or are each independently defined as in Part (A) above;

R⁷ is:
(1) O—$C_{1-4}$ alkyl,
(2) O-CycA,
(3) O—$C_{1-6}$ alkylene-CycA,
(4) O—$C_{1-6}$ alkylene-AryA,
(5) O—$C_{1-6}$ alkylene-HetA, or
(6) N(R$^U$)R$^V$;

R⁸ is:
(1) H,
(2) $C_{1-4}$ alkyl,
(3) $C_{1-4}$ alkyl substituted with —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)C(O)N(R$^C$)R$^D$, or —N(R$^A$)C(O)C(O)N(R$^C$)R$^D$,
(4) CycA, or
(5) $C_{1-4}$ alkyl substituted with CycA, AryA, or HetA;

each R$^A$ is independently —H or —$C_{1-4}$ alkyl;
each R$^B$ is independently —H or —$C_{1-4}$ alkyl;
R$^C$ and R$^D$ are each independently —H or —$C_{1-4}$ alkyl; or R$^C$ and R$^D$ together with the N atom to which they are both attached form a 3- to 6-membered saturated ring containing (i) the N atom to which they are both attached, (ii) at least two carbon atoms, and (iii) optionally an additional heteroatom independently selected from N, O and S; wherein the ring is optionally substituted with from 1 to 5 substituents each of which is independently halogen, —$C_{1-4}$ alkyl, or oxo;

R$^U$ and R$^V$ are each independently:
(i) H,
(ii) $C_{1-4}$ alkyl,
(iii) $C_{1-4}$ alkyl substituted with —OH, —O—$C_{1-4}$ alkyl, —N(R$^C$)R$^D$, —C(O)N(R$^C$)R$^D$, —C(O)R$^A$, —CO$_2$R$^A$, —SR$^A$, —S(O)R$^A$, —SO$_2$R$^A$, —SO$_2$N(R$^C$)R$^D$, —N(R$^A$)C(O)R$^B$, —N(R$^A$)CO$_2$R$^B$, —N(R$^A$)C(O)N(R$^C$)R$^D$, or —N(R$^A$)C(O)C(O)N(R$^C$)R$^D$,
(iv) CycA,
(v) HetC, or
(vi) $C_{1-4}$ alkyl substituted with CycA, AryA, HetA, or HetC, with the proviso that the atom in HetC attached to the alkyl group is not a N atom; or
R$^U$ and R$^V$ together with the N atom to which they are both attached form a 4- to 7-membered saturated ring containing (i) the N atom to which they are both attached, (ii) at least two carbon atoms, and (iii) optionally containing an additional heteroatom independently selected from N, O and S; wherein the saturated ring is optionally fused with a benzene ring and the optionally fused, saturated ring is:
(i) optionally substituted with from 1 to 5 substituents each of which is independently halogen, —$C_{1-6}$ alkyl, —OH, oxo, —CN, —NO$_2$, or —N(R$^A$)R$^B$, and
(ii) optionally substituted with CycA, AryA, HetA, HetC, or $C_{1-4}$ alkyl substituted with CycA, AryA, HetA or HetC;

each CycA is independently a $C_{3-8}$ cycloalkyl which is:
(i) optionally substituted with from 1 to 4 substituents each of which is independently —$C_{1-4}$ alkyl, —OH, —O—$C_{1-4}$ alkyl, or —$C_{1-4}$ haloalkyl, and
(ii) optionally substituted with AryB, HetB, CycB, or $C_{1-4}$ alkyl substituted with CycB, AryB, or HetB;

each AryA is independently phenyl or naphthyl, wherein the phenyl or naphthyl is
(i) optionally substituted with from 1 to 3 substituents each of which is independently halogen, —$C_{1-4}$ alkyl, —O—$C_{1-4}$ alkyl, —$C_{1-4}$ fluoroalkyl, —CN, —CO$_2$H, —CO$_2$—$C_{1-4}$ alkyl, —SO$_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl, and
(ii) optionally substituted with AryB, HetB, CycB, —C(O)NH-CycB, —C(O)N($C_{1-4}$ alkyl)-CycB, or $C_{1-4}$ alkyl substituted with CycB, AryB, or HetB;

each HetA is independently (i) a 5- or 6-membered heteroaromatic ring containing from 1 to 3 heteroatoms independently selected from zero to 3 N atoms, zero or 1 O atom, and zero or 1 S atom, wherein each N is optionally in the form of an oxide, or (ii) a 9- or 10-membered bicyclic, fused ring system containing from 1 to 3 heteroatoms independently selected from zero to 3 N atoms, zero or 1 O atom and zero or 1 S atom, wherein either one or both of the rings contain one or more of the heteroatoms, at least one ring is aromatic, each N is optionally in the form of an oxide, and each S in a ring which is not aromatic is optionally S(O) or S(O)$_2$; wherein the heteroaromatic ring or the bicyclic, fused ring system is:
(i) optionally substituted with from 1 to 4 substituents each of which is independently halogen, —$C_{1-4}$ alkyl, or —OH; and
(ii) optionally substituted with AryB, HetB, CycB, or —$C_{1-4}$ alkyl substituted with AryB, HetB or CycB;

each AryB is independently phenyl which is optionally substituted with from 1 to 3 substituents each of which is independently halogen, —$C_{1-4}$ alkyl, —O—$C_{1-4}$ alkyl, —$C_{1-4}$ fluoroalkyl, —CN, —CO$_2$H, —CO$_2$—$C_{1-4}$ alkyl, —SO$_2$—$C_{1-4}$ alkyl, —C(O)—NH($C_{1-4}$ alkyl), —C(O)—N($C_{1-4}$ alkyl)$_2$, —NHC(O)—$C_{1-4}$ alkyl, or —N($C_{1-4}$ alkyl)C(O)—$C_{1-4}$ alkyl;

each HetB is independently a 5- or 6-membered heteroaromatic ring containing from 1 to 3 heteroatoms independently selected from zero to 3 N atoms, zero or 1 O atom, and zero or 1 S atom, wherein the heteroaromatic ring is optionally substituted with from 1 to 4 substituents each of which is independently halogen, —$C_{1-4}$ alkyl, or —OH;

each CycB is independently a $C_{3-6}$ cycloalkyl which is optionally substituted with from 1 to 4 substituents each of which is independently —$C_{1-6}$ alkyl, —OH, or —O—$C_{1-6}$ alkyl; and HetC is a 4- to 7-membered saturated heterocyclic ring containing from 1 to 3 heteroatoms independently selected from 1 to 3 N atoms, zero or 1 O atom, and zero or 1 S atom, wherein the heterocyclic ring is optionally substituted with from 1 to 4 substituents each of which is independently —$C_{1-6}$ alkyl or oxo.

3. A compound according to claim 2, or a pharmaceutically acceptable salt thereof, wherein:
one of R¹ and R² is H or $C_{1-4}$ alkyl; and the other of R¹ and R² is:
(1) H,
(2) $C_{1-4}$ alkyl,
(3) $C_{1-3}$ alkyl substituted with —N(R$^C$)R$^D$ or —C(O)N(R$^C$)R$^D$,
(4) CycA, AryA, or HetA,
(5) (CH$_2$)$_{1-2}$-CycA, (CH$_2$)$_{1-2}$-AryA, or (CH$_2$)$_{1-2}$-HetA, or
(6) CH(CH$_3$)-CycA, CH(CH$_3$)-AryA, or CH(CH$_3$)-HetA;

R³, R⁴, R⁵ and R⁶ are defined as follows:
(A) R³ and R⁶ are each independently H or $C_{1-4}$ alkyl; and R⁴ and R⁵ are each independently:
(1) H,
(2) $C_{1-4}$ alkyl, (3) C(O)N(R^C)R^D,
(4) C$_{1-3}$ alkyl substituted with —N(R^C)R^D or —C(O)N(R^C)R^D,
(5) CycA, AryA, or HetA,
(6) (CH$_2$)$_{1-2}$-CycA, (CH$_2$)$_{1-2}$-AryA, or (CH$_2$)$_{1-2}$-HetA, or
(7) CH(CH$_3$)-CycA, CH(CH$_3$)-AryA, or CH(CH$_3$)-HetA;
(B) R$^4$ and R$^5$ are each independently defined as in Part (A) above; and R$^3$ and R$^6$ together form a direct bond resulting in a carbon-carbon double bond; or
(C) R$^4$ and R$^5$ together with the carbon atoms to which they are attached form a benzene ring which is optionally substituted with from 1 to 4 substituents each of which is independently halogen, —C$_{1-4}$ alkyl, —OH, or —O—C$_{1-4}$ alkyl; and R$^3$ and R$^6$ are both absent;

R$^7$ is:
(1) O—C$_{1-4}$ alkyl, or
(2) N(R$^U$)R$^V$;

R$^8$ is:
(1) H,
(2) C$_{1-4}$ alkyl,
(3) C$_{1-3}$ alkyl substituted with —N(R^C)R^D or —C(O)N(R^C)R^D,
(4) C$_{3-6}$ cycloalkyl,
(5) (CH$_2$)$_{1-2}$-CycA, (CH$_2$)$_{1-2}$-AryA, or (CH$_2$)$_{1-2}$-HetA, or
(6) CH(CH$_3$)-CycA, CH(CH$_3$)-AryA, or CH(CH$_3$)-HetA;

R$^U$ is:
(i) H,
(ii) C$_{1-4}$ alkyl,
(iii) C$_{2-4}$ alkyl substituted with OH, O—C$_{1-4}$ alkyl, NH$_2$, NH(C$_{1-4}$ alkyl), or N(C$_{1-4}$ alkyl)$_2$;

R$^V$ is:
(i) H,
(ii) C$_{1-4}$ alkyl,
(iii) C$_{1-3}$ alkyl substituted with —N(R^C)R^D or —C(O)N(R^C)R^D,
(iv) a saturated heterocycle selected from the group consisting of:

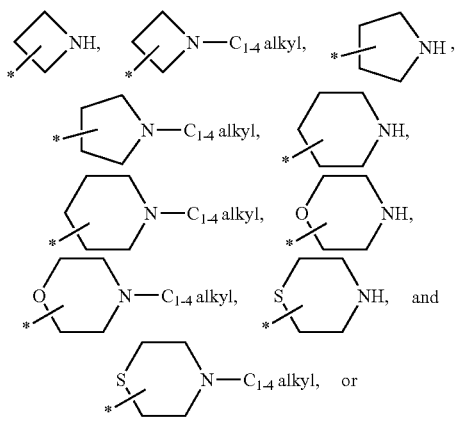

(v) (CH$_2$)$_{1-2}$-CycA, (CH$_2$)$_{1-2}$-AryA, or (CH$_2$)$_{1-2}$-HetA, or
(vi) CH(CH$_3$)-CycA, CH(CH$_3$)-AryA, or CH(CH$_3$)-HetA;

or alternatively R$^U$ and R$^V$ together with the N atom to which they are both attached form a saturated heterocyclic ring optionally fused to a benzene ring, wherein the optionally fused heterocylic ring is selected from the group consisting of:

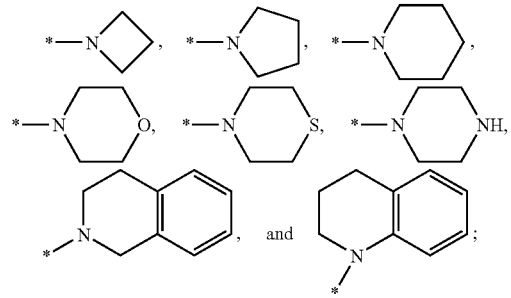

wherein the ring is optionally substituted with a phenyl, is optionally substituted with 1 or 2-C$_{1-4}$ alkyl groups, and is optionally substituted with an oxo, with the proviso that the optional oxo substituent is attached to a carbon atom in the saturated heterocyclic ring;

each N(R^C)R^D is selected from the group consisting of NH$_2$, NH(C$_{1-4}$ alkyl), N(C$_{1-4}$ alkyl)$_2$,

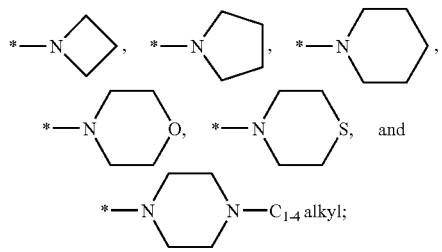

the asterisk * in each of the rings defined by R$^U$ and R$^V$ together and by R^C and R^D together denotes the point of attachment of the ring to the rest of the compound; and each CycA is independently C$_{3-6}$ cycloalkyl;

each AryA is independently phenyl which is:
(i) optionally substituted with from 1 to 3 substituents each of which is independently halogen, —C$_{1-4}$ alkyl, —O—C$_{1-4}$ alkyl, —C$_{1-4}$ fluoroalkyl, —CN, —CO$_2$H, —CO$_2$—C$_{1-4}$ alkyl, —SO$_2$—C$_{1-4}$ alkyl, —C(O)—NH(C$_{1-4}$ alkyl), —C(O)—N(C$_{1-4}$ alkyl)$_2$, —NHC(O)—C$_{1-4}$ alkyl, or —N(C$_{1-4}$ alkyl)C(O)—C$_{1-4}$ alkyl, and
(ii) optionally substituted with —C(O)NH—C$_{3-6}$ cycloalkyl or —C(O)N(C$_{1-4}$ alkyl)-C$_{3-6}$ cycloalkyl; and each HetA is independently a 5- or 6-membered heteroaromatic ring containing from 1 to 3 heteroatoms independently selected from zero to 3 N atoms, zero or 1 O atom, and zero or 1 S atom, wherein the ring is optionally fused with a benzene ring and wherein the optionally fused heteroaromatic ring is optionally substituted with from 1 to 3 substituents each of which is independently —C$_{1-4}$ alkyl or —OH.

4. A compound according to claim 3, or a pharmaceutically acceptable salt thereof, wherein:
Z is N(R$^8$);
R$^1$ and R$^2$ are each independently H or C$_{1-4}$ alkyl;
R$^3$, R$^4$, R$^5$ and R$^6$ are defined as follows:

(A) $R^3$ and $R^6$ are each independently H or $C_{1-4}$ alkyl; one of $R^4$ and $R^5$ is H or $C_{1-4}$ alkyl, and the other of $R^4$ and $R^5$ is:
   (1) H,
   (2) $C_{1-4}$ alkyl,
   (3) $C(O)N(R^C)R^D$,
   (4) $(CH_2)_{1-3}$—$N(R^C)R^D$ or $(CH_2)_{1-3}$—$C(O)N(R^C)R^D$,
   (5) CycA, AryA, or HetA, or
   (6) $CH_2$-CycA, $CH_2$-AryA, or $CH_2$-HetA;
(B) $R^4$ and $R^5$ are each defined as in Part (A) above; and $R^3$ and $R^6$ together form a direct bond resulting in a carbon-carbon double bond; or
(C) $R^4$ and $R^5$ together with the carbon atoms to which they are attached form a benzene ring which is optionally substituted with from 1 to 4 substituents each of which is independently halogen, —$C_{1-4}$ alkyl, —OH, or —O—$C_{1-4}$ alkyl; and $R^3$ and $R^6$ are both absent;
$R^7$ is:
   (1) O—$C_{1-4}$ alkyl, or
   (2) $N(R^U)R^V$;
$R^8$ is:
   (1) H,
   (2) $C_{1-4}$ alkyl,
   (3) $(CH_2)_{1-3}$—$N(R^C)R^D$ or $(CH_2)_{1-3}$—$C(O)N(R^C)R^D$,
   (4) $C_{3-6}$ cycloalkyl, or
   (5) $CH_2$-CycA, $CH_2$-AryA, or $CH_2$-HetA;
$R^U$ is:
   (i) H,
   (ii) $C_{1-4}$ alkyl, or
   (iii) $(CH_2)_{2-4}T$, wherein T is selected from the group consisting of OH, O—$C_{1-4}$ alkyl, $NH_2$, $NH(C_{1-4}$ alkyl), and $N(C_{1-4}$ alkyl$)_2$;
$R^V$ is:
   (i) H,
   (ii) $C_{1-4}$ alkyl,
   (iii) $(CH_2)_{1-3}$—$N(R^C)R^D$ or $(CH_2)_{1-3}$—$C(O)N(R^C)R^D$,
   (iv) a saturated heterocycle selected from the group consisting of:

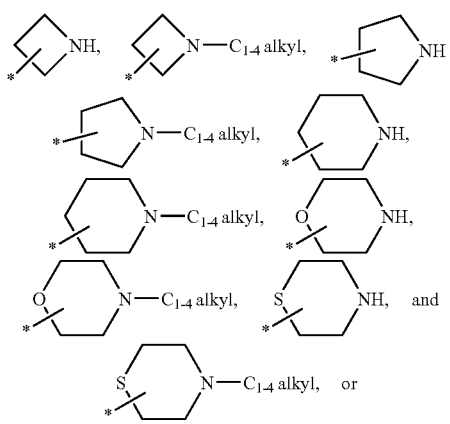

(v) $CH_2$-CycA, $CH_2$-AryA, or $CH_2$-HetA;
or alternatively $R^U$ and $R^V$ together with the N atom to which they are both attached form a saturated heterocyclic ring optionally fused to a benzene ring, wherein the optionally fused heterocylic ring is selected from the group consisting of:

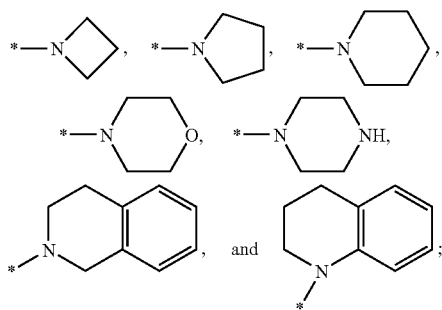

wherein the ring is optionally substituted with a phenyl, is optionally substituted with 1 or 2-$C_{1-4}$ alkyl groups, and is optionally substituted with an oxo, with the proviso that the optional oxo substituent is attached to a carbon atom in the saturated heterocyclic ring.

5. A compound according to claim 4, or a pharmaceutically acceptable salt thereof, wherein:
$R^1$ and $R^2$ are both H;
$R^3$, $R^4$, $R^5$ and $R^6$ are defined as follows:
   (A) $R^3$ is H; $R^4$ is H or methyl; $R^6$ is H or methyl; and $R^5$ is H, $C_{1-3}$ alkyl, $(CH_2)_{1-2}NH_2$, $(CH_2)_{1-2}NH(C_{1-3}$ alkyl), $(CH_2)_{1-2}N(C_{1-3}$ alkyl$)_2$,

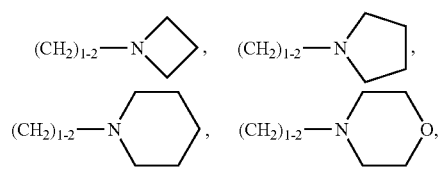

$C(O)NH_2$, $C(O)NH(C_{1-3}$ alkyl), $C(O)N(C_{1-3}$ alkyl$)_2$,

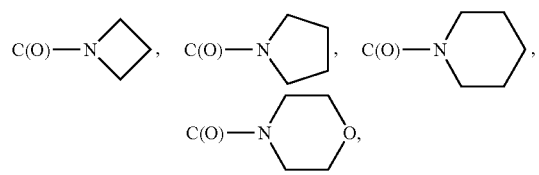

phenyl optionally substituted with 1 or 2 substituents independently selected from halogen and CN, benzyl, or a heteroaromatic ring selected from the group consisting of pyrrolyl, pyrazolyl, imidazolyl, oxazolyl, thiazolyl, triazolyl, oxadiazolyl, thiadiazolyl, pyridinyl, pyrimidinyl, and pyrazinal, wherein the heteroaromatic ring is optionally substituted with 1 or 2 substituents each of which is independently methyl, ethyl, n-propyl, or isopropyl;
   (B) $R^4$ and $R^5$ are each defined as in Part (A) above; and $R^3$ and $R^6$ together form a direct bond resulting in a carbon-carbon double bond; or
   (C) $R^4$ and $R^5$ together with the carbon atoms to which they are attached form a benzene ring; and $R^3$ and $R^6$ are both absent;

$R^7$ is:

(1) O—$C_{1-3}$ alkyl,
(2) $NH_2$,
(3) NH($C_{1-4}$ alkyl),
(4) N($C_{1-4}$ alkyl)$_2$,
(5) NHCH$_2$C(O)NH($C_{1-4}$ alkyl),
(6) NHCH$_2$C(O)N($C_{1-4}$ alkyl)$_2$,

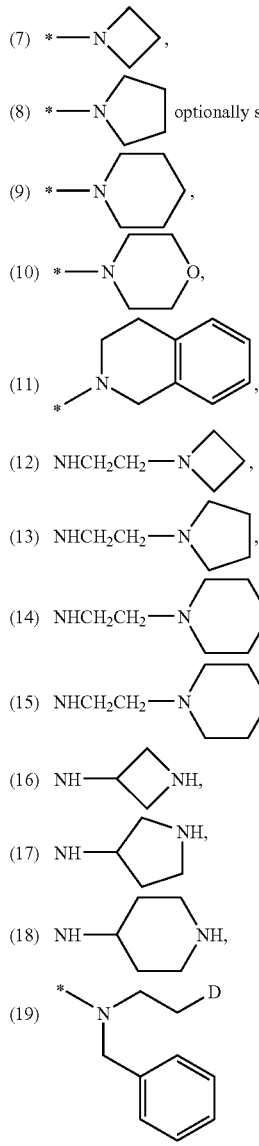

(19) with wherein D is OH, NH$_2$, NH($C_{1-3}$ alkyl), or N($C_{1-3}$ alkyl)$_2$,

(20) NH—CH$_2$-phenyl or N(CH$_3$)—CH$_2$-phenyl, where the phenyl is:
  (i) optionally substituted with 1 or 2 substituents each of which is independently bromo, chloro, fluoro, $C_{1-3}$ alkyl, CF$_3$, C(O)NH$_2$, C(O)NH($C_{1-3}$ alkyl), C(O)N($C_{1-3}$ alkyl)$_2$, SO$_2$CH$_3$, or SO$_2$CH$_2$CH$_3$, and
  (ii) optionally substituted with C(O)NH-cyclopropyl or C(O)N(CH$_3$)-cyclopropyl, or

(21) NH-E or N(CH$_3$)-E, where E is:

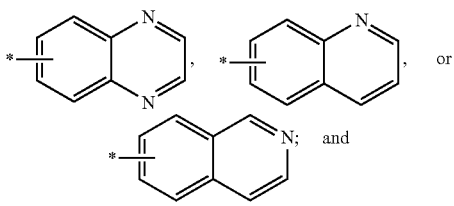

$R^8$ is:

(1) H,
(2) $C_{1-3}$ alkyl,

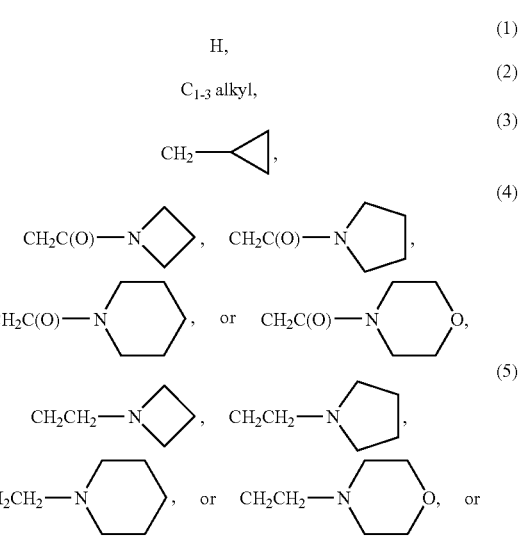

(6) CH$_2$-phenyl, where the phenyl is optionally substituted with 1 or 2 substituents each of which is independently bromo, chloro, fluoro, $C_{1-3}$ alkyl, CF$_3$, C(O)NH$_2$, C(O)NH($C_{1-3}$ alkyl), C(O)N($C_{1-3}$ alkyl)$_2$, SO$_2$CH$_3$, or SO$_2$CH$_2$CH$_3$.

6. A compound according to claim 5, or a pharmaceutically acceptable salt thereof, wherein:

$R^3$ is H; $R^6$ is H or methyl; or alternatively $R^3$ and $R^6$ together form a direct bond resulting in a carbon-carbon double bond;

$R^4$ is H or methyl;

$R^5$ is H, methyl, isopropyl,

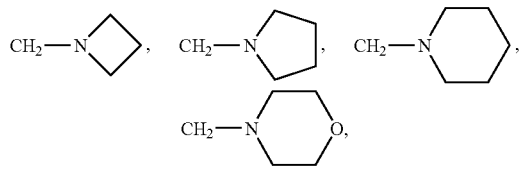

C(O)NH(CH$_3$), C(O)N(CH$_3$)$_2$,

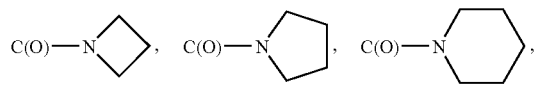

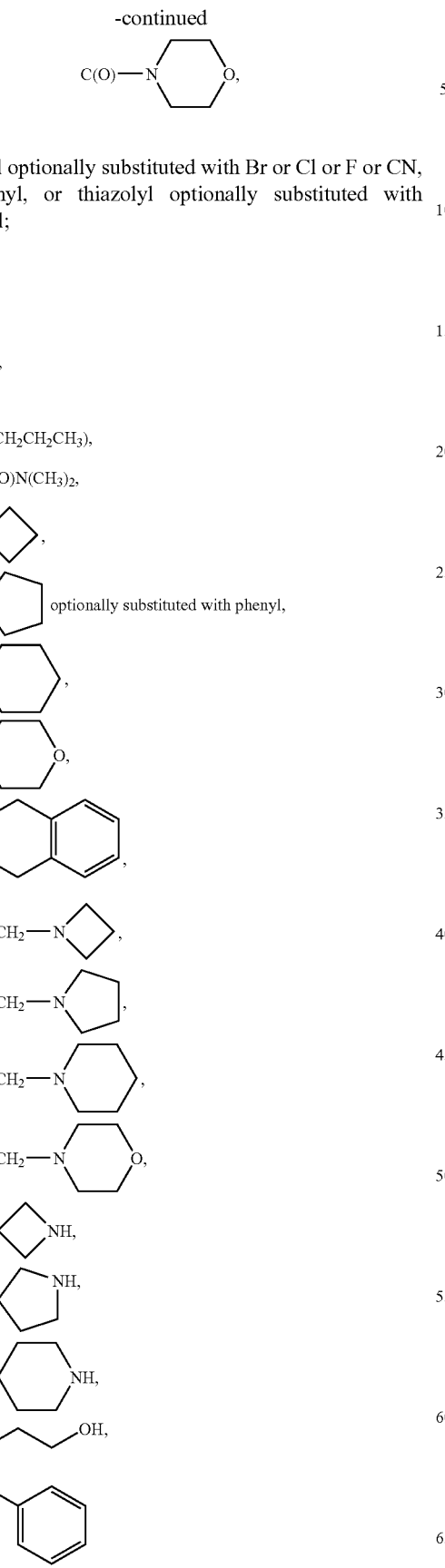

phenyl optionally substituted with Br or Cl or F or CN, pyridinyl, or thiazolyl optionally substituted with methyl;

$R^7$ is:

(1) $OCH_3$,
(2) $NH(CH_3)$,
(3) $N(CH_3)_2$,
(4) $NH(CH_2CH_2CH_2CH_3)$,
(5) $NHCH_2C(O)N(CH_3)_2$, (6) azetidinyl,
(7) pyrrolidinyl optionally substituted with phenyl,
(8) piperidinyl,
(9) morpholinyl,
(10) tetrahydroisoquinolinyl,
(11) $NHCH_2CH_2$-azetidinyl,
(12) $NHCH_2CH_2$-pyrrolidinyl,
(13) $NHCH_2CH_2$-piperidinyl,
(14) $NHCH_2CH_2$-morpholinyl,
(15) NH-azetidinyl-NH,
(16) NH-pyrrolidinyl-NH,
(17) NH-piperidinyl-NH,
(18) N-benzyl-N-(2-hydroxyethyl),

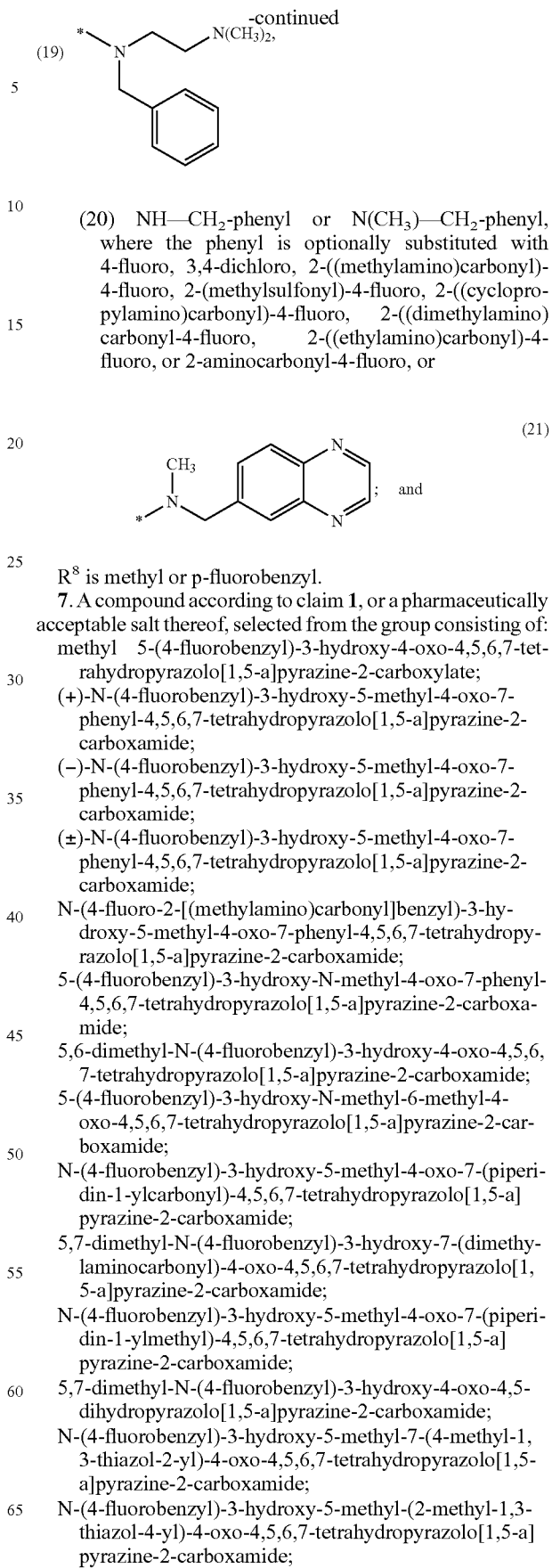

(19) N-benzyl-N-(2-(dimethylamino)ethyl),

(20) NH—$CH_2$-phenyl or N($CH_3$)—$CH_2$-phenyl, where the phenyl is optionally substituted with 4-fluoro, 3,4-dichloro, 2-((methylamino)carbonyl)-4-fluoro, 2-(methylsulfonyl)-4-fluoro, 2-((cyclopropylamino)carbonyl)-4-fluoro, 2-((dimethylamino)carbonyl-4-fluoro, 2-((ethylamino)carbonyl)-4-fluoro, or 2-aminocarbonyl-4-fluoro, or

(21) N-methyl-N-(quinoxalin-6-ylmethyl); and $R^8$ is methyl or p-fluorobenzyl.

7. A compound according to claim 1, or a pharmaceutically acceptable salt thereof, selected from the group consisting of:
methyl 5-(4-fluorobenzyl)-3-hydroxy-4-oxo-4,5,6,7-tetrahydropyrazolo[1,5-a]pyrazine-2-carboxylate;
(+)-N-(4-fluorobenzyl)-3-hydroxy-5-methyl-4-oxo-7-phenyl-4,5,6,7-tetrahydropyrazolo[1,5-a]pyrazine-2-carboxamide;
(−)-N-(4-fluorobenzyl)-3-hydroxy-5-methyl-4-oxo-7-phenyl-4,5,6,7-tetrahydropyrazolo[1,5-a]pyrazine-2-carboxamide;
(±)-N-(4-fluorobenzyl)-3-hydroxy-5-methyl-4-oxo-7-phenyl-4,5,6,7-tetrahydropyrazolo[1,5-a]pyrazine-2-carboxamide;
N-(4-fluoro-2-[(methylamino)carbonyl]benzyl)-3-hydroxy-5-methyl-4-oxo-7-phenyl-4,5,6,7-tetrahydropyrazolo[1,5-a]pyrazine-2-carboxamide;
5-(4-fluorobenzyl)-3-hydroxy-N-methyl-4-oxo-7-phenyl-4,5,6,7-tetrahydropyrazolo[1,5-a]pyrazine-2-carboxamide;
5,6-dimethyl-N-(4-fluorobenzyl)-3-hydroxy-4-oxo-4,5,6,7-tetrahydropyrazolo[1,5-a]pyrazine-2-carboxamide;
5-(4-fluorobenzyl)-3-hydroxy-N-methyl-6-methyl-4-oxo-4,5,6,7-tetrahydropyrazolo[1,5-a]pyrazine-2-carboxamide;
N-(4-fluorobenzyl)-3-hydroxy-5-methyl-4-oxo-7-(piperidin-1-ylcarbonyl)-4,5,6,7-tetrahydropyrazolo[1,5-a]pyrazine-2-carboxamide;
5,7-dimethyl-N-(4-fluorobenzyl)-3-hydroxy-7-(dimethylaminocarbonyl)-4-oxo-4,5,6,7-tetrahydropyrazolo[1,5-a]pyrazine-2-carboxamide;
N-(4-fluorobenzyl)-3-hydroxy-5-methyl-4-oxo-7-(piperidin-1-ylmethyl)-4,5,6,7-tetrahydropyrazolo[1,5-a]pyrazine-2-carboxamide;
5,7-dimethyl-N-(4-fluorobenzyl)-3-hydroxy-4-oxo-4,5-dihydropyrazolo[1,5-a]pyrazine-2-carboxamide;
N-(4-fluorobenzyl)-3-hydroxy-5-methyl-7-(4-methyl-1,3-thiazol-2-yl)-4-oxo-4,5,6,7-tetrahydropyrazolo[1,5-a]pyrazine-2-carboxamide;
N-(4-fluorobenzyl)-3-hydroxy-5-methyl-(2-methyl-1,3-thiazol-4-yl)-4-oxo-4,5,6,7-tetrahydropyrazolo[1,5-a]pyrazine-2-carboxamide;

2-[4-fluorobenzyl(methyl)aminocarbonyl]-3-hydroxy-5-methyl-4-oxo-4,5,6,7-tetrahydropyrazolo[1,5-a]pyrazine-2-carboxamide;

3-hydroxy-5-methyl-4-oxo-2-[(1,2,3,4-tetrahydro-isoquinolin-2-yl)carbonyl]-4,5,6,7-tetrahydropyrazolo[1,5-a]pyrazine;

N-[4-fluoro-2-(methylsulfonyl)benzyl]-3-hydroxy-5-methyl-4-oxo-4,5,6,7-tetrahydropyrazolo[1,5-a]pyrazine-2-carboxamide;

3-hydroxy-5-methyl-4-oxo-2-[(2-phenylpyrrolidin-1-yl)carbonyl]-4,5,6,7-tetrahydropyrazolo[1,5-a]pyrazine;

3-hydroxy-5-methyl-4-oxo-2-{[quinoxalin-6-ylmethyl(methyl)amino]carbonyl}-4,5,6,7-tetrahydropyrazolo[1,5-a]pyrazine;

2-[benzyl(2-hydroxyethyl)aminocarbonyl]-3-hydroxy-5-methyl-4-oxo-4,5,6,7-tetrahydropyrazolo[1,5-a]pyrazine;

2-{benzyl[2-(dimethylamino)ethyl]aminocarbonyl}-3-hydroxy-5-methyl-4-oxo-4,5,6,7-tetrahydropyrazolo[1,5-a]pyrazine;

N-(3,4-dichlorobenzyl)-3-hydroxy-5-[2-(4-morpholinyl)-2-oxoethyl]-4-oxo-4,5,6,7-tetrahydropyrazolo[1,5-a]pyrazine-2-carboxamide;

5-cyclopropylmethyl-N-(3,4-dichlorobenzyl)-3-hydroxy-4-oxo-4,5,6,7-tetrahydropyrazolo[1,5-a]pyrazine-2-carboxamide;

N-(3,4-dichlorobenzyl)-3-hydroxy-5-[2-(4-morpholinyl)ethyl]-4-oxo-4,5,6,7-tetrahydropyrazolo[1,5-a]pyrazine-2-carboxamide;

5-(4-fluorobenzyl)-3-hydroxy-N-[2-(4-morpholinyl)ethyl]-4-oxo-4,5,6,7-tetrahydropyrazolo[1,5-a]pyrazine-2-carboxamide;

N-butyl-5-(4-fluorobenzyl)-3-hydroxy-4-oxo-4,5,6,7-tetrahydropyrazolo[1,5-a]pyrazine-2-carboxamide;

5-(4-fluorobenzyl)-3-hydroxy-4-oxo-N-(4-piperidinyl)-4,5,6,7-tetrahydropyrazolo[1,5-a]pyrazine-2-carboxamide;

N-[2-(dimethylamino)-2-oxoethyl]-5-(4-fluorobenzyl)-3-hydroxy-4-oxo-N-(4-piperidinyl)-4,5,6,7-tetrahydropyrazolo[1,5-a]pyrazine-2-carboxamide;

2-(azetidin-1-ylcarbonyl)-5-(4-fluorobenzyl)-3-hydroxy-4-oxo-4,5,6,7-tetrahydropyrazolo[1,5-a]pyrazine;

5-(4-fluorobenzyl)-3-hydroxy-2-(morpholin-4-ylcarbonyl)-4-oxo-4,5,6,7-tetrahydropyrazolo[1,5-a]pyrazine;

N-(4-fluorobenzyl)-3-hydroxy-4-oxo-5,6,7,8-tetrahydro-4H-pyrazolo[1,5-a][1,4]diazepine-2-carboxamide;

methyl 5-(4-fluorobenzyl)-3-hydroxy-4-oxo-5,6,7,8-tetrahydro-4H-pyrazolo[1,5-a][1,4]diazepine-2-carboxylate;

N-(4-fluorobenzyl)-3-hydroxy-5-methyl-4-oxo-7-pyridin-3-yl-4,5,6,7-tetrahydropyrazolo[1,5-a]pyrazine-2-carboxamide;

N-(4-fluorobenzyl)-3-hydroxy-5-methyl-4-oxo-4,5-dihydropyrazolo[1,5-a]quinoxaline-2-carboxamide;

(7S)—N-{4-Fluoro-2-[(methylamino)carbonyl]benzyl}-3-hydroxy-5-methyl-4-oxo-7-phenyl-4,5,6,7-tetrahydropyrazolo[1,5-a]pyrazine-2-carboxamide;

(7R)—N-{4-Fluoro-2-[(methylamino)carbonyl]benzyl}-3-hydroxy-5-methyl-4-oxo-7-phenyl-4,5,6,7-tetrahydropyrazolo[1,5-a]pyrazine-2-carboxamide;

(7R)—N-{2-[(Cyclopropylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7S)—N-{2-[(Cyclopropylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7R)—N-{2-[(Dimethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7S)—N-{2-[(Dimethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7R)—N-{2-[(Ethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7S)—N-{2-[(Ethylamino)carbonyl]-4-fluorobenzyl}-3-hydroxy-5-methyl-4-oxo-7-phenyl-4,5,6,7-tetrahydropyrazolo[1,5-a]pyrazine-2-carboxamide;

(7R)—N-[2-(Aminocarbonyl)-4-fluorobenzyl]-3-hydroxy-5-methyl-4-oxo-7-phenyl-4,5,6,7-tetrahydropyrazolo[1,5-a]pyrazine-2-carboxamide;

(7S)—N-[2-(Aminocarbonyl)-4-fluorobenzyl]-3-hydroxy-5-methyl-4-oxo-7-phenyl-4,5,6,7-tetrahydropyrazolo[1,5-a]pyrazine-2-carboxamide;

7-(3-Bromophenyl)-N-(4-fluorobenzyl)-3-hydroxy-5-methyl-4-oxo-4,5,6,7-tetrahydropyrazolo[1,5-a]pyrazine-2-carboxamide;

7-(3-Cyanophenyl)-N-(4-fluorobenzyl)-3-hydroxy-5-methyl-4-oxo-4,5,6,7-tetrahydropyrazolo[1,5-a]pyrazine-2-carboxamide;

N-(4-Fluorobenzyl)-3-hydroxy-5-methyl-4-oxo-7-pyridin-4-yl-4,5,6,7-tetrahydropyrazolo[1,5-a]pyrazine-2-carboxamide;

N-(3-Chloro-4-fluorobenzyl)-3-hydroxy-5-methyl-4-oxo-7-pyridin-4-yl-4,5,6,7-tetrahydropyrazolo[1,5-a]pyrazine-2-carboxamide;

N-{4-Fluoro-2-[(methylamino)carbonyl]benzyl}-3-hydroxy-5-methyl-4-oxo-7-pyridin-2-yl-4,5,6,7-tetrahydropyrazolo[1,5-a]pyrazine-2-carboxamide;

N-(4-Fluorobenzyl)-3-hydroxy-7-isopropyl-5-methyl-4-oxo-4,5,6,7-tetrahydropyrazolo[1,5-a]pyrazine-2-carboxamide; and N-{4-Fluoro-2-[(methylamino)carbonyl]benzyl}-3-hydroxy-7-isopropyl-5-methyl-4-oxo-4,5,6,7-tetrahydropyrazolo[1,5-a]pyrazine-2-carboxamide and enantiomers thereof.

8. A pharmaceutical composition comprising an effective amount of a compound according to claim 1, or a pharmaceutically acceptable salt thereof, and a pharmaceutically acceptable carrier.

9. A method of inhibiting HIV integrase in a subject in need thereof which comprises administering to the subject an effective amount of the compound according to claim 1, or a pharmaceutically acceptable salt thereof.

10. A method for treating infection by HIV or for treating or delaying the onset of AIDS in a subject in need thereof which comprises administering to the subject an effective amount of the compound according to claim 1, or a pharmaceutically acceptable salt thereof.

11. A pharmaceutical combination which is (i) a compound according to claim 1, or a pharmaceutically acceptable salt thereof, and (ii) an HIV infection/AIDS antiviral agent selected from the group consisting of HIV protease inhibitors, non-nucleoside HIV reverse transcriptase inhibitors and nucleoside HIV reverse transcriptase inhibitors; wherein the compound of (i) or its pharmaceutically acceptable salt and the HIV infection/AIDS antiviral agent of (ii) are each employed in an amount that renders the combination effective for inhibiting HIV integrase, for treating infection by HIV, or for treating or delaying the onset of AIDS.

* * * * *